United States Patent [19]

Hamano et al.

[11] Patent Number: 5,894,322
[45] Date of Patent: Apr. 13, 1999

[54] ENDOSCOPE SYSTEM WITH IMPROVED CONTROLLER

[75] Inventors: Masahiko Hamano, Hino; Toshiaki Nishikori, Sagamihara; Tsuguhisa Sasai, Tsukui-machi; Mutsumi Oshima, Machida; Hiroyuki Ushifusa; Hideyuki Shouji, both of Hachioji; Atsushi Amano, Tama; Kouji Okada, Yokohama; Kazufumi Takamizawa, Chofu; Kenya Inomata, Mitaka; Shingo Kato, Hachioji, all of Japan

[73] Assignee: Olympus Optical Co., Ltd., Tokyo, Japan

[21] Appl. No.: 08/088,980

[22] Filed: Jul. 1, 1993

Related U.S. Application Data

[63] Continuation-in-part of application No. 08/051,812, Apr. 26, 1993, abandoned, which is a continuation-in-part of application No. 07/820,994, Jan. 15, 1992, abandoned.

[30] Foreign Application Priority Data

| Jul. 3, 1992 | [JP] | Japan | 4-177191 |
| Jul. 3, 1992 | [JP] | Japan | 4-177192 |
| Jul. 3, 1992 | [JP] | Japan | 4-177210 |
| Jul. 3, 1992 | [JP] | Japan | 4-177214 |

[51] Int. Cl.⁶ ............................................ H04N 7/18
[52] U.S. Cl. .................. 248/68; 348/65; 348/68; 348/69; 348/67
[58] Field of Search ............................ 348/65, 67, 68, 348/69, 66, 74, 586, 587; 128/662.06, 622.05, 662.04

[56] References Cited

U.S. PATENT DOCUMENTS

| 4,998,972 | 3/1991 | Chin et al. | 348/67 |
| 5,036,361 | 7/1991 | Filion et al. | |
| 5,099,846 | 3/1992 | Hardy | 128/662.06 |
| 5,121,750 | 6/1992 | Katims | 128/6 |
| 5,184,601 | 2/1993 | Putnam | 128/6 |
| 5,187,579 | 2/1993 | Hiyama | 348/586 |
| 5,200,838 | 4/1993 | Nudelman et al. | 128/6 |
| 5,217,003 | 6/1993 | Wilk | 128/6 |
| 5,235,965 | 8/1993 | Hiroya | 128/6 |
| 5,243,967 | 9/1993 | Hibino | 128/662.06 |
| 5,257,629 | 11/1993 | Kitney | 128/662.06 |

FOREIGN PATENT DOCUMENTS

| 3-284230 | 12/1991 | Japan . |
| 3-284232 | 12/1991 | Japan . |
| 3284230 | 12/1991 | Japan . |
| 3284232 | 12/1991 | Japan . |

*Primary Examiner*—Tommy P. Chin
*Assistant Examiner*—Anand S. Rao
*Attorney, Agent, or Firm*—Armstrong, Westerman Hattori McLeland & Naughton

[57] ABSTRACT

An endoscope system comprises a plurality of endoscope components including at least one endoscope light source apparatus for supplying illumination light to an endoscope and at least one video signal processing unit for processing video signals provided by the endoscope, a main control unit for controlling the plurality of endoscope system components, and a main operational instruction unit connected to the main control unit and used to operate the plurality of endoscope system components. The main operational instruction unit includes a display capable of selectively displaying operational instruction input screens associated with functions possessed by the plurality of endoscope system components.

31 Claims, 76 Drawing Sheets

SCREEN CHANGE ROUTINE

TURNING ON/OFF SWITCHES IN CV-100 MODE

TURNING ON/OFF SWITCHES
IN LIGHT-SOURCE OES MODE

TURNING ON/OFF SWITCHES
IN LIGHT-SOURCE CCU MODE

FIG.15(F)

| ID. NO | NAME | |
|---|---|---|
| 01 | | |
| 02 | | |
| 03 | | |
| 04 | | |
| 05 | | |
| 06 | | |
| 07 | | |
| 08 | | |
| 09 | | |
| 10 | | |
| 11 | | |
| 12 | | RECALL NO 12 |
| 13 | | |
| 14 | | |
| 15 | | |
| 16 | | |
| 17 | | |
| 18 | | |
| 19 | | |
| 20 | | |

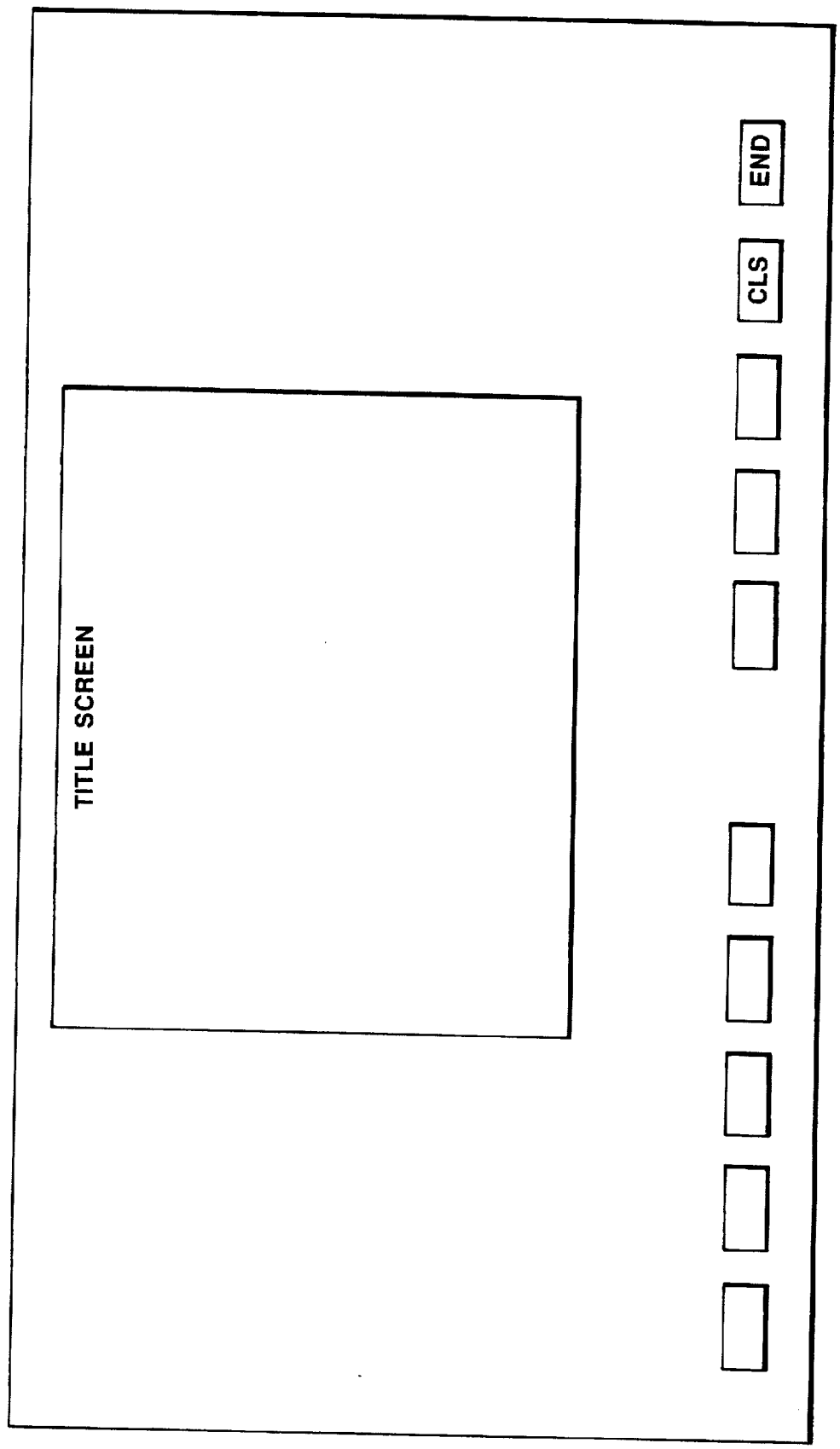

FIG.15(I)

ID. NO     NAME 01
02
03
04
05
06
07
08
09
10
11
12
13
14
15
16
17
18
19
20

ENTER NO 1

END

NAME:

SEX:

AGE:

D.O. BIRTH: / /

END

ST-PAT

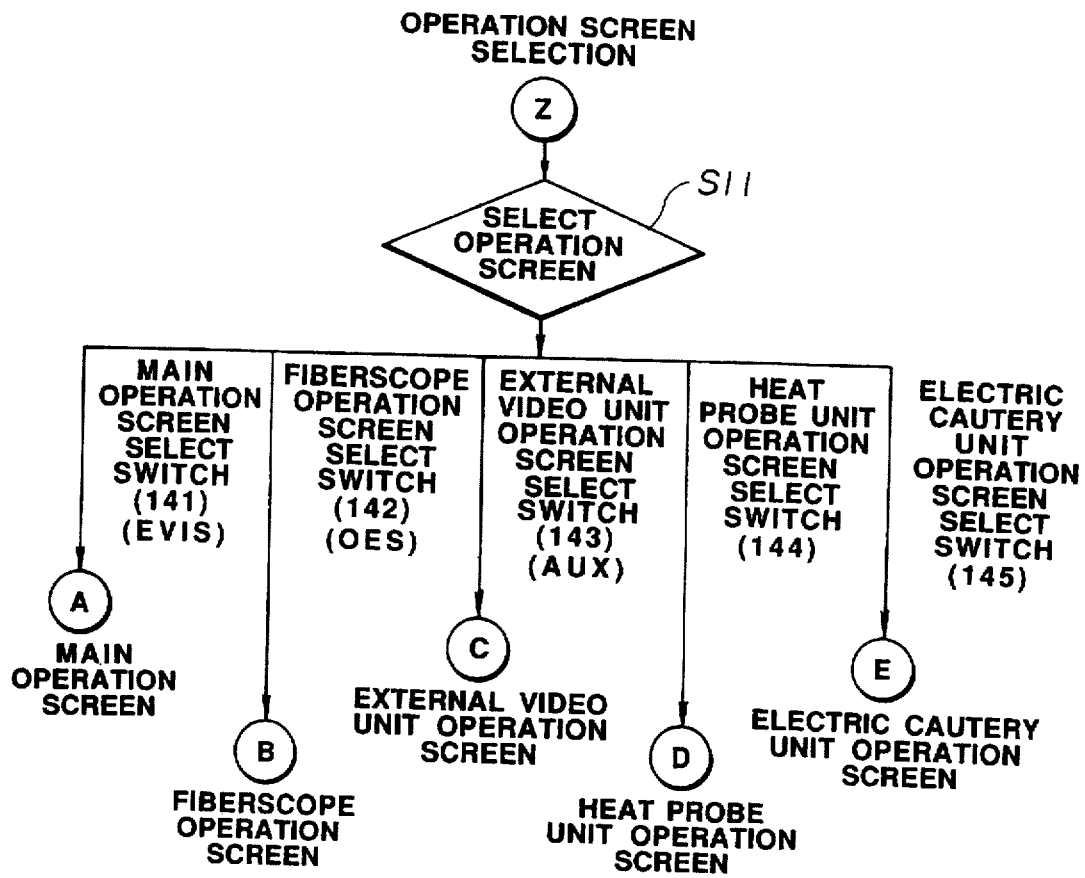
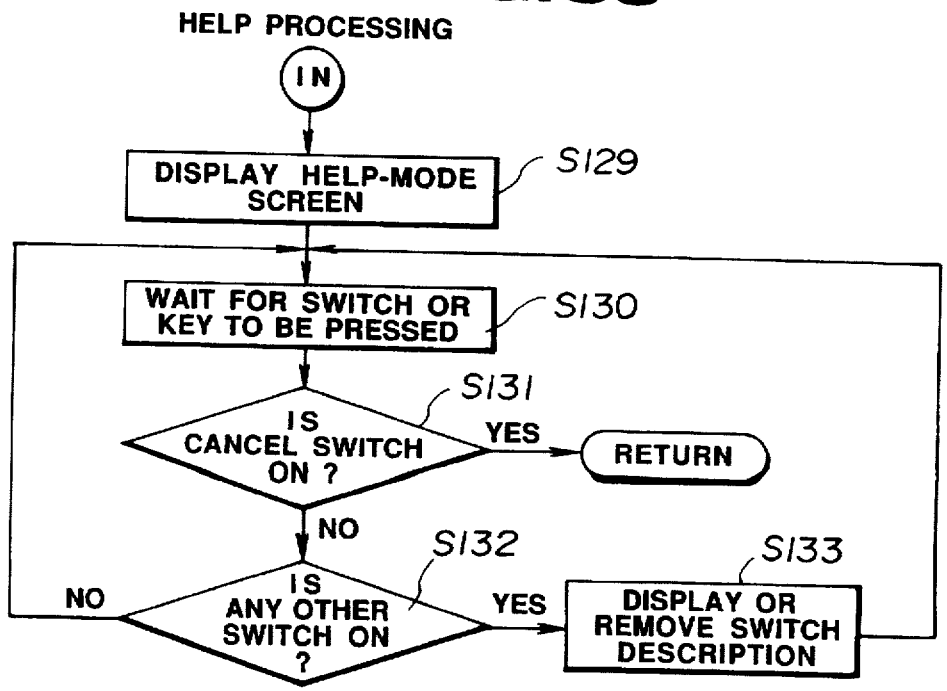

ENDOSCOPE SYSTEM WITH IMPROVED CONTROLLER

This application is a Continuation-in-Part of application Ser. No. 08/051,812, filed Apr. 26, 1993, now abandoned, which was a Continuation of application Ser. No. 07/820,994, filed Jan. 15, 1992, now abandoned.

BACKGROUND OF THE INVENTION

1. Field of the Invention

The present invention relates to an endoscope system having a control apparatus for centralizing control of a plurality of peripheral equipment of the endoscope system such as a light source apparatus.

2. Description of the Related Art

An endoscope, which permits observation of an organ in a cavity when an elongated insertional part thereof is inserted into the cavity, and enables various kinds of treatment procedures when a treatment adapter is, if necessary, routed through a treatment adapter channel thereof, has been widely adopted in recent years. An electronic endoscope with a charge coupled device (CCD) or other solid-state imaging device at the distal part of an insertional part thereof has been put to use.

In the field of medicine, for example, when an endoscope is used to undertake a diagnostic or treatment procedure, it is a common practice that an endoscope system is constructed by mounting an endoscope, a light source apparatus, and other equipment required for use in a rack.

The endoscope system is constructed by combining diverse peripheral equipment according to a purpose of use. The diverse peripheral equipment include a light source apparatus for supplying illumination light to a subject via an endoscope, a video signal processing unit for processing image signals provided by the endoscope, an automatic photography unit for photographing optical images provided by the endoscope, a cautery hemostasis unit for cauterizing a lesion for treatment, and a cautery power supply unit for the cauterization.

Typically, the above peripheral equipment are mounted in a rack or the like to construct an endoscope system. In this case, the equipment are operated independently. In this state, observation or treatment is carried out. Since components are designed to be used independently, they must be operated while being accommodated in the rack or the like. Depending on the design of the rack or the arrangement of units, a doctor or an nurse who operates the endoscope system is obliged to stand at an inconvenient position or walk about for operation. This complicates an operating procedure and causes a failure in realizing an environment most suitable for examination or treatment. For an endoscope system comprising a plurality of peripheral equipment, a function is needed to operate peripheral equipment constituting the system at a single station, centralize the control of multiple equipment, and check the operating states of the multiple equipment at the single station.

The present patent applicant has proposed an endoscope system having a chair equipped with operation switches in U.S. Pat. No. 4,854,301. In the system, the switches on the chair are used to operate equipment. This improves the operability in endoscopic examination or treatment.

However, in the conventional system, although the switches are arranged at easy-to-operate positions, peripheral equipment cannot be operated or controlled on a centralized basis. It is therefore impossible to actuate multiple different equipment or operate them in harmony using a single switch. Moreover, since the operation switches are designed for specific units, the location of an operation unit or the combination of peripheral equipment cannot be altered flexibly.

For centralized control of multiple equipment, quite a number of operation switches must be installed in association with the functions of the multiple equipment. It is typically thought that all the operation switches are integrated into an operating means. However, this arises such drawbacks as: it is hard to install many switches at one place; an increase in the number of switches deteriorates operability; an intended switch is not found immediately because of poor visibility.

OBJECTS AND SUMMARY OF THE INVENTION

An object of the present invention is to provide an endoscope system that displays operation screens associated with functions when operating or controlling the peripheral equipment constituting the system on a centralized basis, and that realizes improvement of operability and prevention of erroneous use.

Another object of the present invention is to provide an endoscope system in which operation screens for use in operating the peripheral equipment constituting the system on a centralized basis are structured hierarchically so that the operation screens can be grouped by specific functions, thus enabling reduction of the number of switches in each operation screen and realizing improvement of the operability and visibility of operation screens.

Yet another object of the present invention is to provide an endoscope system in which operation screens for use in operating the peripheral equipment constituting the system on a centralized basis are structured hierarchically and shifted to any hierarchies, thus enabling prompt display and operation of an intended operation switch and realizing improvement of operability.

Still another object of the present invention is to provide an endoscope system that operates or controls the peripheral equipment constituting the system on a centralized basis, that when it comes to a treatment apparatus designed for treatment, enables input of an operational instruction only when an operation screen associated with the treatment apparatus is on display, and that even when erroneous use occurs, assures safety without deteriorating operability.

The present invention provides an endoscope system comprising a plurality of endoscope system component means including at least one illumination light supply means for supplying illumination light to an endoscope and at least one video signal processing means for processing video signals provided by the endoscope; a main control means for controlling the plurality of endoscope system component means; and a main operational instruction means that is connected to the main control means and operates the plurality of endoscope system component means. Herein, the main operational instruction means includes a display means capable of selectively displaying operational instruction input screens associated with functions of the plurality of endoscope system component means.

Other features and advantages of the present invention will be fully apparent from the description below.

BRIEF DESCRIPTION OF THE DRAWINGS

FIGS. 1 to 15 relate to the first embodiment of the present invention;

FIGS. 1 and 2 are block diagrams showing the configuration of a major section of the first embodiment;

FIG. 3 is a front view of a main unit of an endoscope control apparatus;

FIG. 4 is a plan view of the main unit of a control apparatus;

FIG. 5 is a back view of the main unit of a control apparatus;

FIG. 6 is a right side view of the main unit of a control apparatus;

FIG. 7 is a left side view of the main unit of a control apparatus;

FIG. 8 is a front view schematically showing the main unit of a control apparatus with one of doors open;

FIG. 9 is a schematic oblique view of the main unit of a control apparatus;

FIG. 10 is an explanatory diagram showing a support mechanism for a laptop computer;

FIG. 11 shows an A—A cross section of FIG. 10;

FIG. 13 is a configurational diagram showing an overall configuration of the first embodiment;

FIGS. 14A to 14F are flowcharts showing the contents of the processing performed by a control computer and a laptop computer;

FIGS. 15A to 15J are explanatory diagrams showing screens displayed during the sequences shown in FIGS. 14A to 14F;

FIG. 27 is an explanatory diagram showing a date setting screen for setting a date or the like;

FIG. 38 is a flowchart showing the operations in Operation Screen Selection;

FIG. 53 is a flowchart showing the operations in Help processing;

FIG. 58 is an oblique view showing an overall constitution of an endoscope system;

FIG. 59 is an explanatory diagram showing a main operation screen;

FIG. 60 is an explanatory diagram showing an operation switch layout setting screen for setting the locations of switches in an operation screen;

FIG. 61 is an explanatory diagram showing a scope foot switch setting screen for use in setting the functions of scope switches and foot switches;

FIG. 62 is an explanatory diagram showing a main operation screen;

FIG. 63 is an explanatory diagram showing an operation switch layout setting screen for setting the locations of switches in an operation screen;

FIGS. 67 to 70 relate to the third embodiment of the present invention;

FIG. 67 is an oblique view showing an appearance of en endoscope system in which the configuration of the second embodiment shown in FIG. 16 is implemented;

FIG. 68 is an explanatory diagram showing an internal structure of a doctor workstation;

FIG. 69 is a block diagram showing a configuration of a control system for an endoscope system;

FIG. 71 is an oblique view showing an appearance of an endoscope system; and

FIG. 72 is a block diagram showing a configuration of a control system for the endoscope system.

DETAILED DESCRIPTION OF THE PREFERRED EMBODIMENTS

FIGS. 1 to 5 show the first embodiment of the present invention.

Figure 1:
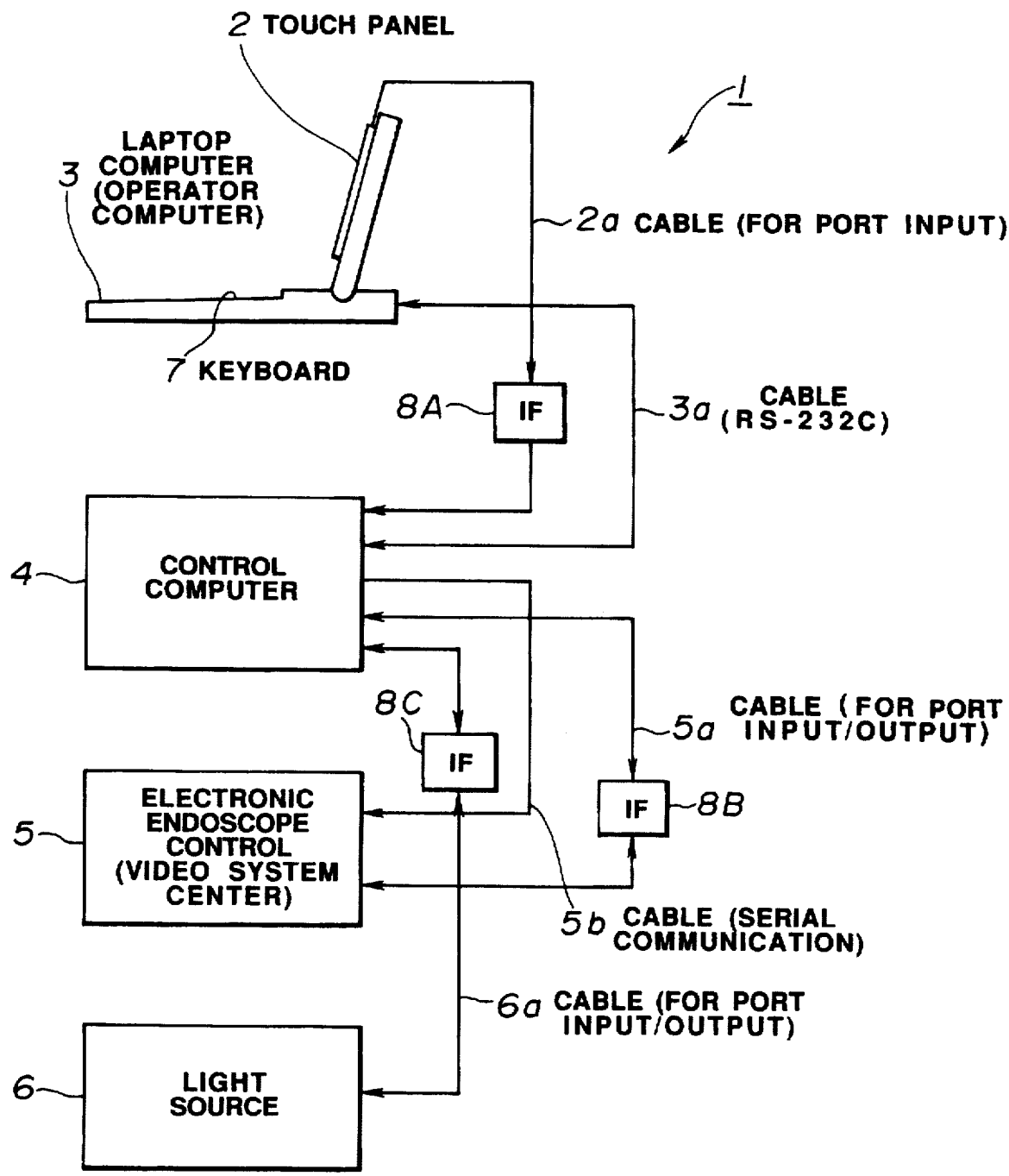
Figure 2:
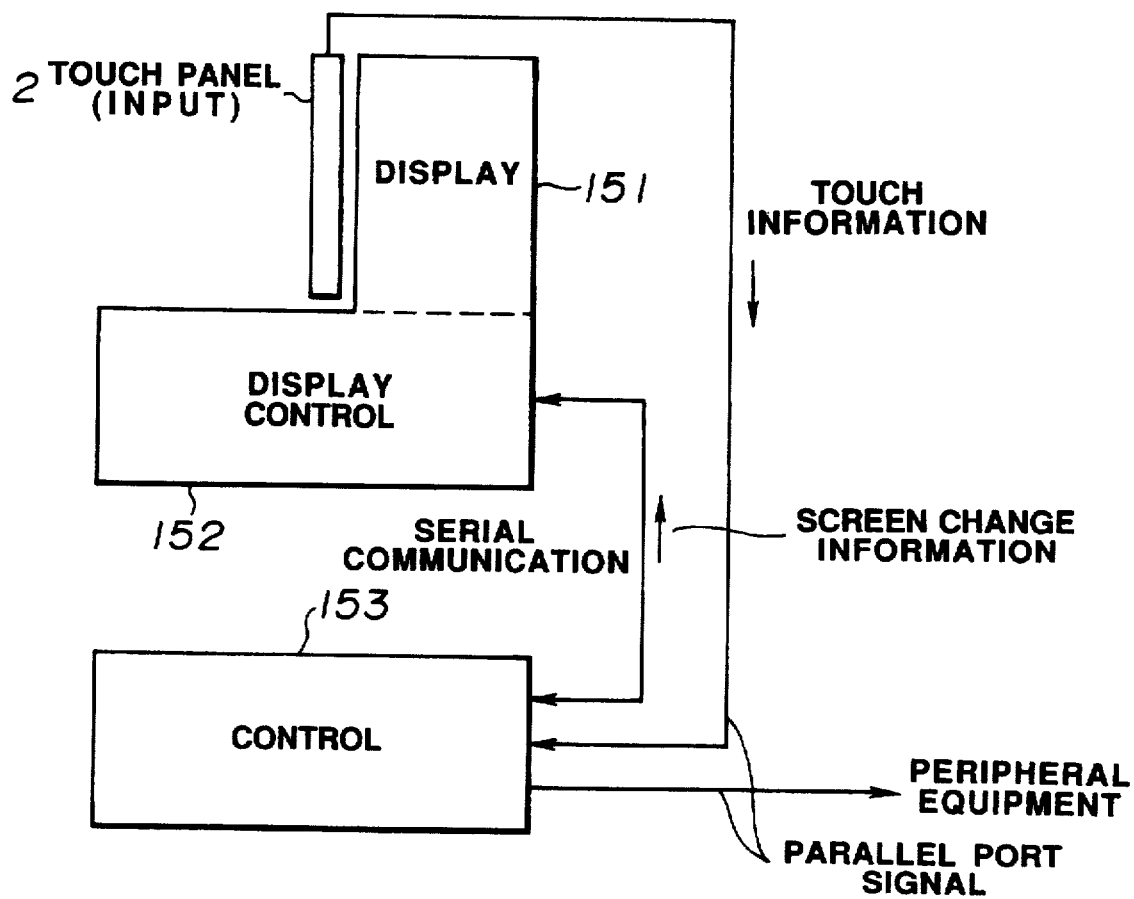

To begin with, the major section of the first embodiment will be outlined in conjunction with FIGS. 1 and 2. Thereafter, a system of the first embodiment will be described in detail.

As shown in FIG. 1, the major section of an endoscope system 1 of the first embodiment comprises a laptop personal computer (operation computer) 3 having a touch panel 2 constituting a centralized operation unit that serves as a main operational instruction means; a control personal computer (control computer) 4 that is connected to the touch panel 2 and operation computer 3 via an interface (I/F) 8A over cables 2a and 3a, and that serves as a main control means for centralizing control or management of component equipment (peripheral equipment) constituting the system 1; an electronic endoscope control unit (referred to as a video system center and abbreviated as VSC) that is a component equipment connected to the control computer 4 via an interface 8B over a cable 5a; and a light source apparatus 6 connected to the control computer 4 via an interface 8C over a cable 6a.

The touch panel 2 comprises transparent electrodes or numerous switches arranged in the form of a matrix. When a scanning means is used to scan the matrix in the x (horizontal) and y (vertical) directions, coordinates are detected to indicate whatever switch or area is pressed. Specifically, the control computer scans the matrix through the I/O ports thereof to detect whatever area on the touch panel 2 mounted in the display screen of the operation computer is pressed (touched), and then reads the data of the coordinates. In other words, the touch detected data and coordinate data are input from the touch panel 2 through the I/O ports of the control computer 4 over the cable 2a. The control computer 4 then transmits a command instructing a change of display screens to the operation computer 3 over the cable 3a. The cable 3a is, for example, conformable with RS-232C, permitting bi-directional data communication.

The operation computer 3 changes display screens in response to the command sent from the control computer 4 (for example, from the VSC 5 control mode to the light source apparatus control mode) or changes own operation modes accordingly. When placed in a mode in which a keyboard 7 is scanned to transmit the scanned data (for example, a data mode), the operation computer 3 transmits the data to the control computer 4. The control computer 4 then converts a key code, which has been entered by operating the keyboard 7 and is sent from the operation computer 3, into a code corresponding to a keyboard command for the VSC 5 (or a command supplied when the operation panel of the VSC 5 is operated), and transmits the converted code into the VSC 5 via the interface 8B for the VSC 5. This transmission is performed over the cable 5a. The cable 5a is used to detect a state of the VSC 5. A cable designed for port input and output is therefore employed as the cable 5a.

Other cable 5b, which is designed for serial communication, transmits TTL signals from the control computer 4 to the VSC 5 and thus enables data input to the VSC 5.

The control computer 4 converts a key code entered by operating the keyboard 7 into a code corresponding to a keyboard command for the light source apparatus 6, and then transmits the converted code into the light source apparatus 6 via the interface 8C. A state of the light source apparatus 6 is also detected by the control computer 4 over the cable 6a.

In the first embodiment, a signal corresponding to a command specified by operating the operation panel of the VSC 5 is produced by the control computer 4 on the basis of a signal sent by operating the touch panel 2 and keyboard 7. The VSC 5 is thus operated as if it were operated by electrically pressing a switch on the operation panel. Specifically, the interface 8B substitutes for the operation panel of the VSC 5. The control computer 4 performs operation control or management depending on the operation of the operation computer 3 equipped with the touch panel 2 in the same manner as that depending on the operation of the operation panel of the VSC 5. The control computer 4 also performs the same operation control or management on the light source apparatus 6. In shorts, the control computer 4 centralizes control or management of the operations of multiple system component equipment.

In the first embodiment, a port output of the control computer 4 is placed on the input lines of the operation panels of component equipment. Control (equivalent to control extended by operating the panel) is thus achieved with an output signal of the control computer 4 without modifying the internal configurations of the component equipment.

As shown in FIG. 2, the operation computer 3 includes a display 151 for centralized operation and a display control unit 152. The touch panel 2 is mounted on the display 151 and used as an input unit. The display control unit 152 is connected to the control computer 4 serving as a control unit 153 for centralizing control of peripheral equipment over a serial cable. The control unit 153 is connected to the touch panel 2 and peripheral equipment via parallel interfaces.

In response to an instruction sent from the control unit 153, screen change information for centralized operation is transmitted to the display control unit 152 by serial communication. Based on the screen change information, the display control unit 152 changes screens of the display 151. That is to say, operational screen displays are changed depending on the control mode. When a given area on the touch panel 2 corresponding to a screen display is pressed, touch information is input to the control unit 153. It is then detected that an operational input for a peripheral equipment is entered. The control unit 153 not only transmits screen change information as mentioned above but also produces control signals for peripheral equipment and transmits the signals to the peripheral equipment.

According to the first embodiment, even when the number of component equipment of the endoscope system 1 increases, the equipment can be operated on a centralized basis at the touch panel 2 and keyboard 7 which are commonly employed. Even when component equipment are distributed here and there, operational sections thereof can be operated at a single place. A user-friendly system can therefore be constituted. (In the first embodiment, major component equipment which are used frequently are operated on a centralized basis.)

The operation computer 3 is used as a man-machine interface, which enables implementation of software in the form of a module and permits free composition of input screens. Display screen information for centralized operation is contained in the display control unit 152 in the operation computer 3. The memory in the control computer 4 (control unit 153) is therefore not consumed.

Different computers are used for man-machine interface and control respectively. Software packages can therefore be developed independently. The display control unit 152 is used to visualize screens, which contributes to reduction of a load to the software implemented in the control unit 153.

Next, the configuration of the endoscope system 1 of the first embodiment will be described specifically in conjunction with FIGS. 3 and later.

Figure 9:
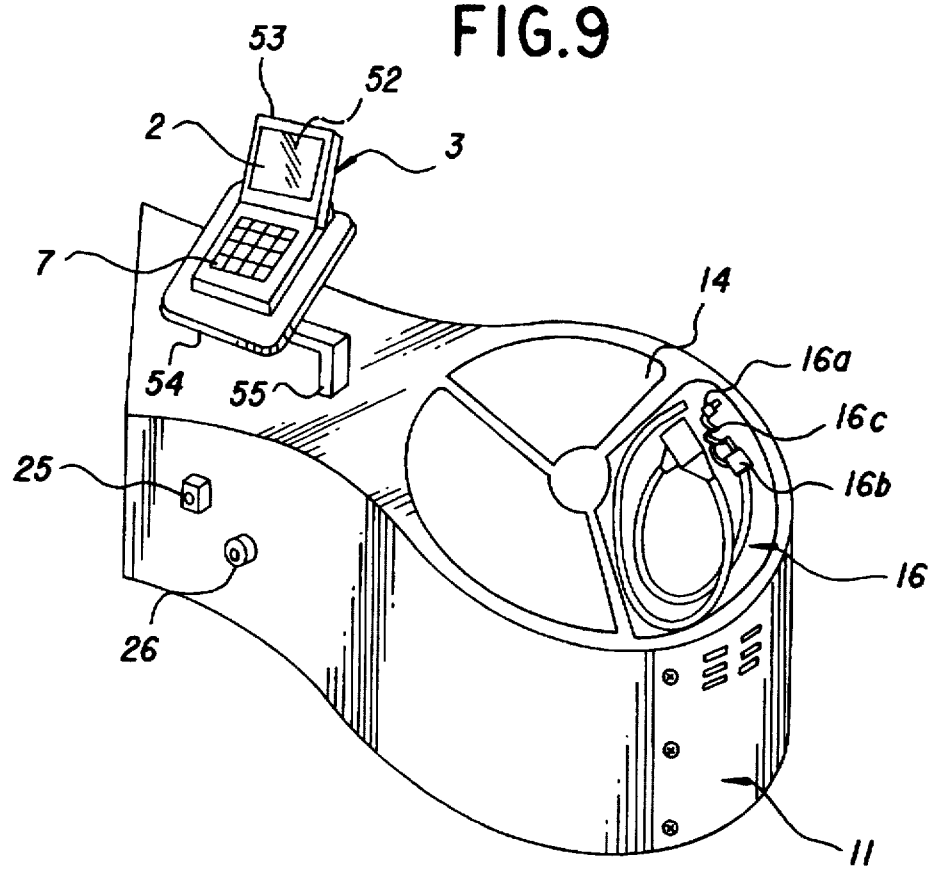

As shown in FIGS. 3 to 7, the endoscope system 1 of the first embodiment comprises a main unit 11 of a control apparatus, a monitor 13 mounted on an arm 12 extending from the main unit 11 of a control apparatus, an operation computer 3 mounted on the top of the main unit 11 of a control apparatus so as to be freely rotatable, a circular tray 14 mounted on the top of the main unit 11 of a control apparatus, and an endoscope employed, for example, an electronic endoscope 16 (See FIG. 9). A scope hanger 15 can be mounted on the main unit 11 of a control apparatus so as to be dismounted freely. As shown in FIG. 9, the electronic endoscope 16, treatment adapters, and other accessories, which are employed for endoscopic procedures but not shown, can be placed on the tray 14. The tray 14 is mounted on the top of the main unit 11 of a control apparatus.

Figure 4:
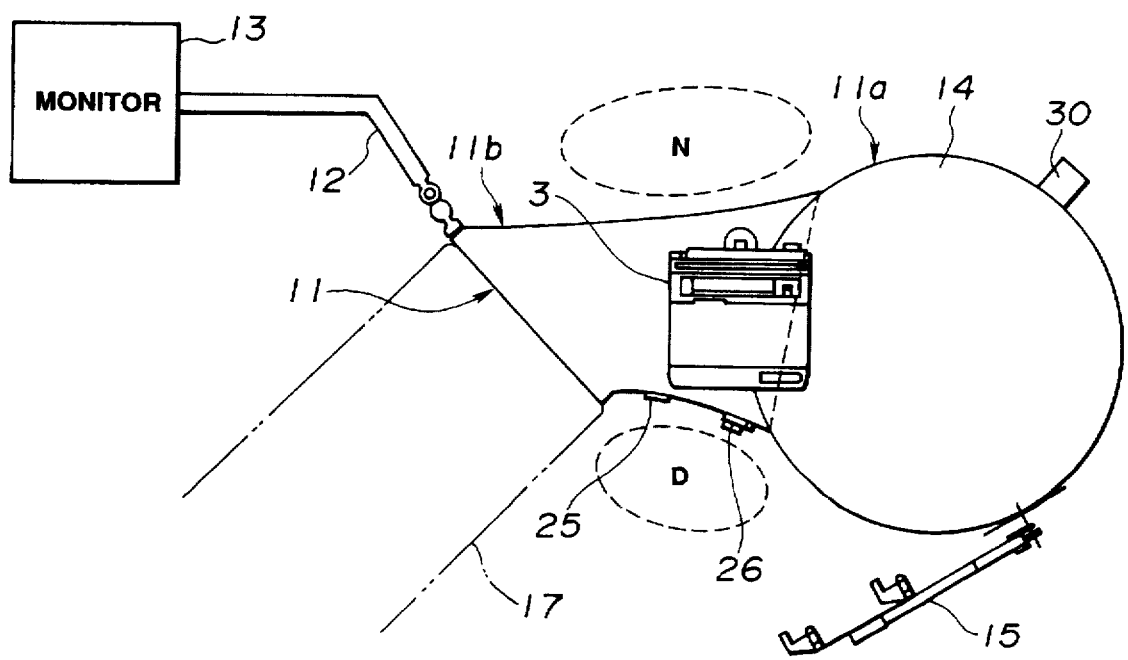

As shown in FIG. 4, the main unit 11 of the control apparatus comprises a columnar section 11a and a deformed square-pole section 11b coupled to the columnar section 11. A bed 17 is arranged so that one end thereof will be aligned with the inclined plane on the external end of the deformed square-pole section 11b. The main unit 11 of a control apparatus is designed so that a position D facing the front of the deformed square-pole section 11b will be a position suitable for a doctor or a primary user to operate the system, and a position N in the back of the deformed square-pole section 11b will be a position suitable for a nurse or a secondary user to operate the system. The width of the deformed square-pole section 11b between the front and back faces thereof is designed to be substantially two-thirds or less of the diameter of the columnar section 1a or to be 50 cm or less.

Figure 3:
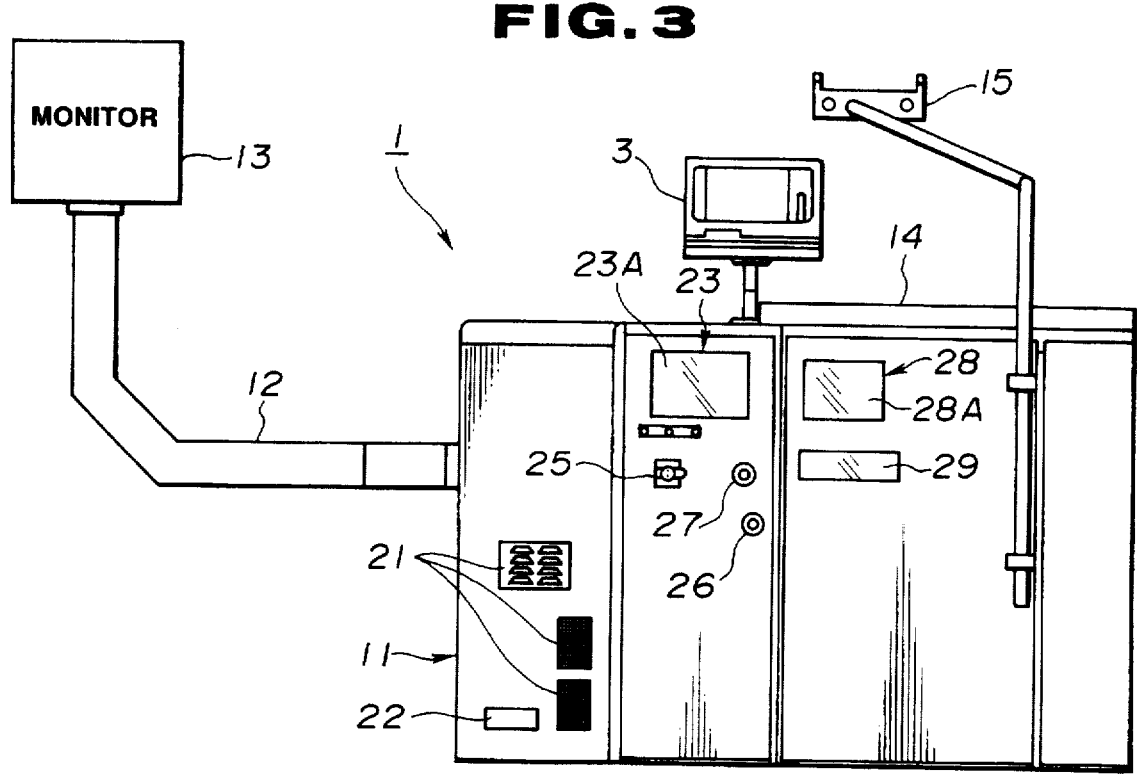

As shown in FIG. 3, on the front face of the main unit 11 of the control apparatus, a duct 21, and a connector unit 22 including a foot switch connector, a P-plate connector, and a service socket are arranged on the inclined plane of the deformed square-pole section 11b facing the bed 17. A heat probe unit 23 for controlling a hemostatic procedure based on heating coagulation is installed in the upper part of the deformed square-pole section 11b. The main panel 23A of the heat probe unit 23 is coming out of the hollow opening onto the front face of the deformed square-pole section 11b which is opposed to a doctor. The endoscope light source connector receptacle 25 and signal connector hanger 27 of the light source apparatus, which is not shown, are arranged below the main panel 23A. A fiberscope used as an endoscope or a light source connector for an electronic endoscope are plugged into the light source connector receptacle 25, and a signal connector for an electronic endoscope is plugged into the signal connector receptacle 26. An electric cautery unit 28 is installed in the upper part inside the columnar section 11a, and a TV camera control unit (hereinafter, abbreviated as CCU) is installed under the electric cautery unit 28. The main panel 28A of the electric cautery unit 28 and the panel of the CCU 29 are exposed outside through two hollows opening onto the front face of the columnar section 11a. A TV camera to be mounted in the eyepiece unit of the fiberscope is connected to the CCU 29.

Figure 5:
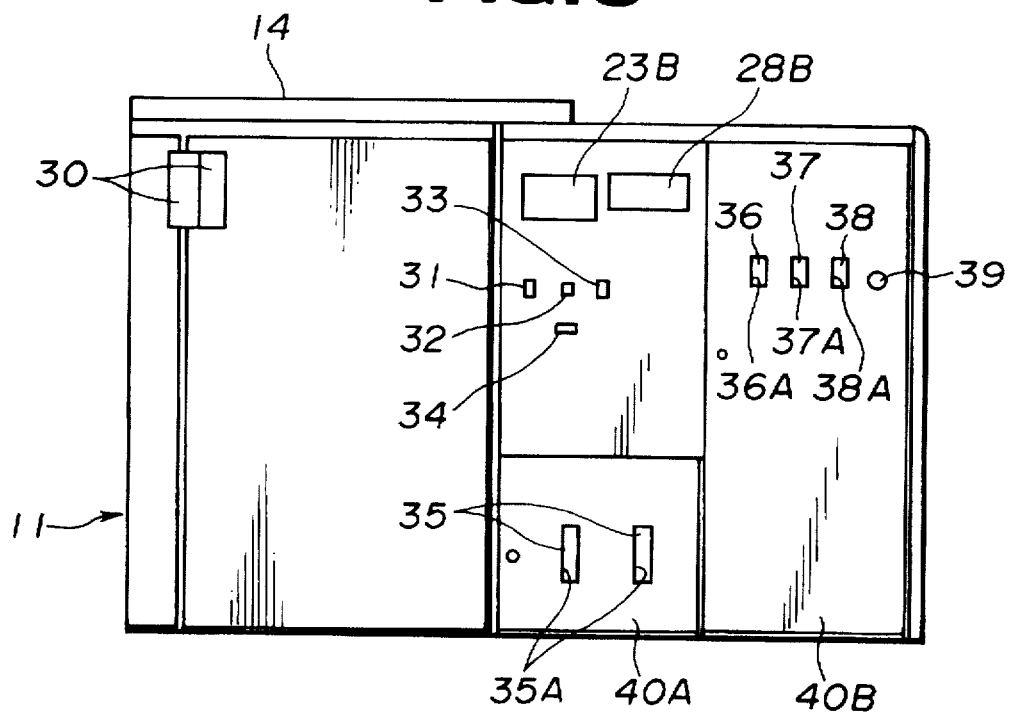

As shown in FIG. 5, on the back face of the main unit 11 of a control apparatus, a subpanel 23B of the heat probe unit 23 is installed in the upper left part of the back face of the deformed square-pole section 11b, and a subpanel 28B of the electric cautery unit 28 is installed on the right of the subpanel 23B. Below the panels 23B and 28B, a power switch 31, an ignition switch 32, an aspirator switch 33, and a lamp life meter 34 are arranged, and aspirator containers 35 are coming out. On the right side of the switches 31 to 33, a treatment adapter water container 36, a water container 37, and a simplified cleaning water container 38 are exposed outside, and an oral suction tube 39 is installed. An input/output line 30 serving as an input/output terminal for inputting or outputting image data is installed on the back face of the columnar section 11. Openings 35A, 36A, 37A, and 38A, which are large enough to check the quantities of fluid in the aspirator containers 35, treatment adapter water container 36, water container 37, and simplified cleaning water container 38, are formed on the wall in the vicinities of these containers.

Figure 6:
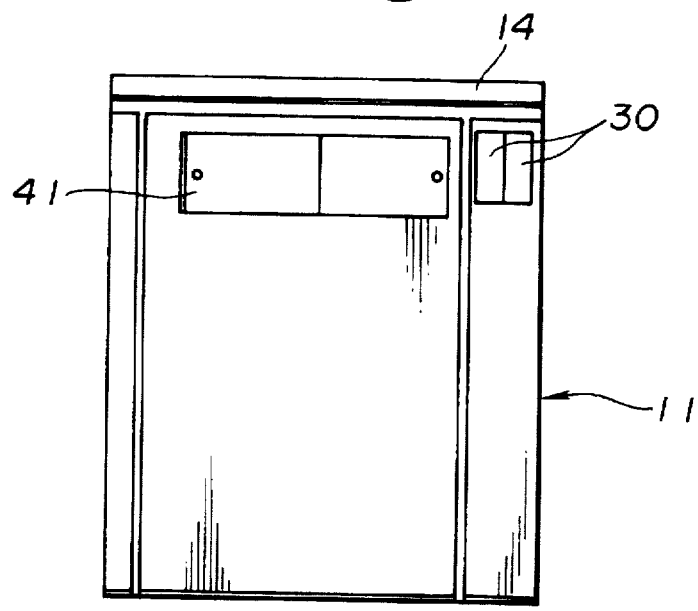
Figure 7:
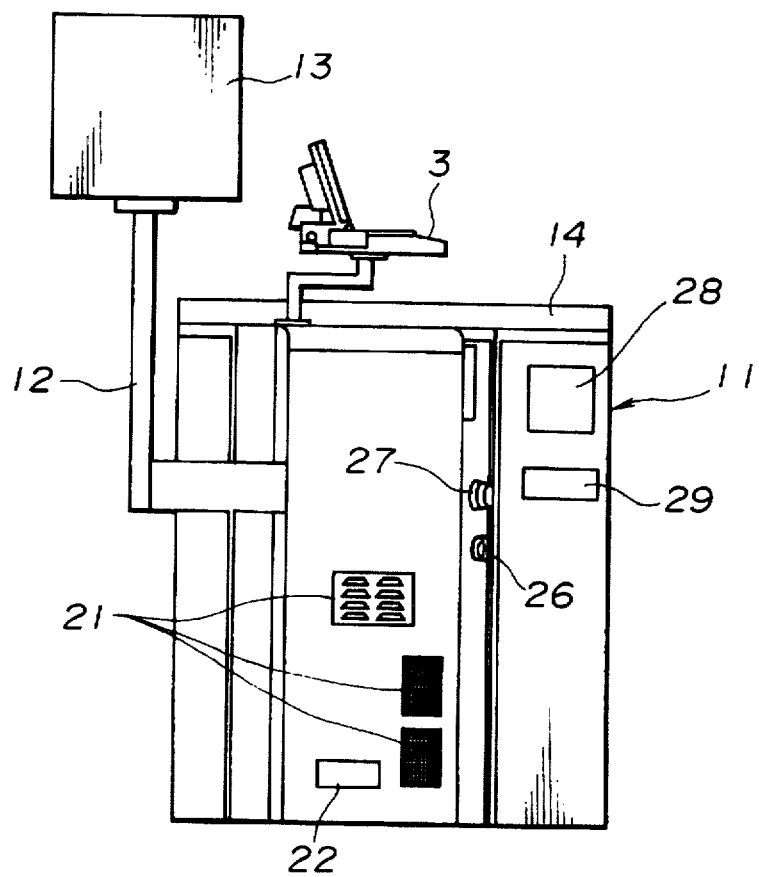

A photography unit 41 is accommodated in the cover of the right side of the main unit 11 of a control apparatus shown in FIG. 6.

Figure 8:
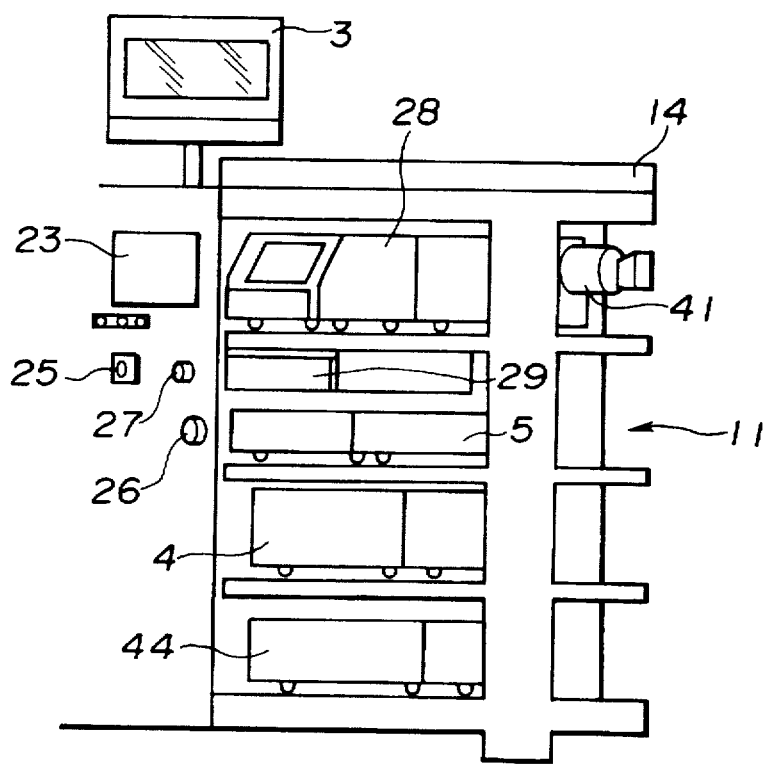

When part of the front cover of the main unit 11 of the control apparatus is removed, as shown in FIG. 8, the electric cautery unit 28, TV camera CCU 29, electronic endoscope VSC 5, control computer 4, and power supply 44 for the light source apparatus are seen lying. The light source apparatus 6 is mounted under the heat probe unit 23 on the left of the main unit 11 of the control apparatus. A cooling unit is placed under the light source apparatus 6.

As shown in FIG. 9, the laptop computer 3 serving as an operation unit of the endoscope system 1 is placed on the top of the main unit 11 of a control apparatus so as to be freely rotatable.

Figure 10:
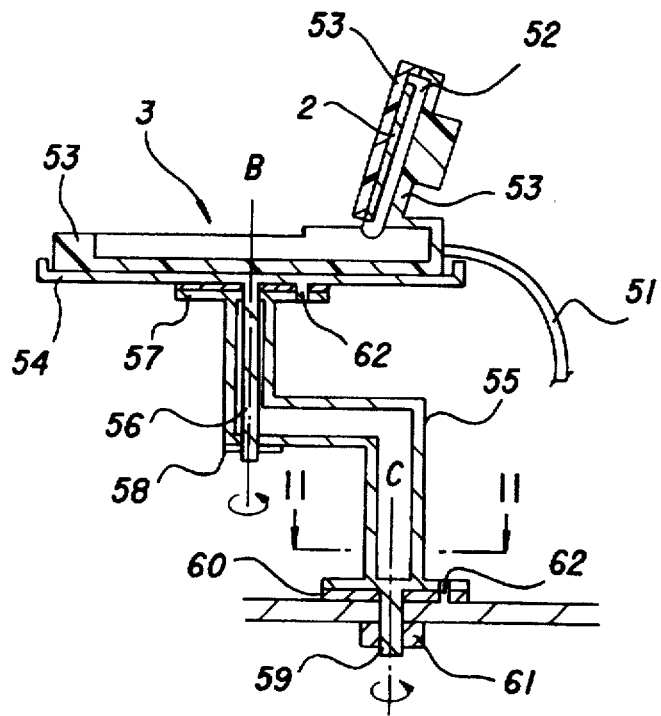

As shown in FIG. 10, the operation computer 3 is, as mentioned above, provided with the touch panel 2 on the front face of the display screen, and electrically coupled with the control computer 4 in the main unit 11 of a control apparatus over a cord 51. The bottom and surrounding areas of the main unit of an operation computer as well as the back face and surrounding areas of the display 52 are shielded with a cover member 53 such as plastic, so that when the touch panel 2 is pressed to operate the touch panel 2, the display 52 made of liquid crystal will not be turned down. The cover member 53 holds the display 52 at an angle permitting easy view of display screens.

The computer 3 is mounted on a table 54. The table 54 is attached to an axis 56 which is freely rotatable with respect to the a pipe member 55. As shown in FIG. 10, the table 54 is freely rotatable with the axis 56 or a character B as a center. Reference numeral 57 denotes a sliding friction plate, and reference numeral 58 denotes a stopper pin.

The pipe 55 is shaped like a character L. An axis 59 is formed at the proximal end of the pipe 55. The pipe 55 is fitted into the recess on the top of the main unit 11 of a control apparatus via a sliding friction plate 60, and secured with a nut 60 so as not to come off. The pipe 55 is freely rotatable about an axis 39 or a character C. The table 52 is therefore structured to be freely rotatable with the characters B and C as centers. This allows a doctor and a nurse alike to rotate the table 54 and operate the computer 3 easily.

Figure 11:
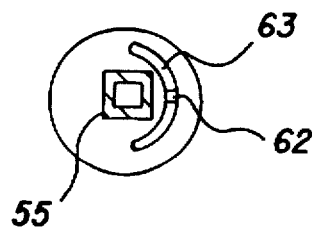

As shown in FIG. 11, a projection 62 is projecting from the top of the main unit 11 of a control apparatus. The projection 62 is fitted into a semicircular groove 63 formed on the flange near the proximal end of the pipe member 55. The axis 59 is thus prevented from rotating beyond a half turn, because when the axis 59 rotates a full turn, the cord 51 will be tangled. The same structure applies to the axis 56.

As mentioned previously with reference to FIG. 1. the operation computer 3 and touch panel 2 are connected to the control computer 4 in the main unit 1 of a control apparatus. The control computer 4 is connected to the electronic endoscope VSC 5 and light source apparatus 6. The light source apparatus 6 is interchangeable among three modes in which an electronic endoscope is used, a fiber scope is used, and a TV camera is mounted on the fiberscope (the operation can be controlled using the control computer 4).

As apparent from FIGS. 3 and 9, the light source connector receptacle 25 is horizontally separated from the signal connector receptacle 26 so as to lie diagonally above the signal connector receptacle 26. A light source connector 16b of the endoscope 16 shown in FIG. 9 is plugged in the light source connector receptacle 25. A signal connector 16a at the distal end of a connection cable 16c is plugged in the signal connector receptacle 26.

Figure 12A:
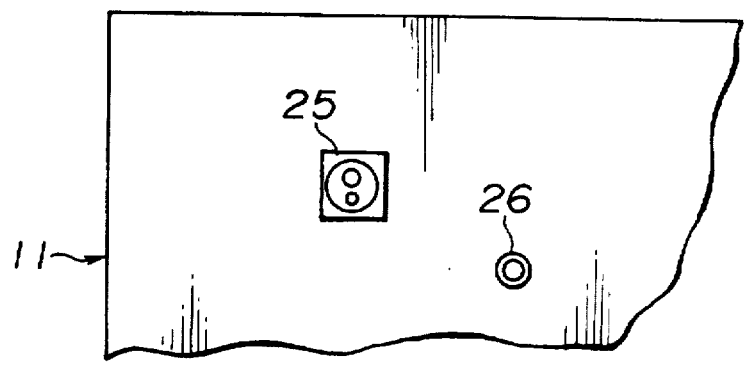
FIGS. 12A, 12B, and 12C are front views showing the positional relationships between a light source connector receptacle and a signal connector receptacle.
Figure 12B:
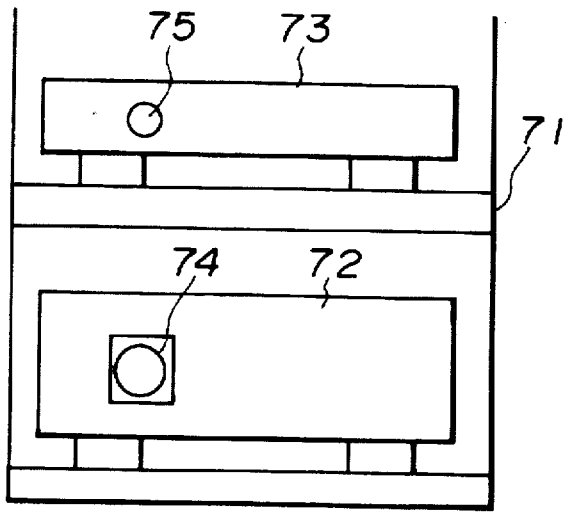
Figure 12C:
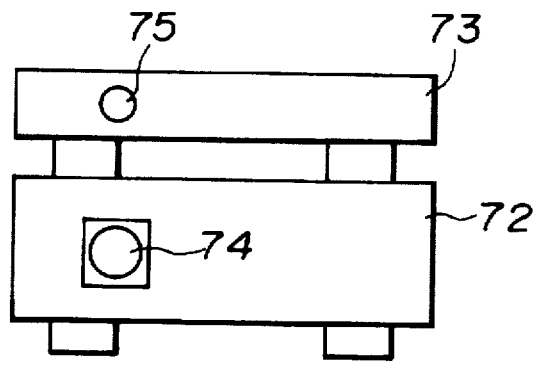

FIG. 12a is an enlarged view showing the positional relationships between the light source receptacle 25 and signal connector receptacle 26. FIGS. 12b and 12c show a prior art for comparison. In FIG. 12b, a light source apparatus 72 and a VSC 73 are mounted up and down in a shelf 71. A light source connector receptacle 74 and an electronic endoscope signal connector receptacle 75 are positioned up and down along a vertical line.

In the prior art shown in FIG. 12c, the light source apparatus 72 and VSC 73 are stacked up and down. The light source connector receptacle 74 and signal connector receptacle 75 are positioned up and down along a vertical line.

In this embodiment, as shown in FIG. 12a, the light source connector receptacle 25 and electronic endoscope signal connector receptacle 26 are positioned on the diagonal. This provides the advantages (effects) below.

In the prior art, assuming that scopes are changed, when an attempt is made to plug the signal connector 16a into the signal connector receptacle 26, the connection cable 16c extending from the light source connector 16b dangles by the light source connector receptacle 25 and interferes with the plugging of the signal connector 16a of a scope 16 into the signal connector receptacle 26. In this embodiment, even when the connection cable 16c dangles, it will neither come close to the signal connector receptacle 26 nor interfere with connection. The connection can therefore be achieved smoothly. The connection cable 16c will not disturb an operator's hand. Moreover, the connection cable 16c is hardly stressed, preventing disconnection of a signal conductor therein. Furthermore, a scope can be attached or detached more easily by a left hand. When disconnected, the connection cable 16c extending from the scope does not dangle nearby. When scopes are to be changed, if the connection cable 16c is disconnected first, even an S cord or a suction tube can be detached more easily.

Figure 13:
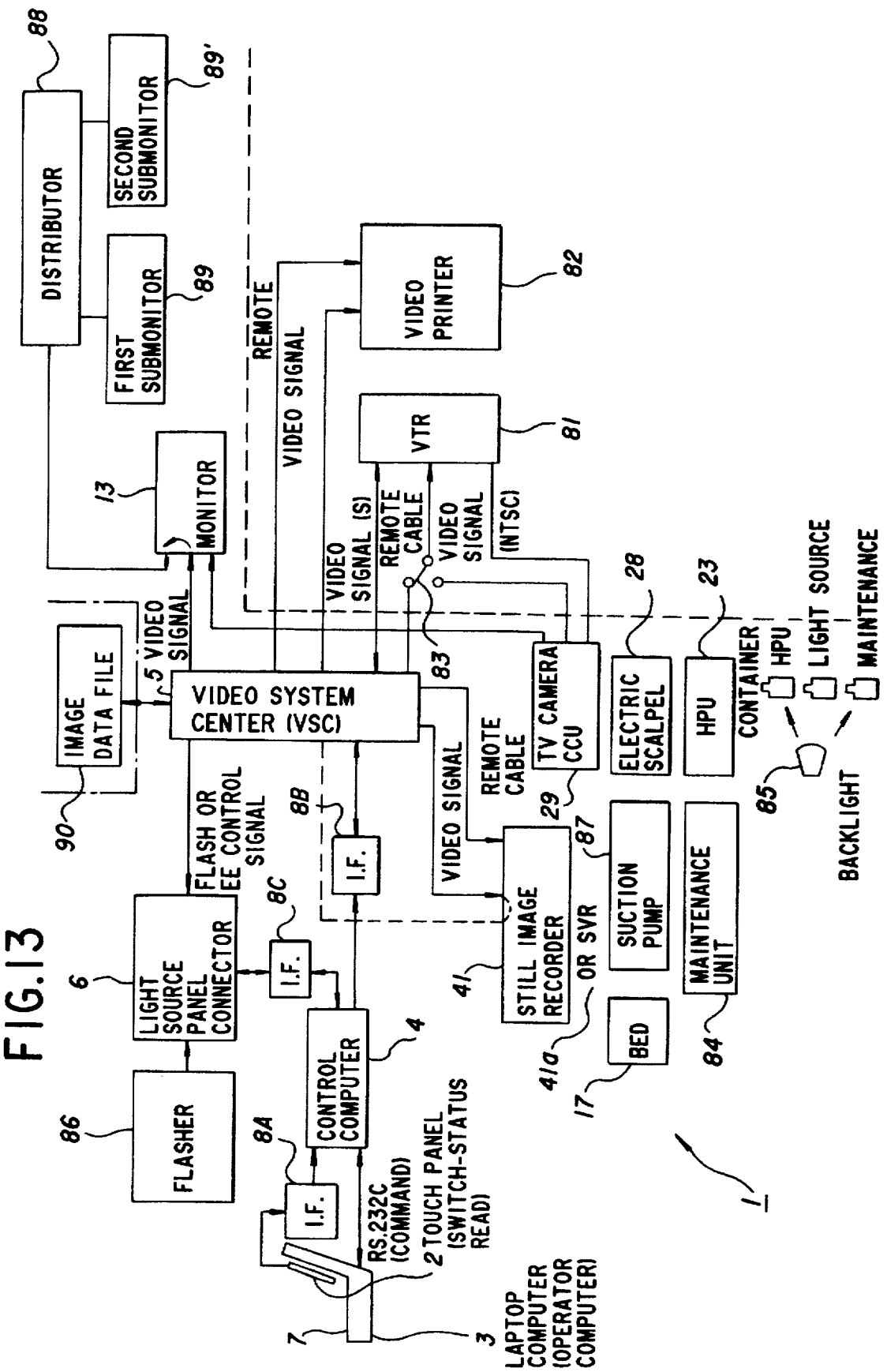

FIG. 13 shows an overall configuration of the first embodiment.

The left part of FIG. 13 beyond a dotted line includes component equipment (except the bed 17) accommodated or mounted in the main unit 11 of a control apparatus. The right part thereof includes satellite equipment used in connection with the main unit 11 of a control apparatus.

As described previously, the touch panel 2 consisting of transparent electrodes is affixed to the liquid crystal panel of the operation computer 3. The states of the switches on the touch panel 2 are read by the control computer 4.

In response to a command from the control computer 4, the operation computer 3 reads graphics on the back of the touch panel 2. In response to a request from the operation computer 3, the control computer 4 transmits the states of all switches. With power on, the operation computer 3 requests the control computer 4 for switch states. On the other hand, the control computer 4 stores current states of switches in a hard disk thereof. With power on, the display screen of the operation computer 3 has the contents associated with the states of switches which have been set with power off.

The control computer 4 is accommodated in the main unit 11 of a control apparatus. The main unit 11 of a control apparatus has a relatively large storage space and can accommodate a large personal computer or other computer. However, a bulky operation computer will be an obstacle. In the first embodiment, therefore, a laptop computer is employed as an operation computer in terms of space-saving (needless to say, not only a laptop computer but also other light-weight computer can be employed).

The VSC 5 and light source apparatus 6 are connected to the control computer 4 by installing the interfaces 8B and 8C on, for example, the operation panels of the front faces thereof.

As shown in FIG. 13, the VSC 5 can be connected to peripheral video equipment; such as, a still image photography unit 41 (or a still video recorder SVR 41a) accommodated in the main unit 11 of a control apparatus, an external VTR 81, and a video printer 82. These peripheral equipment are controlled by the VSC 5 via remote cables. The VSC 5 is controlled by the control computer 4. The control computer 4 therefore controls video equipment indirectly. The VSC 5 thus controls the peripheral equipment, which obviates the need of creating new control programs.

The video printer 82 fetches video signals from the still image photography unit 41 when the still image photography unit 41 is connected. When the SVR 41a is connected, video signals are fetched from the SVR 41a.

A TV camera CCU 29 is incorporated in the main unit 11 of a control apparatus, and controls the VTR 81 using a switch 83 that can be turned on or off manually.

The light source apparatus 6 and VSC 5 are always placed in the same states with power on. With power on, the switches are set as specified in backup data existent in the hard disk of the control computer 4. This is because when the backup batteries of the VSC 5 and light source apparatus 6 are used, if switch states differ from those in the control computer 4 due to noises or the like, the differences may persist permanently. To prevent this, the backup data is used.

Figure 14A:
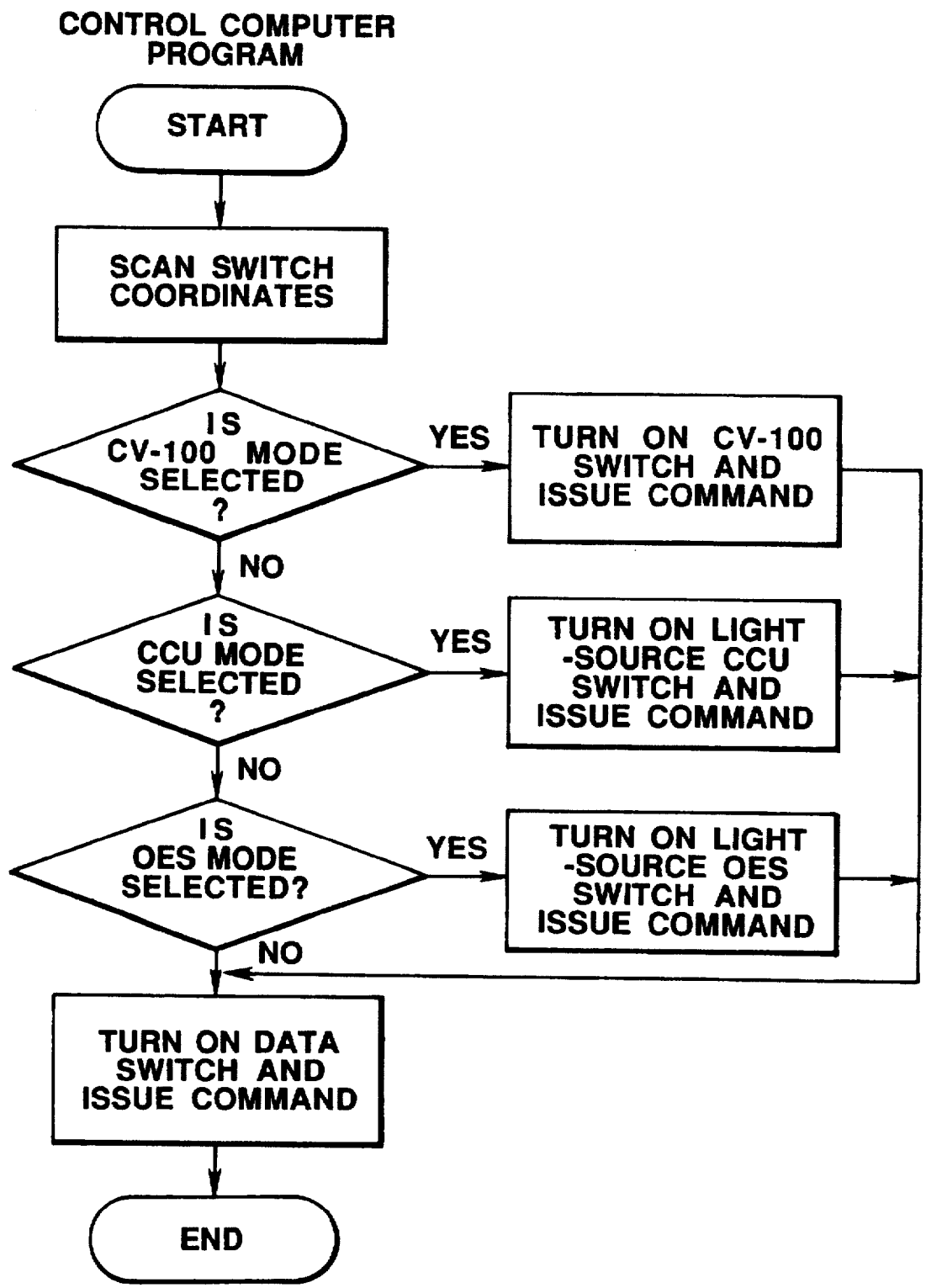

In the first embodiment, the control computer operates according to the flow shown in FIG. 14A, while the operation computer 3 operates according to the flow shown in FIGS. 14B, 14C, 14D, and 14E.

During the processing shown in FIGS. 14A to 14E, the display screen of the operation computer 3 represents operational instruction input screens shown in FIG. 15A to 15J.

In FIGS. 14A to 14E and 15A to 15J, CV-100 denotes an electronic endoscope VSC. The CV-100 mode represents a control mode for the VSC with an electronic endoscope connected. The CCU or light source CCU mode represents a control mode for the light source apparatus 6 with an electronic endoscope connected. The OES mode represents a control mode for the light source apparatus 6 with a TV camera mounted on a fiberscope (OES).

As shown in FIG. 14A, the control computer 4 scans the switch coordinates of the touch panel 2, and determines in which mode the touch panel 2 is operated: CV-100, CCU, or OES mode. Based on the determination, switching and command transmission are performed on equipment.

When neither the CV-100, CCU, nor OES mode is set, it is determined that the data mode is selected. Switching and command transmission are performed on the operation computer 3.

Figure 14B:
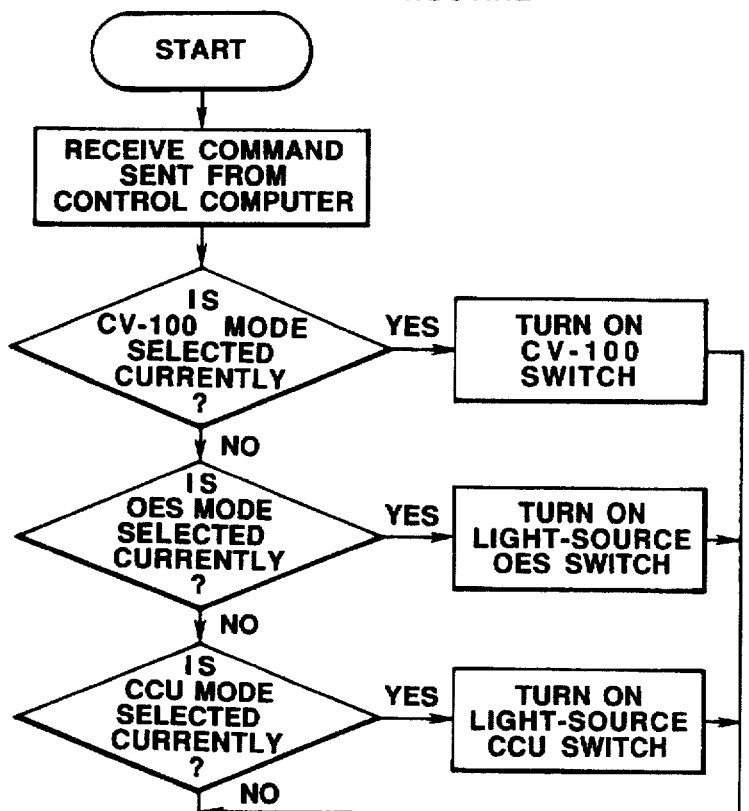

FIG. 14B shows a screen change routine.

In response to a command from the control computer 4, the operation computer 3 determines which mode is selected currently and performs switching on the equipment associated with the current mode. When the current mode is neither of the above three modes, the operation computer 3 operates on the assumption that the data mode is selected.

Figure 14C:
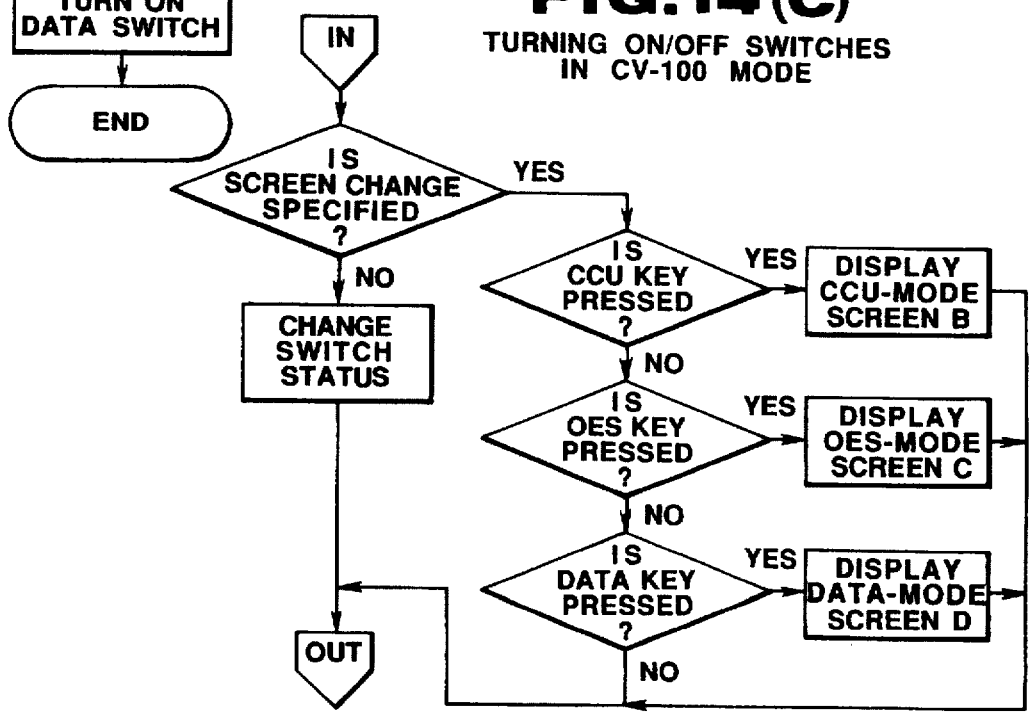
Figure 14:
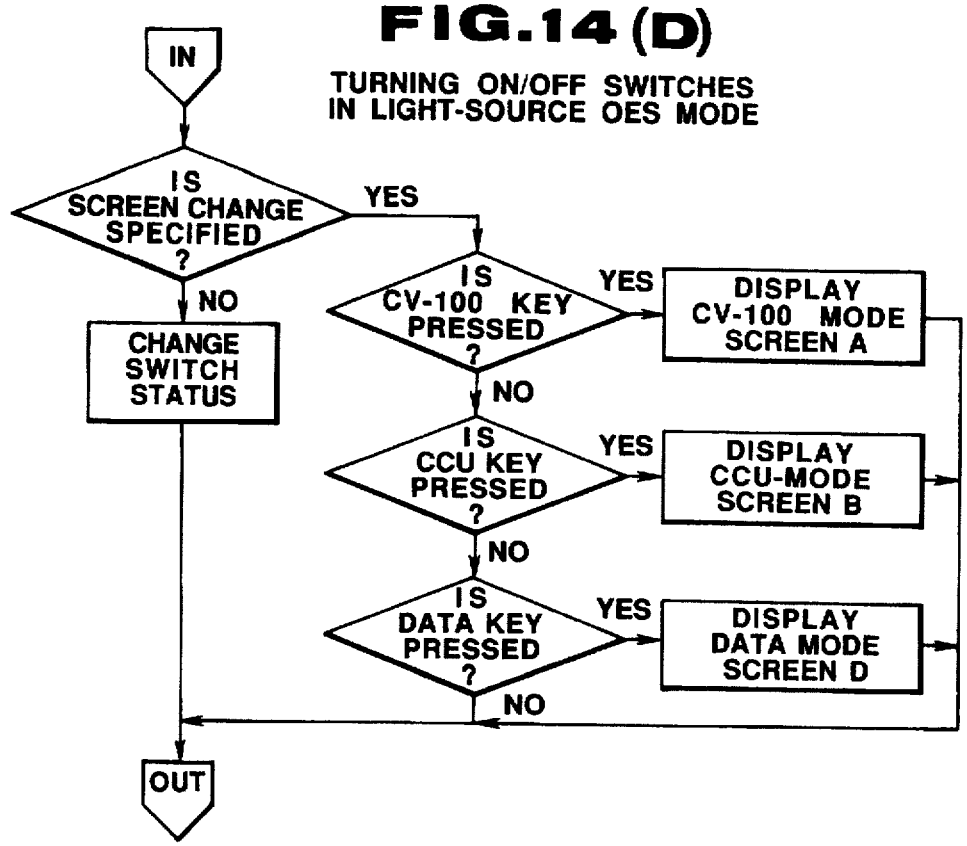
Figure 14:
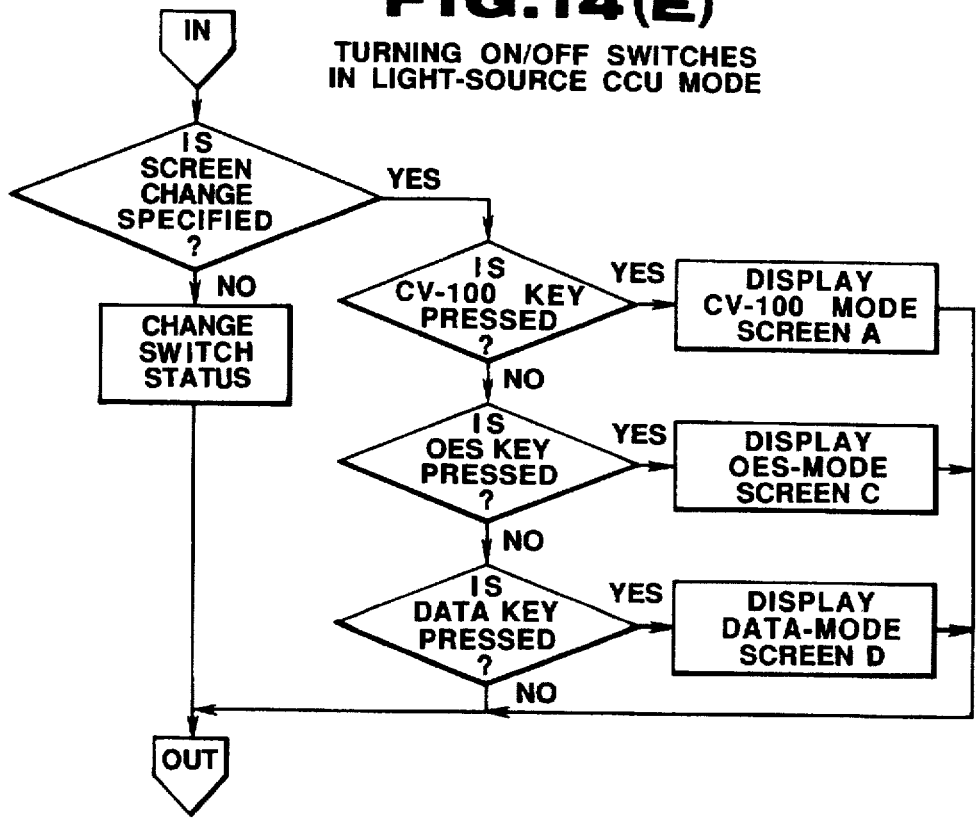

FIGS. 14C, 14D, and 14E show the contents of switching in the CV-100, OES, and CCU modes respectively.

In FIG. 14C, for example, it is determined that an input command specifies screen change. If it is determined that the command is a screen change command, it is determined which key is pressed: the CCU key, OES key, or Data key. The screen of the determined mode is then displayed. For example, when it is determined that the CCU key is pressed, the screen shown in FIG. 15B is displayed. When it is determined that the OES key is pressed, the screen shown in FIG. 15C appears. When it is determined that the Date key is pressed, the screen shown in FIG. 15D appears.

In FIG. 14C, if it is determined that screen change to any mode is specified, the states of switches are changed in the CV-100 mode. The data-mode processing shown in FIG. 14B is performed.

Figure 15A:
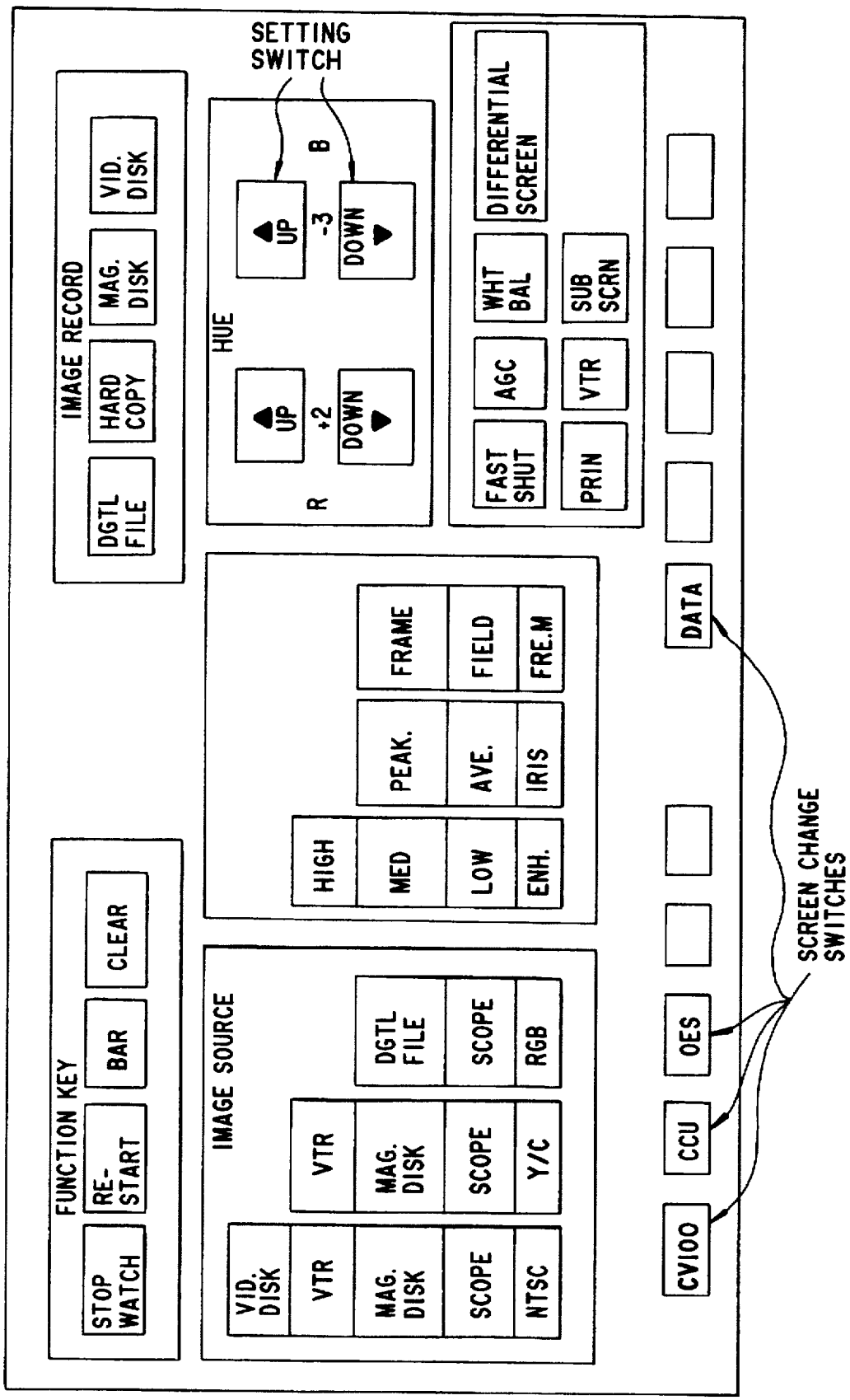
Figure 15:
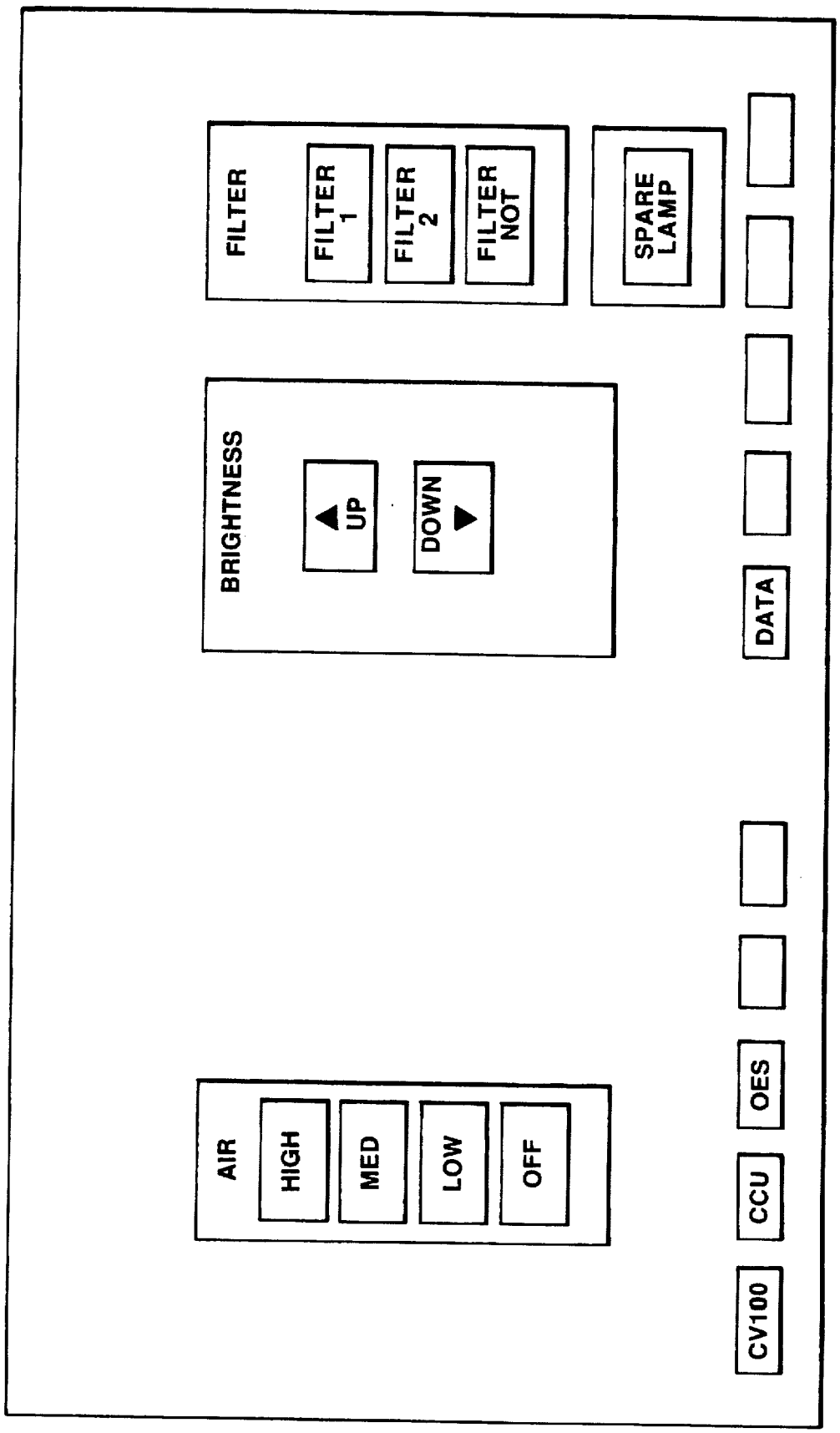
Figure 15C:
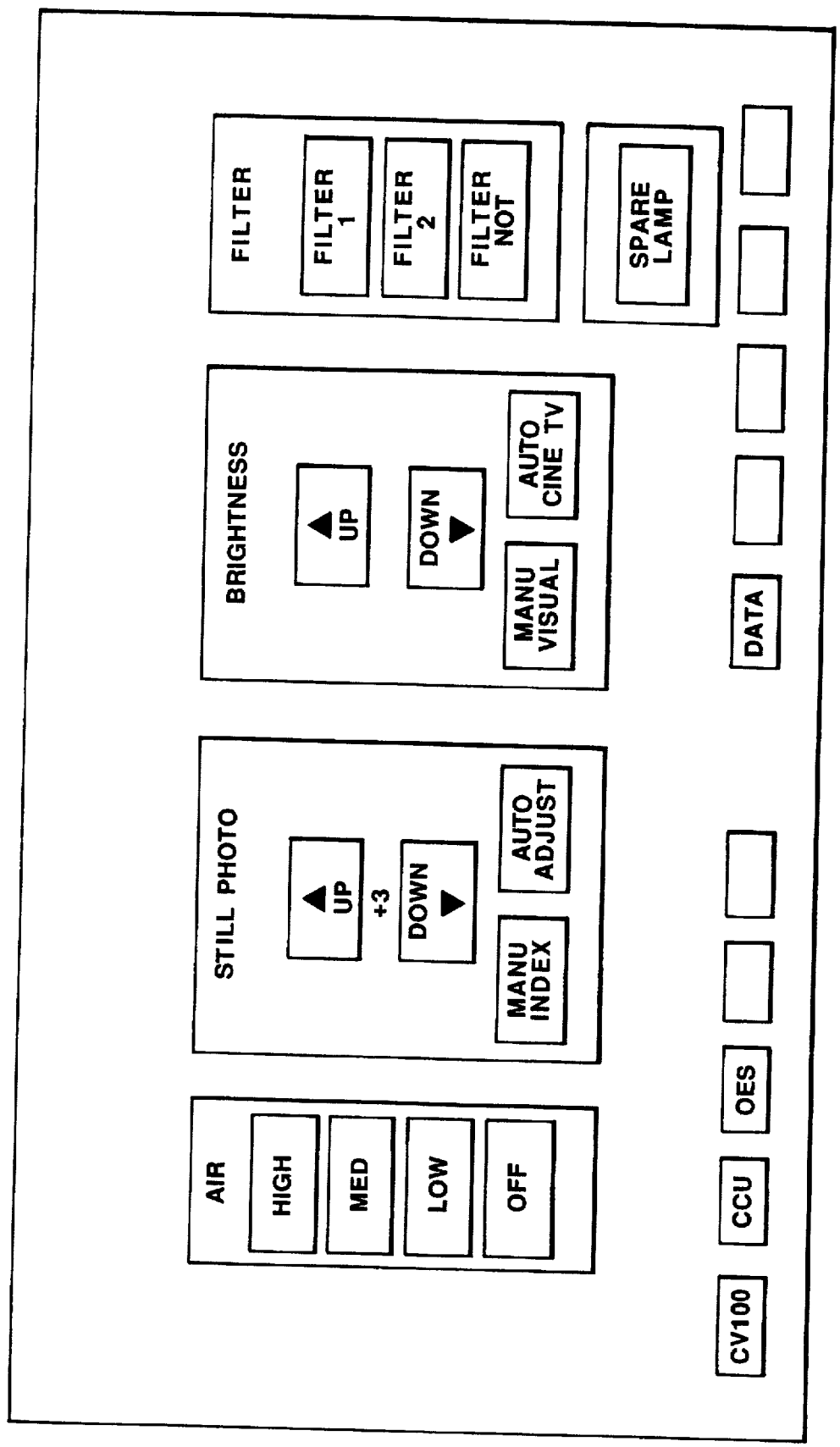
Figure 15D:
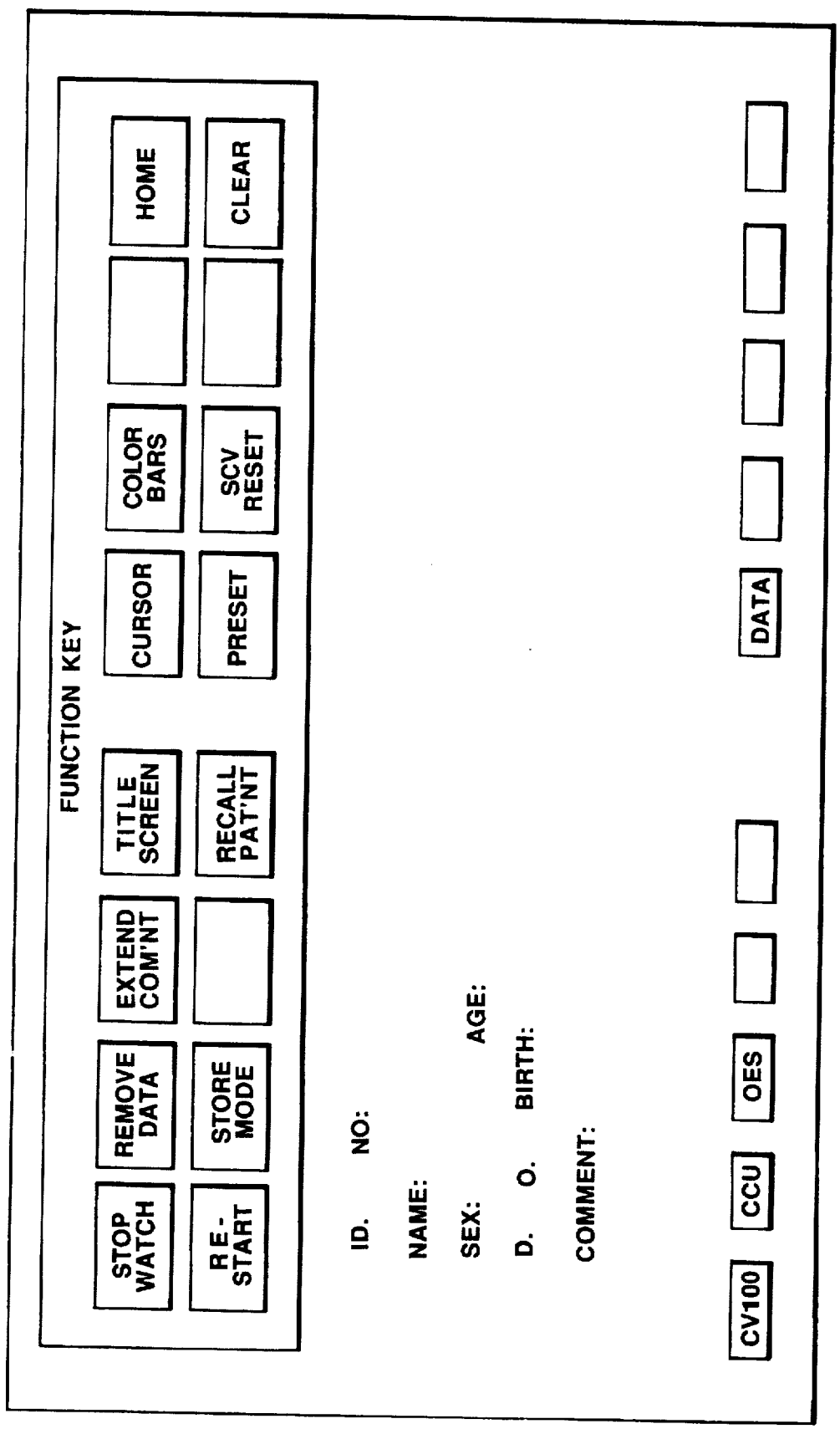
Figure 15E:
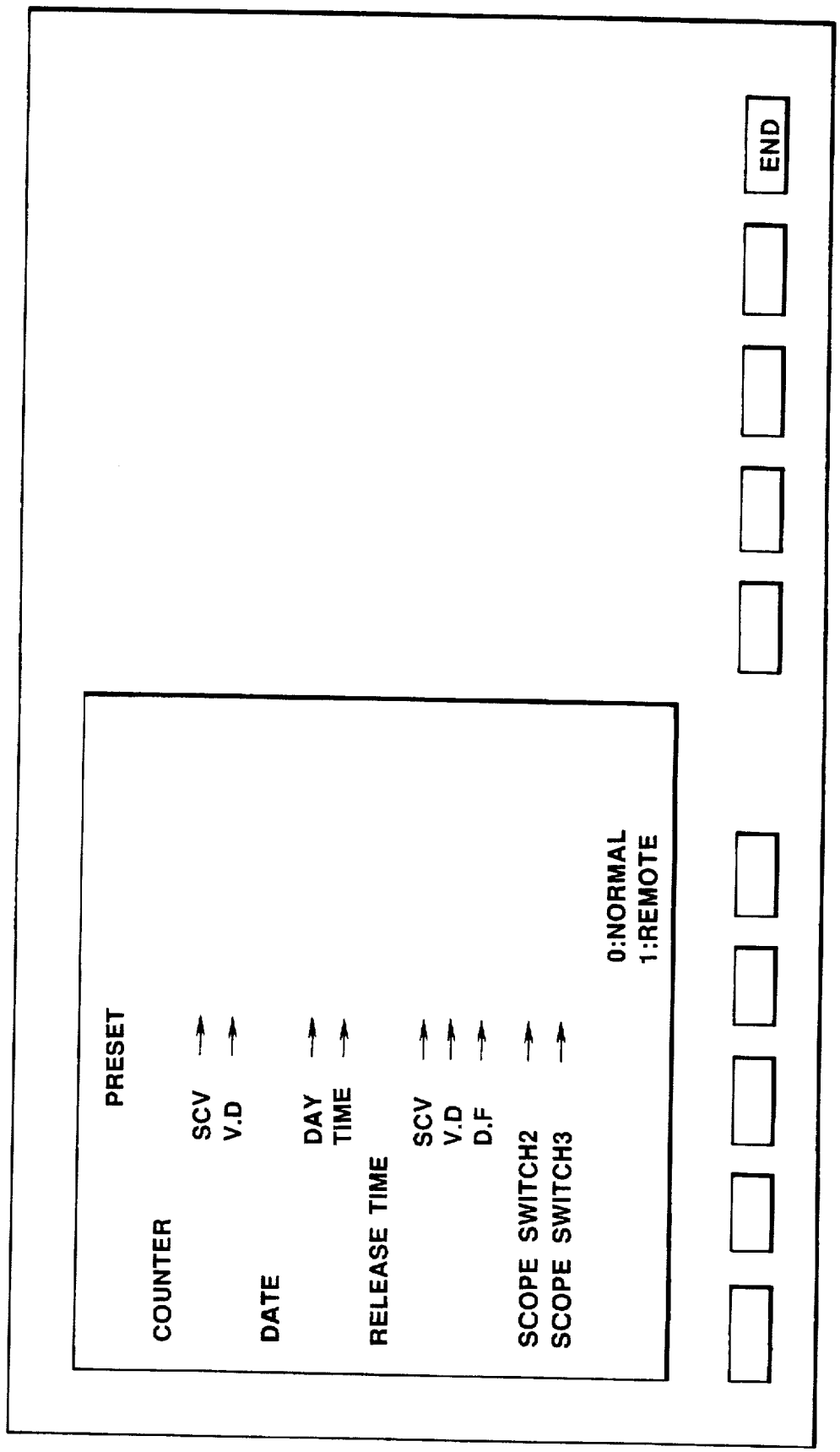
Figure 15H:
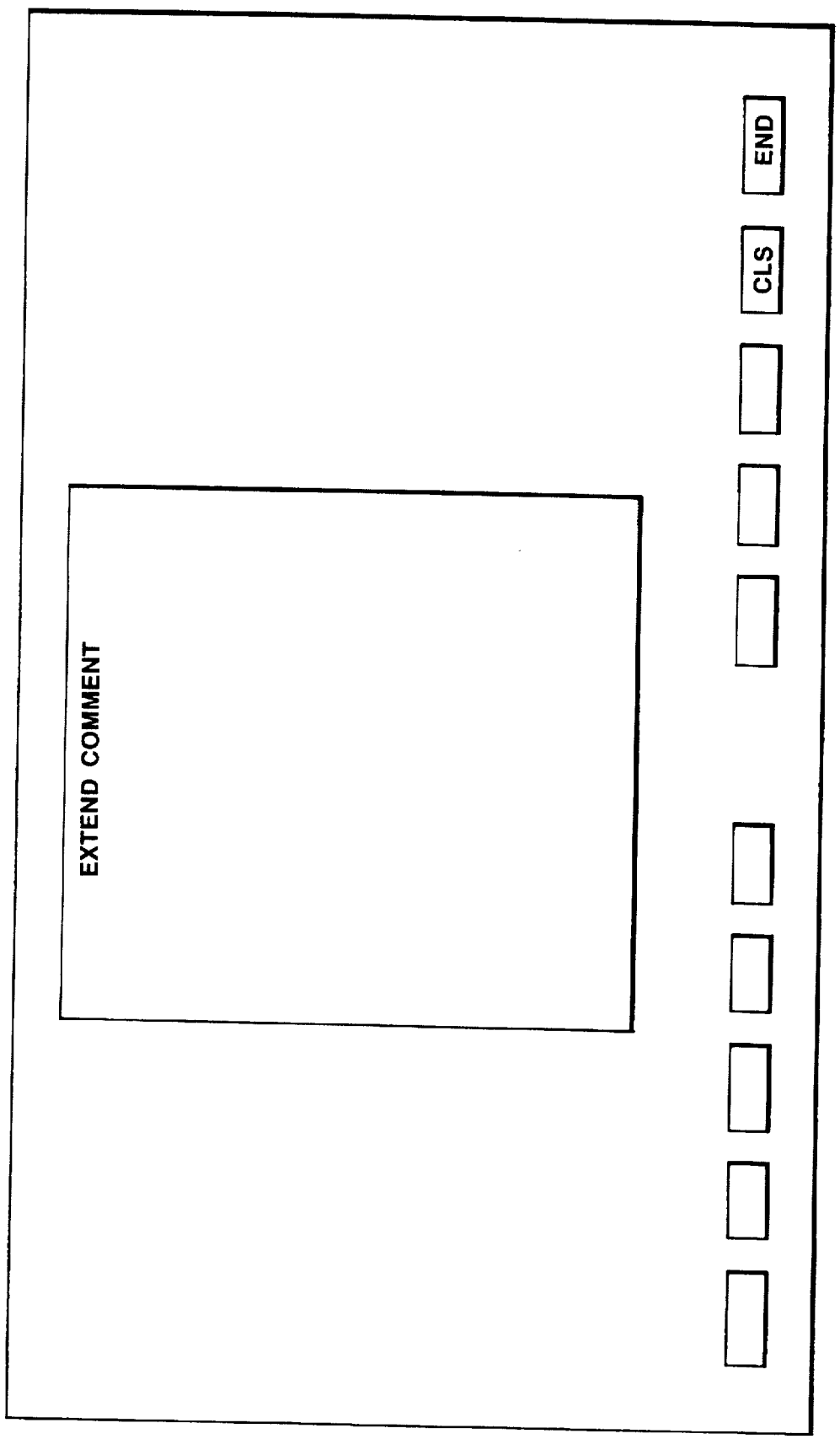
Figure 15J:
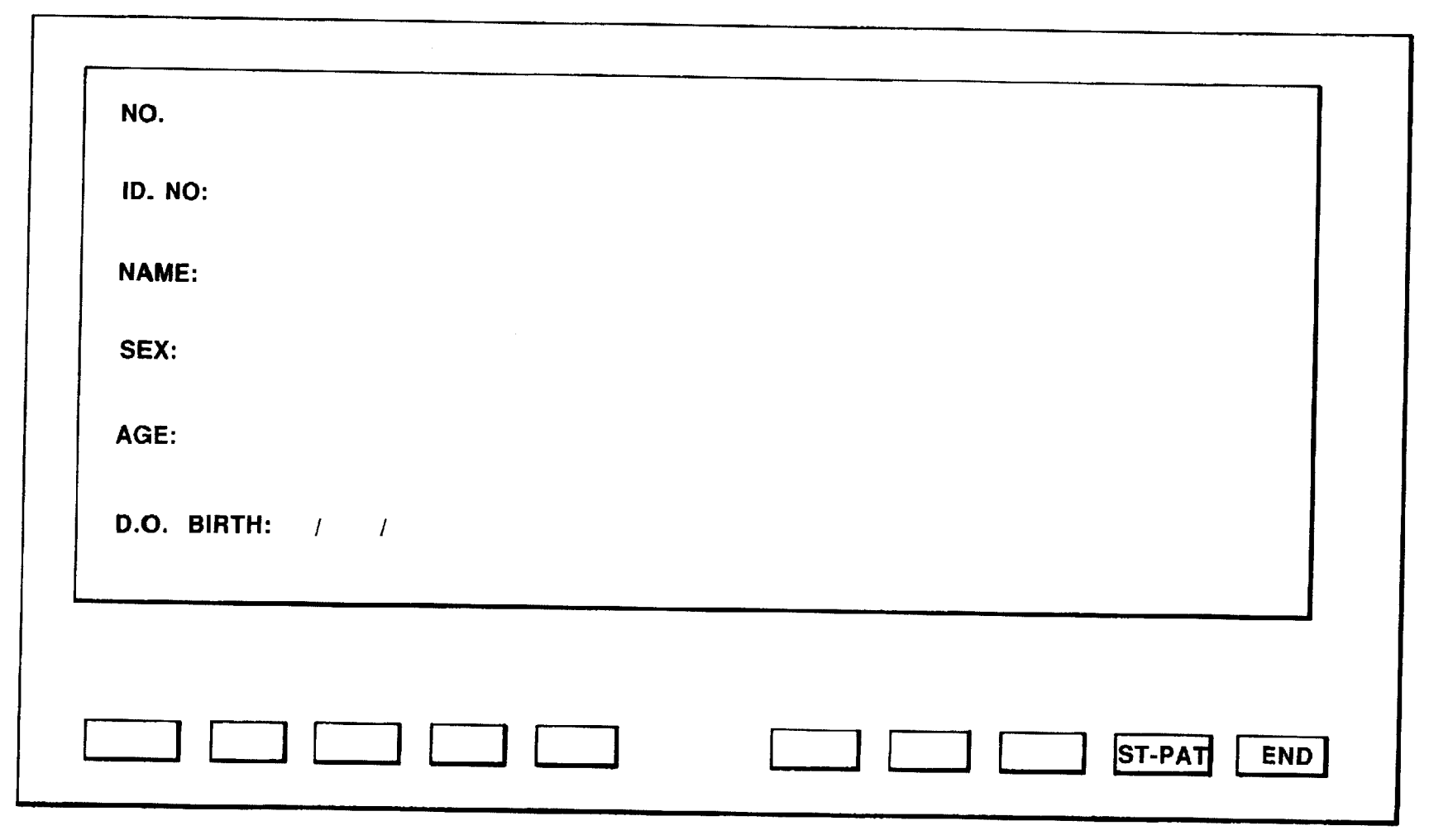

In FIG. 14D, the same processing as that in the CV-100 mode shown in FIG. 14C is performed in the OES mode. As a result, the screens shown in FIGS. 15A, 15B, and 15D are displayed. In FIG. 15A, for example, CV100, CCU, OES, and DATA in the lower part of the screen are screen change keys (switches). Keys (switches) above these screen change keys are used to operate the CV-100.

FIG. 14E shows the contents of CCU-mode processing. The contents of processing is substantially identical to that in the CV-100 or OES mode.

Figure 14F:
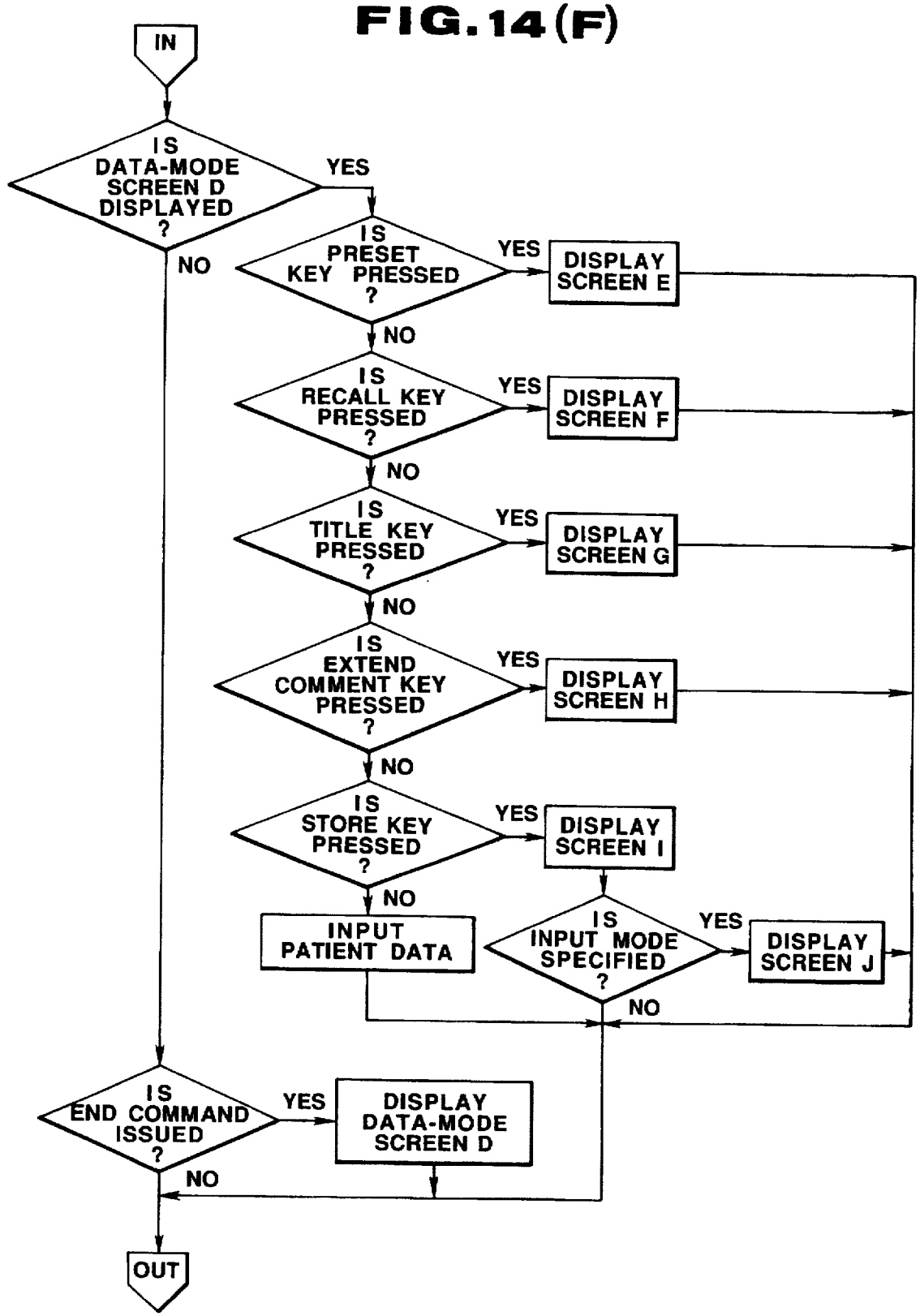

FIG. 14F shows the contents of data-mode processing. When it is determined that the data mode is selected, it is determined which key is pressed: the PRESET, RECALL, TITLE, EXTEND COMMENT, or STORE key. Based on the result of the determination, any of FIGS. 15E, 15F, 15G, 15H, and 15I is displayed. When the STORE key is pressed, if input is done, the screen shown in in FIG. 15J appears.

When it is determined that any of the PRESET, RECALL, TITLE, EXTEND COMMENT, and STORE keys is not pressed, patient data is identified. The patient data is then input.

When power is turned on, the screen previously used appears.

In the first embodiment, the electric cautery unit 28 and heat probe unit (HPU in FIG. 13) 23 are installed beyond the control of the control computer 4. As shown in FIGS. 3 and 5, the operation panels thereof are arranged at positions most suitable for a doctor and a nurse to operate them.

The electric cautery unit 28 and heat probe unit 23 are not used so frequently as the VSC 5 or light source apparatus 6 during endoscopic examination. The electric cautery unit 28 and heat probe unit 23 are therefore not connected to the control computer 4 as shown in FIG. 13, and not controlled by the control computer 4. The operation panels thereof are installed at easy-to-operate positions.

The water containers for the heat probe unit 23, light source apparatus 6, and maintenance unit 84 accommodated in the main unit 11 of a control apparatus are backlighted by a backlight illumination unit 85 so that the water levels thereof will be identified at sight through the openings 36A, 37A, and 38A of the back cover 40B of the main unit 11 of a control apparatus.

The VSC 5 provides the light source apparatus 6 with a flash control signal or EE control signal. The light source apparatus 6 has a flash unit 86 for flashing.

The suction pump 87 is used to connect the aspirator tube 39 for aspiration.

The monitor 13 to be connected to the VSC 5 and CCU 29 is connected with a first submonitor 89 and a second submonitor 89', which use liquid crystal displays, via a distributor 88. The submonitors 89 and 89' do not have an output terminal, and therefore cannot be cascaded mutually. The distributor 88 is therefore used to connect the submonitors 89 and 80'.

The VSC 5 can be connected to, for example, an image file unit 90 over an input/output line 30, which enables transfer of image data or the like.

The control computer 4, operation computer 3, still image photography unit 41, SVR 41a, monitor 13, and submonitors 89 and 89' are isolated from the power supply.

According to the first embodiment, the advantages below are available.

Equipment required for endoscopic examination including a treatment procedure are accommodated or made available, which relieves a user from walking about. The power supplies are managed as a whole. Video and other signals are centralized and managed together with the terminals.

The tray 14 is placed on the columnar section 11a of the main unit 11 of a control apparatus. Tools and instruments required for examination can be put in the tray 14. An endoscope or the like required for examination can be picked up by rotating the rotatable tray 14, which helps minimize a user's moving range.

The display 52 of the operation computer 3 serving as an operation unit has operational functions as well as original display functions, and includes the keyboard 7 to enable data entry.

The tubes, aspirator, water containers, simplified cleaning unit, and cleaning cup are all accommodated to enable cleaning of the entire system.

The still image photography unit is incorporated, enabling recording within the system.

Online connection with an external image filing system permits total systematization.

The monitor 13 is mounted on the main unit 11 of a control apparatus in such a manner that the monitor 13 can change positions freely. The monitor 13 can therefore be relocated at a position at which it can be observed optimally.

As mentioned above, according to the first embodiment, almost all the equipment required for endoscopic examination are accommodated in or connectable to the main unit 11 of a control apparatus. Moreover, control and operational functions needed by a doctor are located so that the doctor can use them smoothly, while those needed by a nurse are located so that the nurse can use them smoothly. Control and operational functions used frequently are operated by a centralized operation unit. A centralized control (management) means is provided to enable centralized control. The centralized operation unit is designed to be rotatable, and therefore can be oriented so that both a doctor and a nurse can use it easily. (Only the display 52 of the centralized operation unit may be installed at a position at which a doctor and nurse or a primary and secondary users can observe it easily. Alternatively, the centralized operation unit may be installed at respective positions convenient to the primary and secondary users.) Since the main unit of a control apparatus is shaped like a deformed square pole, a doctor and a nurse can pass scopes, treatment adapters, and other accessories smoothly.

In short, according to the first embodiment, only the operation computer 3 is needed to operate the component equipment of an endoscope system which are required to be operated during major endoscopic examination (including treatment using treatment adapters). This provides a lot of advantages described previously and greatly improves the operability for endoscopic examination.

A computer is used to control an operation display and peripheral equipment, which allows a user to actuate multiple different equipment using a single switch or operate the equipment in harmony. Furthermore, since a centralized operation unit comprises graphics of display screens on the computer and a touch panel. The layout of switches can be modified depending on the combination of units, or screens can be changed according to a unit to be controlled. The centralized operation unit can thus be constructed flexibly according to the system configuration.

Multiple operation screens to be displayed on the centralized operation unit are associated with functions and units. Screens associated with functions of peripheral equipment to be controlled can be displayed selectively. The centralized operation unit permits easy operation of many functions with excellent operability, and helps prevent erroneous use.

As for an appearance, since no part is projecting, a doctor and a nurse can move smoothly.

Many inconveniences and drawbacks of the prior arts; that is, cables extending from peripheral equipment are laid on the floor to interrupt smooth movement during operation and equipment to be operated are distributed, have been dissolved.

In FIG. 13, the relationship between the control computer 4 and VSC 5 may apply to the CCU 29.

A mouse or the like may be used instead of the touch panel 2. Alternatively, the mouse and touch panel may be used in combination.

Figure 16:
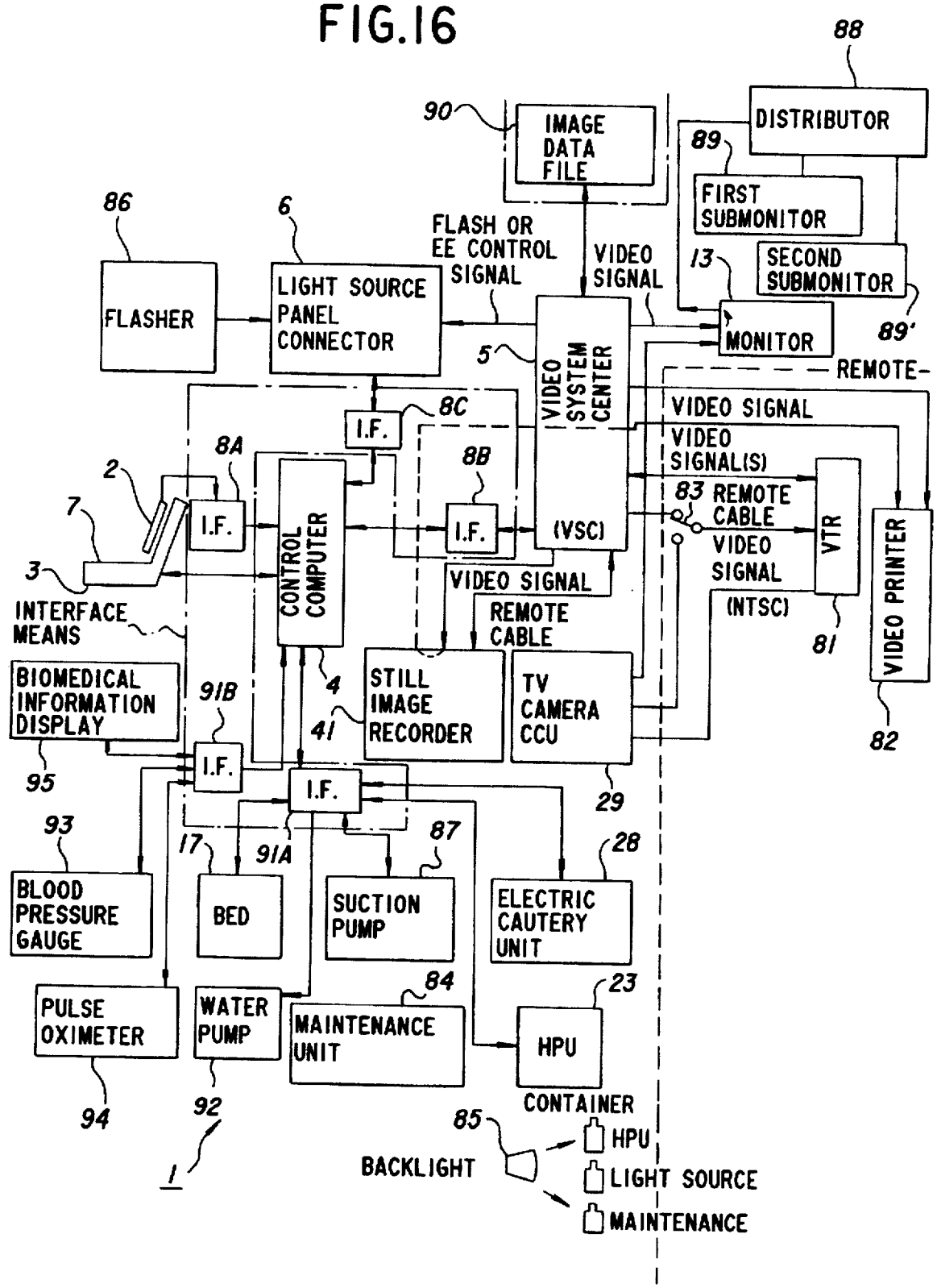
FIG. 16 is a configurational diagram showing an overall configuration of a system relating to the second embodiment of the present invention.

FIG. 16 is a configurational diagram of an entire system relating to the second embodiment of the present invention.

In the first embodiment, the electric cautery unit 28 and heat probe unit 23 are installed beyond the control of the control computer 4. Specifically, the electric cautery unit 28 or the heat probe unit 23 has multiple operation panels so as to be easily operated at multiple places. Both the electric cautery unit 28 and heat probe unit 23 are designed so that the control will not be centralized by the control computer 4.

In the second embodiment, an electric cautery unit 28, a heat probe unit 23, a suction pump 87, a bed 17, and a water pump 92 for supplying water are connected to a control computer 4 via an interface 91A. A blood pressure gauge 93 for metering a patient's blood pressure, a pulse oximeter 94 for metering a heart rate and blood oxygen saturation, and a biomedical information display 95 for displaying patient's biomedical information such as a blood pressure and heart rate are connected to the control computer 4 via an interface 91B. The control computer 4 is connected to peripheral equipment via interface means enclosed with a dot-dash line.

The other components are identical to those in the first embodiment shown in FIG. 13.

The electric cautery unit 28, heat probe unit 23, and suction pump 87 are connected to the control computer 4, so that they can be operated, similarly to the light source apparatus 6 and VSC 5, by operating a touch panel 2 and an operation computer 3. Based on the operation, the control computer 4 controls the operations of units. Patient's biomedical information acquired by the blood pressure gauge 93 and pulse oximeter 94 can be displayed on the biomedical information display 95 under the control of the control computer 4. During endoscopic diagnosis or treatment, the patient's biomedical information can be checked effortlessly.

Figure 17:
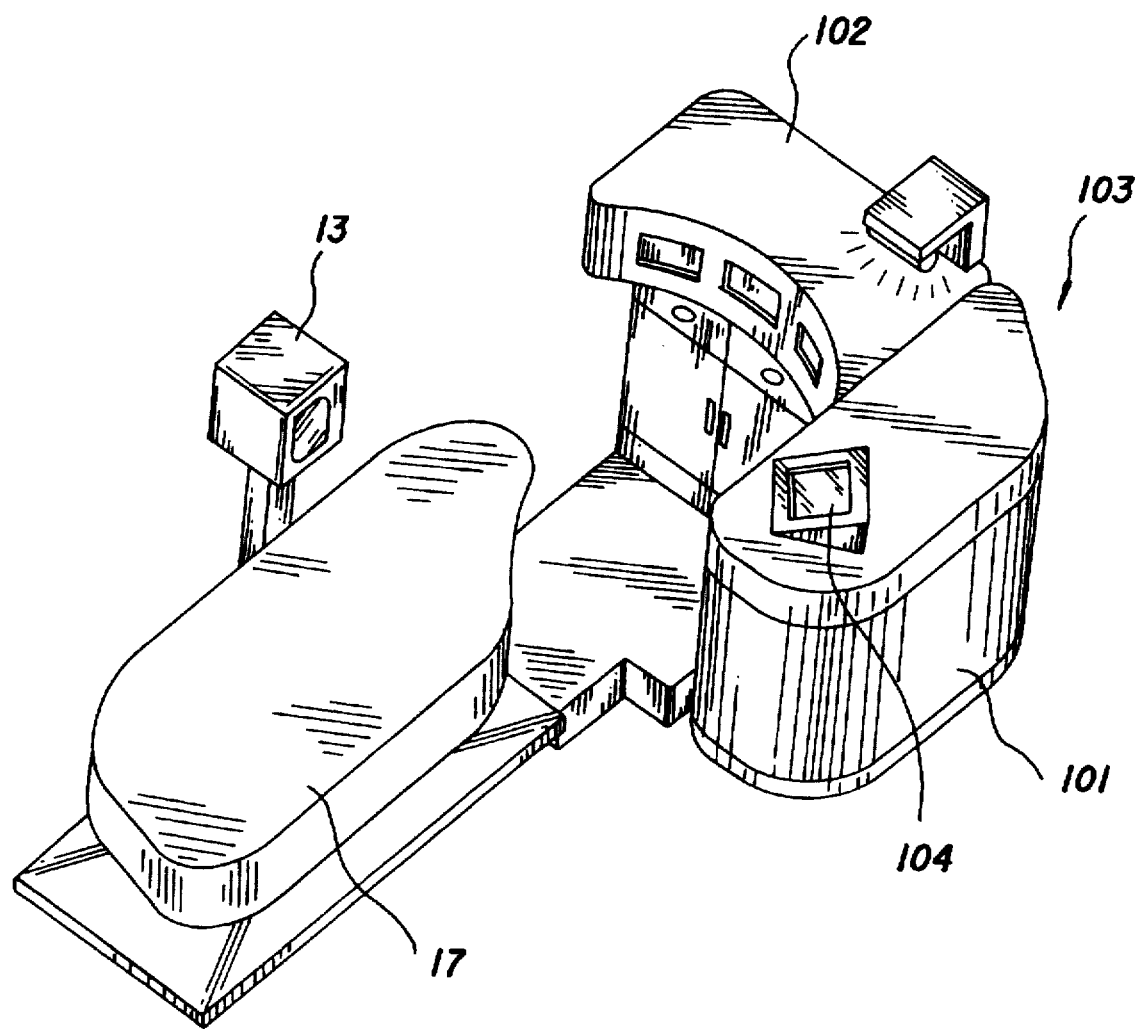
FIG. 17 is an oblique view showing an appearance of an endoscope system in which the configuration of FIG. 16 is implemented.
Figure 57:
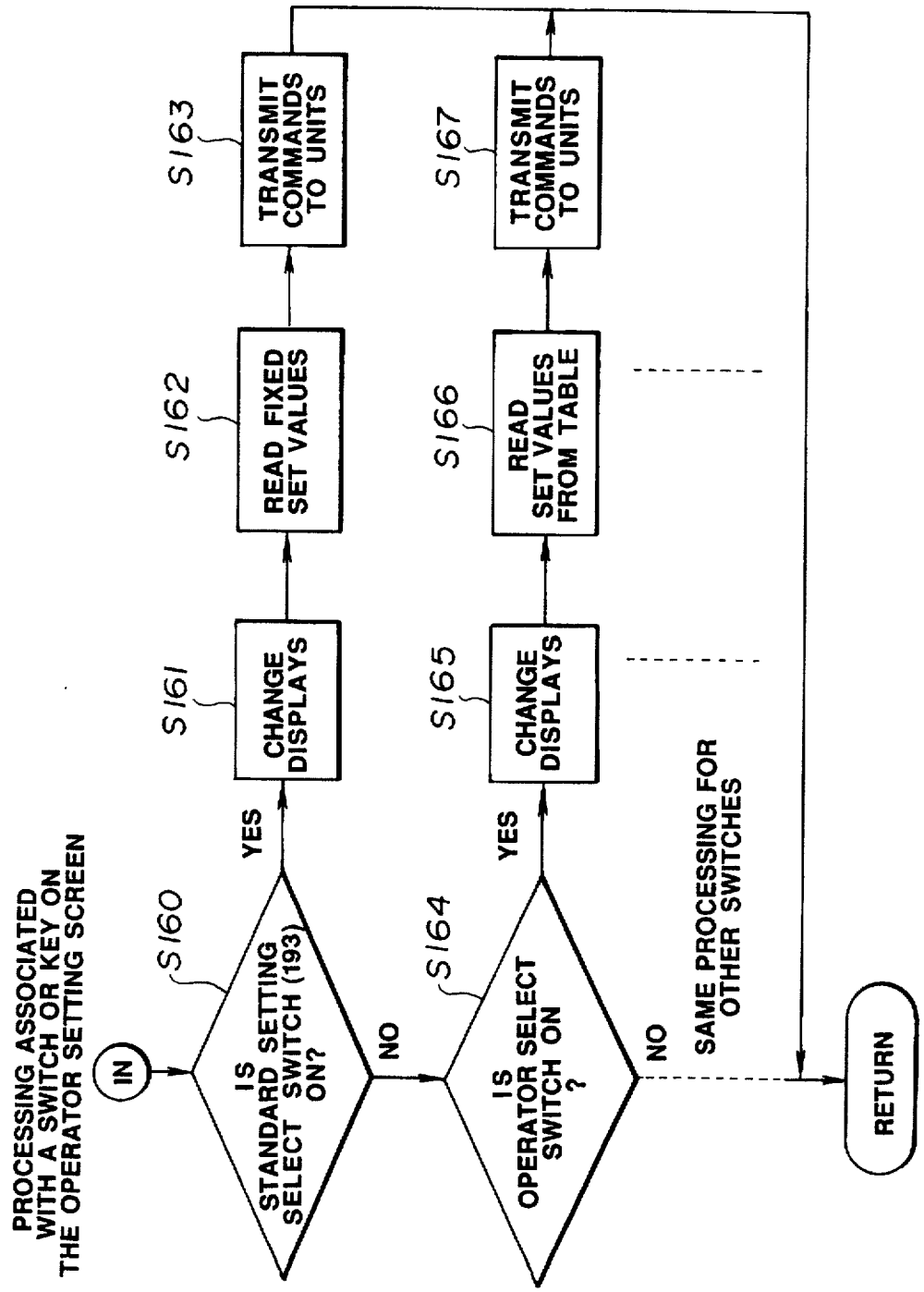

FIGS. 17 and 57 show examples of an arrangement of an endoscope system in which the configuration shown in FIG. 16 is implemented.

Figure 18:
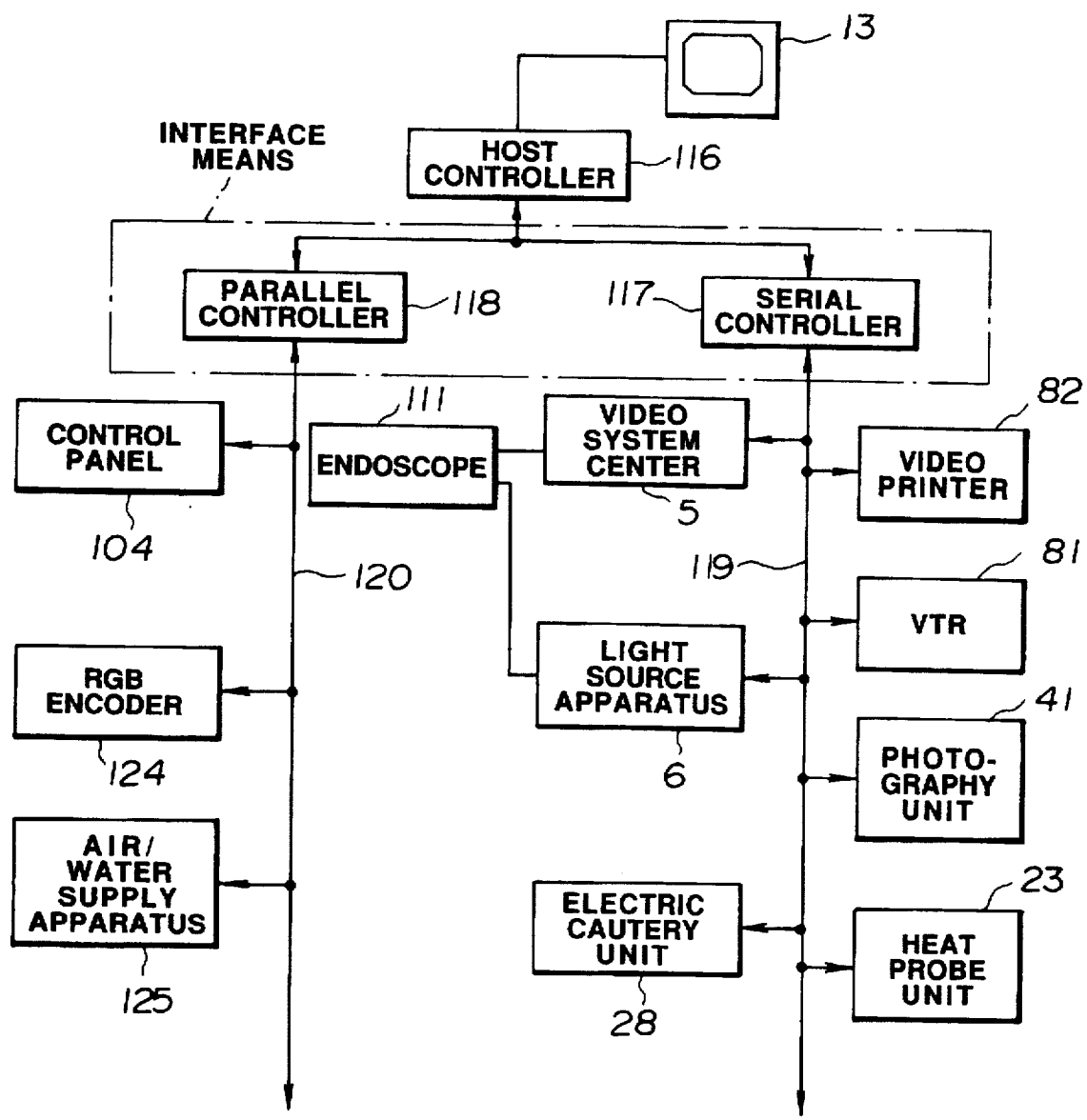
FIG. 18 is a block diagram showing a configuration of a control system of the endoscope system in FIG. 17.

An endoscope system of this embodiment consists mainly of, as shown in FIG. 17, a system body 103 made up of a doctor workstation 101 and a nurse workstation 102, a control panel 104 serving as a main operational instruction means designed for centralized operation of the system, and a monitor 13 for displaying endoscopic images. Accommodated in the system body 103 are, as shown in FIG. 18, the light source apparatus 6 that is connected to an endoscope 111 and supplies illumination light to a subject, a video system center 5 for controlling the endoscope 111 and processing image signals, a diathermy (heat probe unit) 23 for cauterizing a lesion, and an electric cautery unit 28 for resecting a lesion. A motor-driven bed 17 that is movable vertically is installed in the vicinity of the system body 103. The monitor 13 is arranged above and alongside of the motor-driven bed 17.

The control panel 104 is placed on the top of the doctor workstation 101, comprising an operation screen display that is a display monitor such as a liquid crystal display and an input detector such as a transparent touch panel mounted closely on the operation screen display. Operation screens serving as operational instruction input screens, in each of which operation switches designed for operating peripheral equipment in the system are arranged, are display on the display monitor. When an area of an operation switch in an operation screen is pressed (touched), the input of an operational instruction is detected by the touch panel. The touch panel comprises numerous switches of transparent electrodes arranged in the format of a matrix. The touch panel is scanned to detect which switch is pressed and identify the coordinates of the switch.

The components of the control panel 104 are not limited to the aforesaid ones. Alternatively, an LCD, a CRT, an EL, or a plasma display may be employed as the operation screen display, and the touch panel mounted on the display, a mouse, a joystick, a keyboard, a trackball, a digitizer, or a combination thereof may be employed as the input detector.

The detailed configuration of the endoscope system will be described with reference to FIG. 18. FIG. 18 shows only the components of a control system in the endoscope system. A host controller 116 equivalent to a control computer serving as a main control means that centralizes the control of the system is incorporated in the system body 103. The host controller 116 is connected to a serial controller 117 for controlling a serial interface and a parallel controller 118 for controlling a parallel interface which serve as interface means. The host controller 116 is also connected to the monitor 13.

The host controller 116 is connected to the light source apparatus 6, video system center 5, heat probe unit 23, electric cautery unit 28, and video tape recorder (VTR) 81 for recording endoscopic images, photography unit 41 for photographing endoscopic images as still images, and video printer 82 for outputting endoscopic images to paper over a serial interface line (serial I/F line) 119 via the serial controller 117. The host controller 116 is also connected to the control panel 104, an RGB encoder 124 for converting video signals into R, G, and B image signals, and an air/water supply apparatus 125 having a water pump 92 and a suction pump 87 for supplying water and air respectively over a parallel interface line (parallel I/F line) 119 via the parallel controller 118.

The host controller 116 inputs or outputs control signals from or to connected units and controls the actions of the units. Herein, when an operation switch formed on the control panel 104 or on an operation unit of the endoscope 111 is pressed, operational instruction information is sent to the host controller 116. The host controller 116 transmits a control signal to a unit concerned and thus controls the unit concerned. When the control panel 104 is operated, the coordinates of a pressed switch is detected as described previously. The host controller 116 checks the coordinates of the switch with respect to the operation screen, and transmits a control signal representing an instruction for the operation switch displayed on the screen to the peripheral equipment. Alternatively, an instruction may be transmitted as a command to the host controller 116 on the basis of the coordinates of a pressed switch in an operation screen displayed on the control panel 104. The host controller 116 then transmits a control signal to a peripheral equipment concerned.

Figure 19:
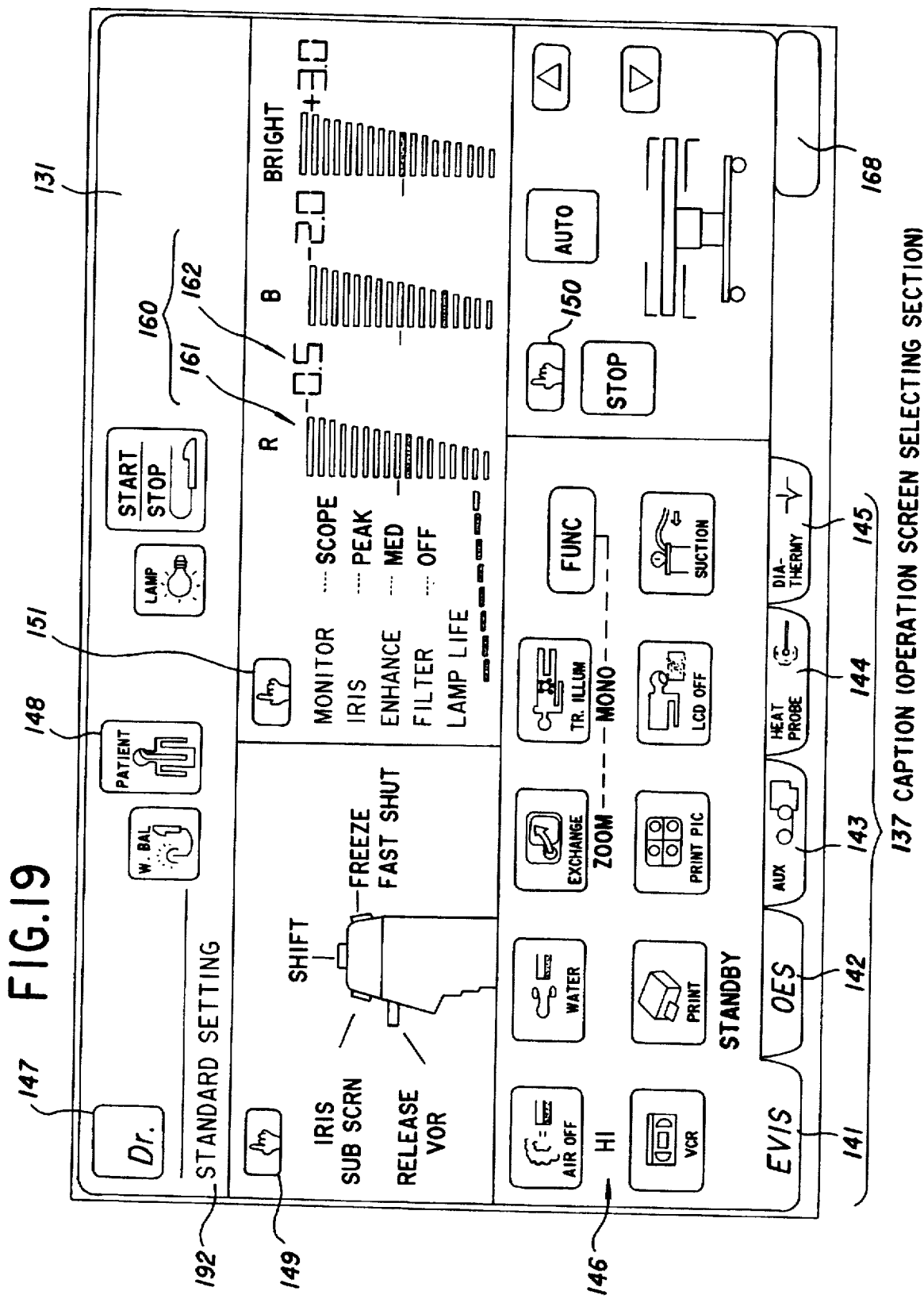
FIG. 19 is an explanatory diagram showing a main operation screen which is displayed on a control panel and used to perform major operations of a system.

The operation screen of the control panel 104 includes a plurality of operational instruction input screens which are grouped by functions and used to control a plurality of peripheral equipment of the endoscope system. A main operation screen 131 shown in FIG. 19 is displayed as an operation screen most frequently used in operating the system. The main operation screen 131 appears, for example, during initialization of the endoscope system, and permits execution of major procedures for operating the system. The main operation screen 131 is provided with various operation switches to be used when an electronic endoscope is connected.

Figure 20:
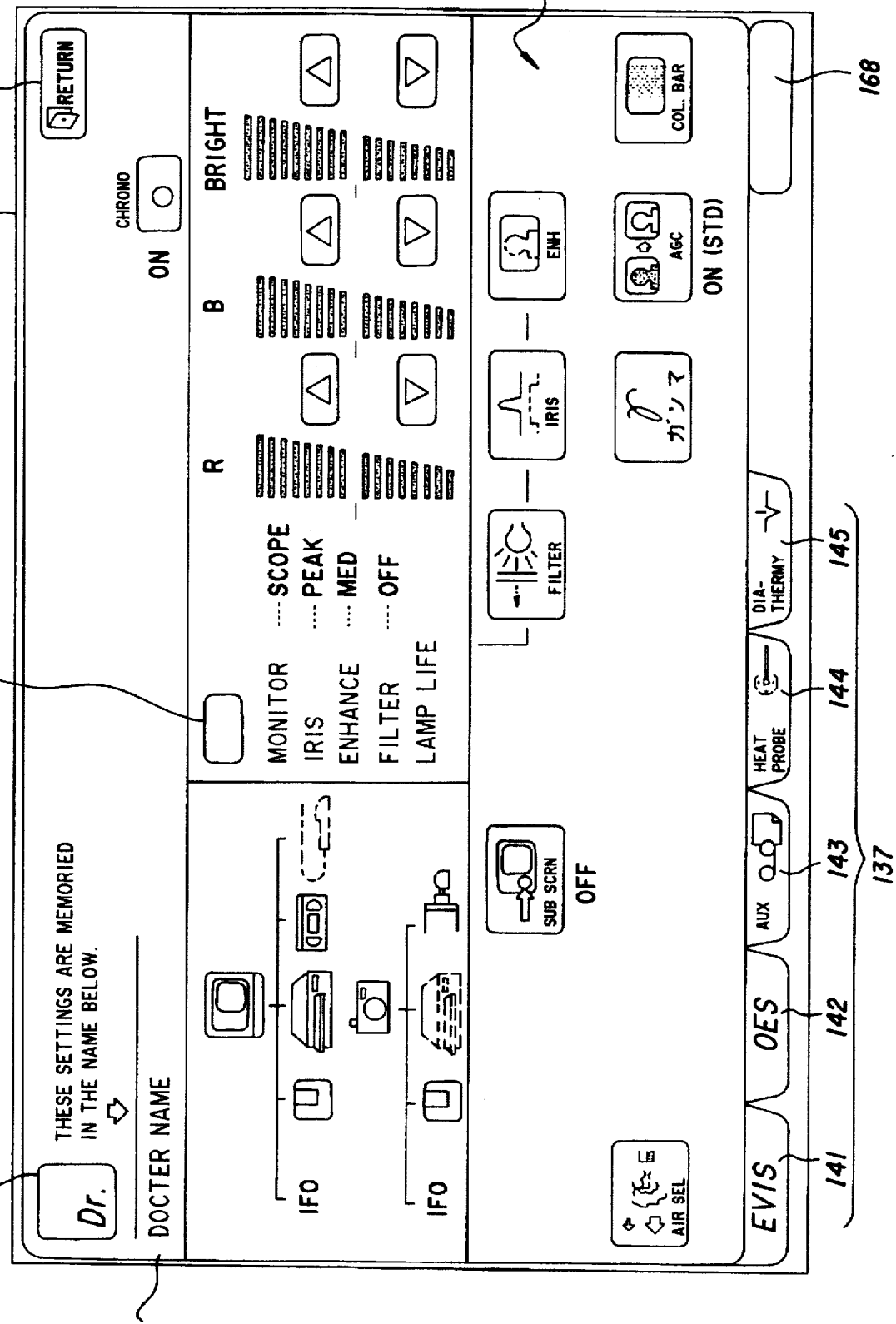
FIG. 20 is an explanatory diagram showing an electronic endoscope setting screen for use in setting various values when an electronic endoscope is connected.
Figure 21:
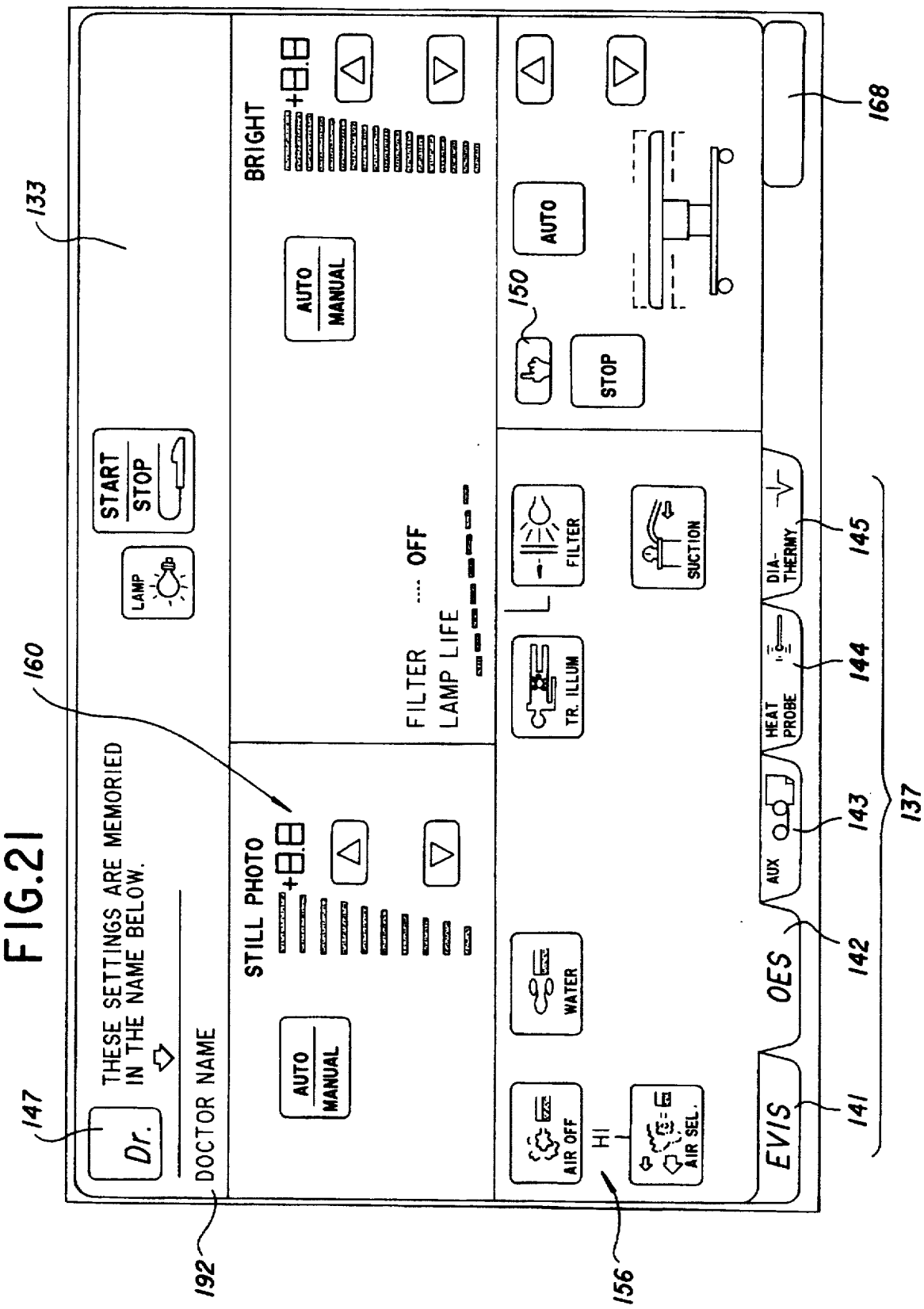
FIG. 21 is an explanatory diagram showing a fiberscope operation screen for use in performing various operations when a fiberscope is connected.
Figure 22:
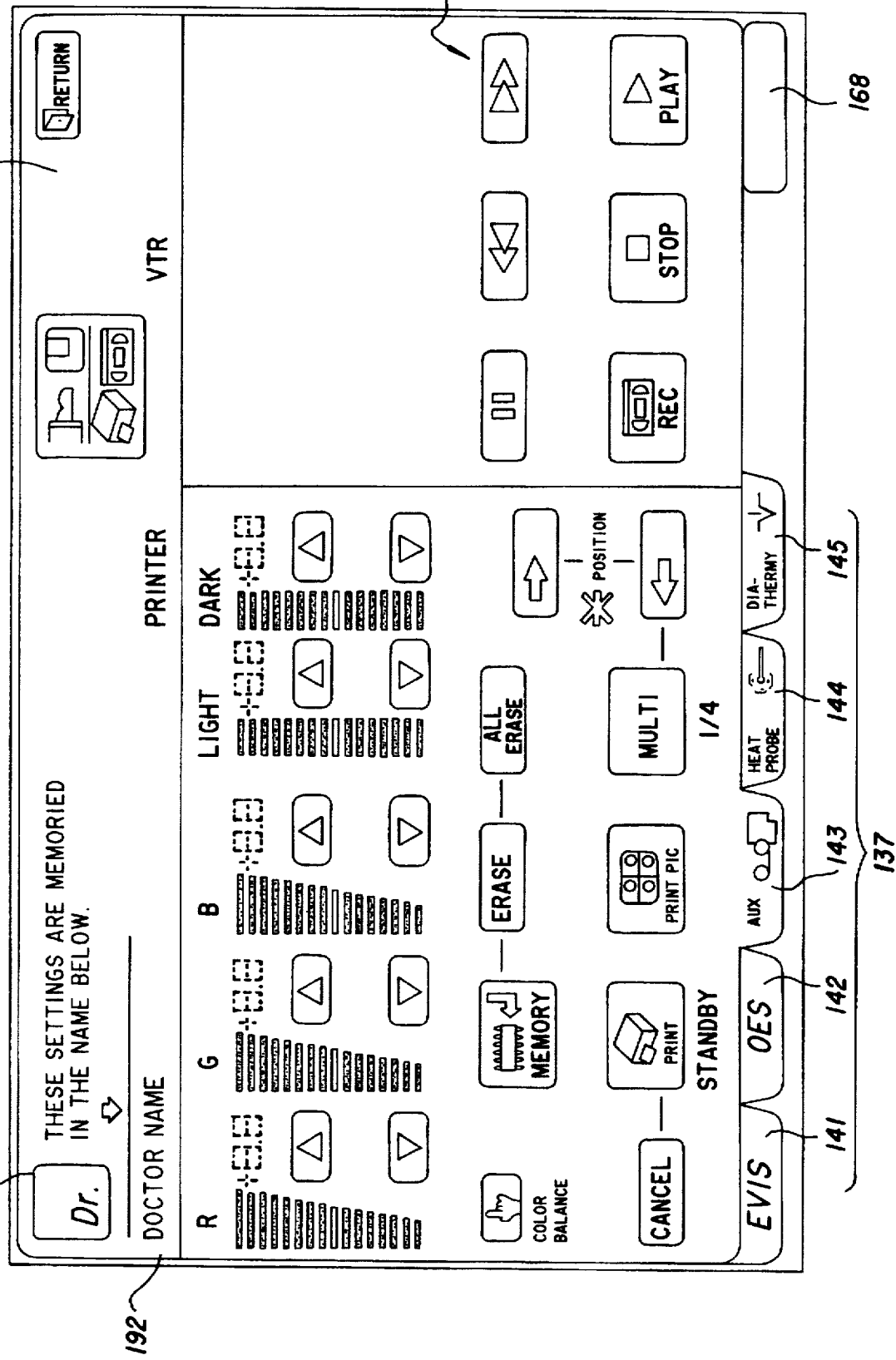
FIG. 22 is an explanatory diagram showing an external video unit operation screen for use in operating a VTR.
Figure 23:
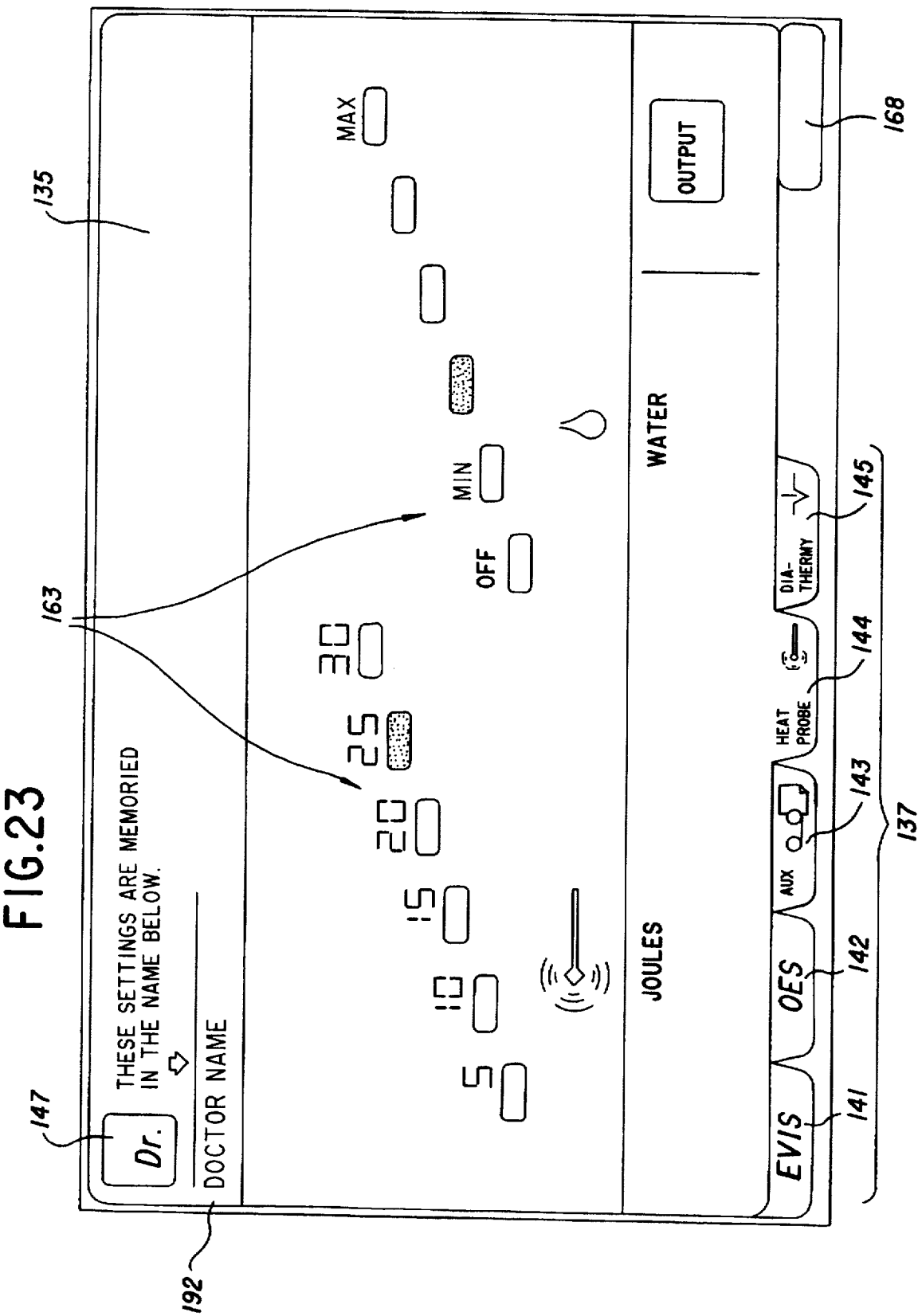
FIG. 23 is an explanatory diagram showing a heat probe unit operation screen for operating a heat probe unit.
Figure 24:
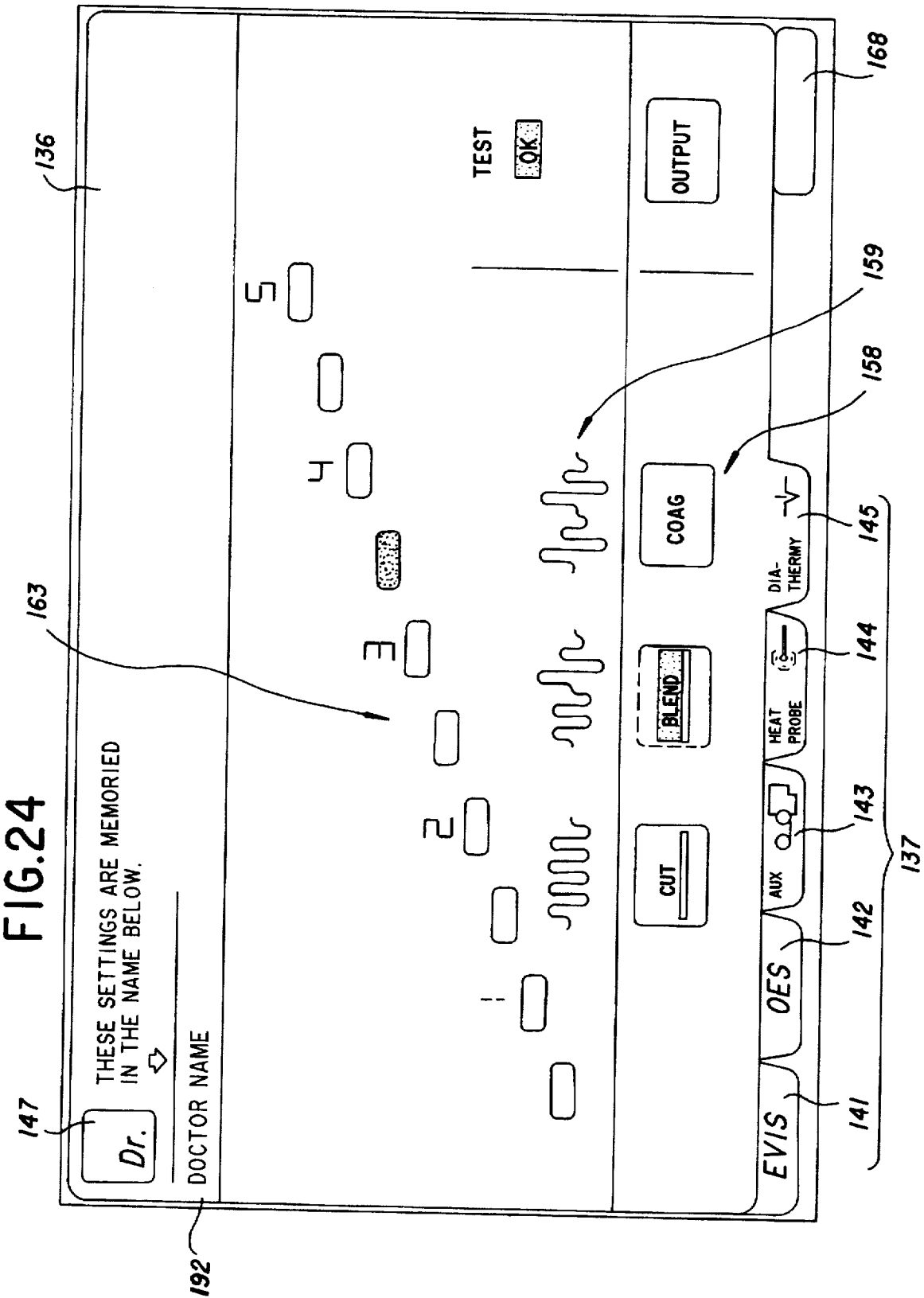
FIG. 24 is an explanatory diagram showing an electric cautery unit operation screen for use in operating an electric cautery unit.

The control panel 104 displays an electronic endoscope setting screen 132 shown in FIG. 20 for use in performing various setting with an electronic endoscope connected, a fiberscope operation screen 133 shown in FIG. 21 for use in performing various operations with a fiberscope connected, an external video unit operation screen 134 shown in FIG. 22 for use in operating the VTR 81, a heat probe unit operation screen 135 shown in FIG. 23 for use in operating the heat probe unit 23, and an electric cautery unit operation screen 136 shown in FIG. 24 for use in operating the electric cautery unit 28.

Each of the above operation screens includes, if necessary, other operation screens in each of which setting switches for an associated unit and operation switches seldom used are arranged. These operation screens are structured hierarchically and changed for operation. The main operation screen 131, fiberscope operation screen 133, external video unit operation screen 134, heat probe unit operation screen 135, or electric cautery unit operation screen 136 is constructed like a card. A caption area 137 serves as an index and consists of projecting trapezoidal captions which are formed on the bottoms of respective card-like screens so as not to overlap one another.

The caption 137 serves as an operation screen selecting section for selecting an operation screen associated with an intended unit to be operated, and includes screen select switches; such as, a main operation screen select switch EVIS 141, a fiberscope operation screen select switch OES 142, an external video unit operation screen select switch AUX 143, a heat prove unit operation screen select switch HEAT PROBE 144, and an electric cautery unit operation screen select switch DIATHERMY 145. When a select switch in the operation screen selecting section is selected, an operation screen associated with the thus-selected and intended unit appears. Any of the operation switches arranged in the screen is then pressed to perform any of various operations.

Figure 25A:
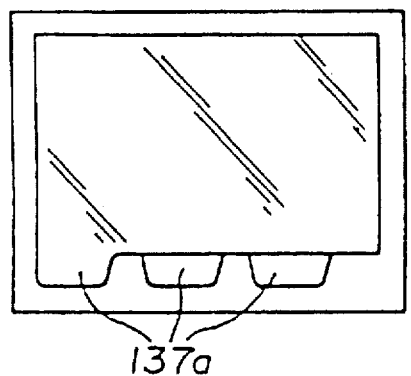
FIGS. 25a to 25d are explanatory diagrams showing captions of operation screens.
Figure 25B:
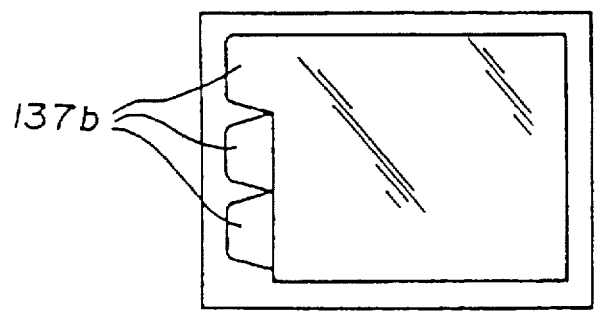
Figure 25C:
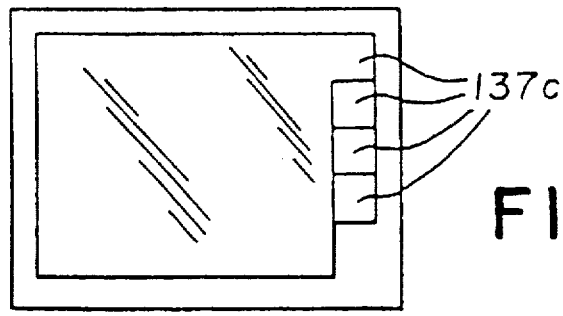
Figure 25D:
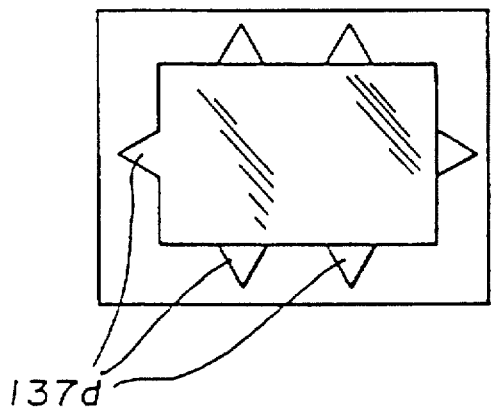

FIGS. 25a to 25d show variants in which the caption area 137 lies at different locations and have different shapes. In FIG. 25a, a caption area 137a is formed with captions separated from one another. In FIG. 25b, a caption area 137b is formed on the lateral edge of each card-like operation screen. In FIG. 25c, a caption area 137d consisting of projecting triangles is arranged circumferentially along the margin of a card-like operation screen. These variants are conceivable. Alternatively, an operator may select a favorite format for the caption area 137 so that he/she can use captions in an optimal manner for an intended operation.

Next, the operations of the endoscope system of this embodiment when the endoscope system is in use will be described.

An operator connects an electronic endoscope or a fiberscope to the light source apparatus 6 and video system center 5 in the system body 103, and then conducts endoscopic observation or diagnosis. A heat probe connected to the heat probe unit 23 or an electric cautery connected to the electric cautery unit 28 is inserted into a channel in the endoscope for treatment. The control panel 104 placed on the system body 103 is operated to control peripheral equipment on a centralized basis.

Figure 26:
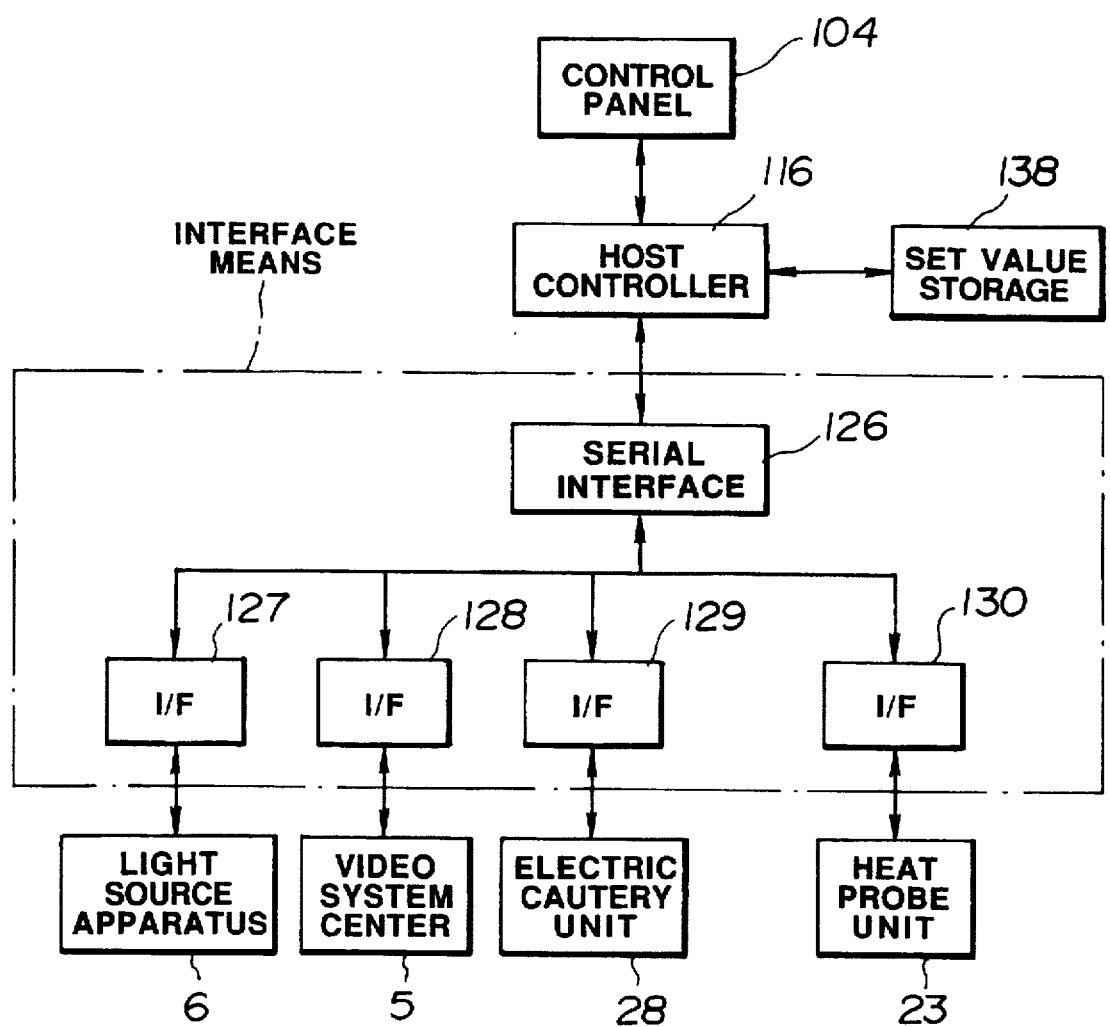
FIG. 26 is a block diagram showing a functional structure for controlling peripheral equipment at a control panel.

FIG. 26 is a block diagram showing a functional structure for controlling peripheral equipment at the control panel 104. When operational instruction information is sent from the control panel 104 to the host controller 116, the host controller 116 transmits a control signal to an associated peripheral equipment via the serial interface 126. The serial interface 126 is connected to the light source apparatus 6 via a light source interface (I/F) 127, to the video system center 5 via a video processor interface (I/F) 128, to the electric cautery unit 28 via an electric cautery interface (I/F) 129, and to the heat probe unit 23 via a heat probe interface (I/F) 130. The peripheral equipment are controlled on a centralized basis with control signals sent from the host controller 116.

Operation screens are displayed on the control panel 104. Each of the operation screens consists of operation switches, and indicators that indicate states of use and operation. When a screen select switch is selected from the caption area 137 on the bottom of an operation screen, an operation screen associated with an intended unit appears immediately. The host controller 116 is connected to a set value storage means 138, which will be described later, in which set values are stored operator by operator. Appropriate set values for units are input or output for each operator.

The detailed format and operation of each operation screen on the control panel 104 will be described below. FIGS. 36 to 57 show control processing operations relating to operation screens.

Figure 36:
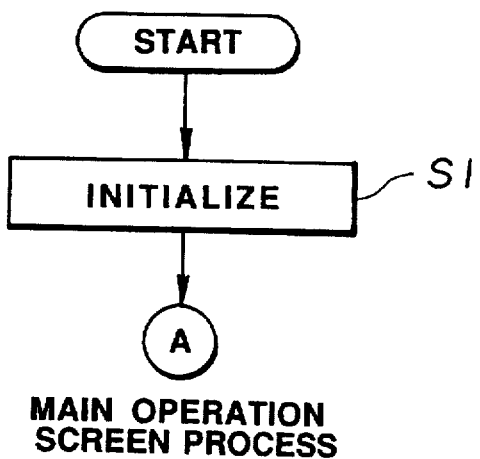
FIG. 36 is a flowchart showing initialization of the endoscope system.
Figure 39:
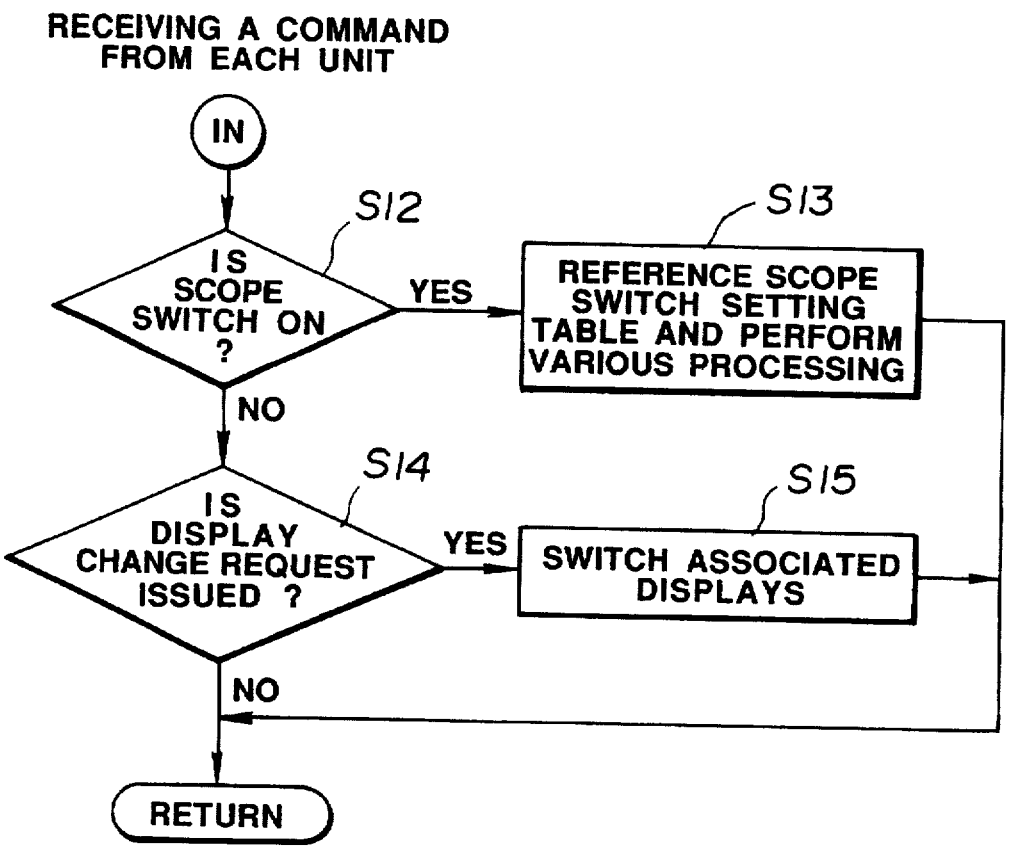
FIG. 39 is a flowchart showing the operations in command reception from equipment.

To begin with, initialization shown in FIG. 36 is performed as an initial operation. When the power supply of the system is turned on, the host controller 116 loads an operation program at a step S1 and sets peripheral equipment in the system to the states established when the power supply was turned off previously. When the power supply of the system is turned on for the first time, standard set values provided by the manufacturer are specified. The host controller 116 then passes to a process A of the main operation screen 131 shown in FIG. 19.

In the main operation screen 131 shown in FIG. 19, operation switches 146, which are concerned with an electronic endoscope, are formed in the left lower part thereof. An operator setting screen select switch 147 for calling an operator setting screen which will be described later and a patient data input screen select switch 148 for selecting a patient data input screen are formed in the upper part thereof. The operations of the video system center 5, light source apparatus 6, and air/water supply apparatus 125 are controlled using the operation switches 146. A scope switch setting screen select switch 150 for selecting a scope switch setting screen is formed in the left center thereof. A bed setting screen select switch 150 for selecting a bed setting screen is formed in the lower right part thereof. An electronic endoscope setting screen select switch 151 for selecting an electronic endoscope setting screen 132 is formed in the center thereof. When the electronic endoscope setting screen select switch 151 is pressed, the electronic endoscope setting screen 132 shown in FIG. 20 appears.

Figure 37:
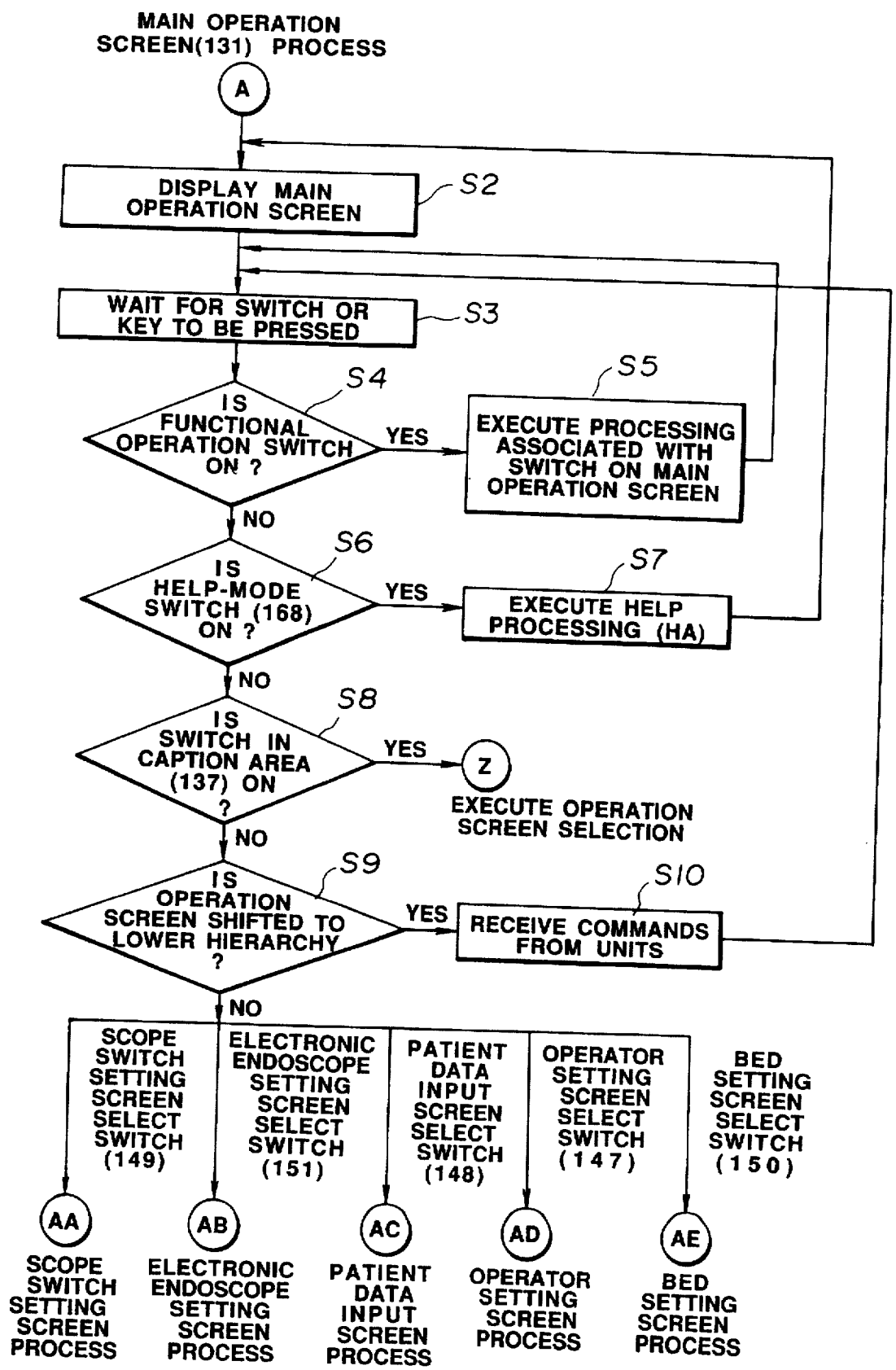
FIG. 37 is a flowchart showing the operations in a main operation screen process.

FIG. 37 shows the main operation screen process A. For the main operation screen 131, the host controller 116 displays the main operation screen at a step S2, and then waits at a step S3 until any operation switch or key in the main operation screen 131 is pressed. When an operation switch is pressed, it is determined whether the pressed switch is a functional operation switch for designating a function on the main operation screen 131. If a functional operation switch is pressed, the host controller 116 passes to a step S5, executes the processing associated with the pressed switch, and then returns to the step S3. If any functional operation switch is not pressed at the step S4, it is determined at a step S6 whether the pressed switch is a Help-mode switch 168 which will be described later. If the Help-mode switch 168 is pressed, Help processing (HA) is executed at a step S7. Then, the host controller 116 returns to the step S2. It is determined at a step S8 whether the pressed switch is any one in the caption area 137. If a switch in the caption area 137 is pressed, Operation Screen Selection (Z) shown in FIG. 38 is executed.

In Operation Screen Selection (Z), the host controller 116 determined at a step S11 whatever screen select switch in the caption area 137 is pressed and whatever operation screen is selected. If the main operation screen select switch 141 is pressed, the host controller 116 returns to the main operation screen process (A) as it is. If the fiberscope operation screen select switch 142 is pressed, the host controller 116 passes to a fiberscope operation screen process (B). If the heat probe unit operation screen select switch 144 is pressed, the controller passes to a heat probe unit operation screen process (D). If the electric cautery unit operation screen select switch 145 is pressed, the host controller 116 passes to an electric cautery unit operation screen process (E).

Returning to FIG. 37, if the switch pressed at the step S8 is none of the switches in the caption area 137, it is determined at a step S9 whether it is instructed to shift the operation screen to a lower hierarchy; that is, whether an electronic endoscope setting screen switch 151 or any other switch for changing screen hierarchies is pressed. If the scope switch setting screen select switch 149 is pressed, the host controller 116 passes to a scope switch setting screen process (AA). If the electronic endoscope setting screen select switch 151 is pressed, the host controller 116 passes to an electronic endoscope setting screen process (AB). If the patient data input screen select switch 148 is pressed, the host controller 116 passes to a patient data input screen process (AC). If the operator setting screen select switch 150 is pressed, the host controller 116 passes to an operator setting screen process (AD). If the bed setting screen select switch 150 is pressed, the host controller 116 passes to a bed setting screen process (AE). If the determination made at any of the steps S4 to S9 is in the negative, the host controller 116 advances to a step S10, executes the command reception from equipment shown in FIG. 39, and then returns to the step S3.

During the command reception from equipment, it is determined at a step S12 whether instruction signals (command) sent from peripheral equipment originate from operation switches (scope switches) on an endoscope. If a scope switch is pressed, the host controller 116 references a scope switch setting table specified in a scope switch setting screen, which will be described later, and executes the processing associated with the pressed switch. It is determined at a step S14 whether a screen display change request is issued from any peripheral equipment. If a display change request is issued, the display of a switch on the operation screen is changed to another one according to the contents of the command received at a step S15. If an error occurs, an error message is displayed. For example, a command reporting that the suction container for the aspirator becomes full, the switch suction pump switch is turned off and the graphic of the SUCTION switch in the operation screen is changed to the one indicating "off."

Next, the electronic endoscope setting screen process (AB) will be described.

When various set values related to an electronic endoscope, for example, the tone or brightness of an image and a quantity of supplied air are to be modified, the electronic endoscope setting screen select switch 151 in the main operation screen 131 is pressed to select the electronic endoscope setting screen 132. Electronic endoscope setting switches 152 for use in modifying the set values related to an electronic endoscope are formed in the lower part of the electronic endoscope setting screen 132, and a screen hierarchy up switch 153 is formed at the right upper corner thereof. After set values are adjusted in the electronic endoscope setting screen 132, if the main operation screen 131 should be called back, the screen hierarchy up switch 153 is pressed to select the main operation screen 131. The screen hierarchy up switch 153 may be designed to blink so that it will be differentiated from other switches and be more clearly visible. The screen hierarchy up switch 153 may not be installed in particular, wherein the electronic endoscope setting screen select switch 151 is re-pressed to return to the original main operation screen 131.

Figure 40:
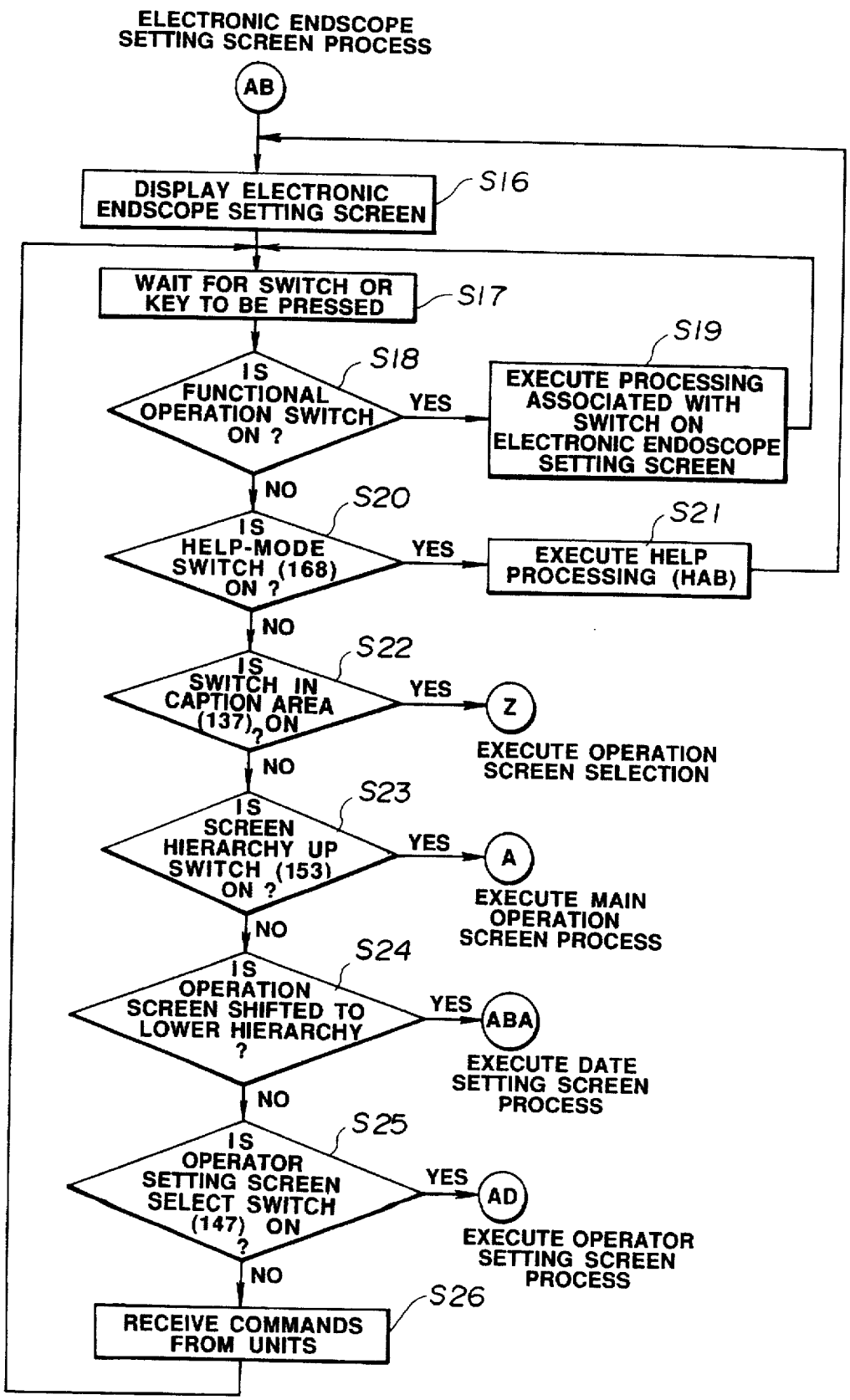
FIG. 40 is a flowchart showing the operations in an electronic endoscope setting screen process.

FIG. 40 shows the operations in the electronic endoscope setting screen process (AB). The host controller 116 displays the electronic endoscope setting screen at a step S16, and waits at a step S17 until any functional operation switch or key in the electronic endoscope setting screen 132 is pressed. If a functional operation switch is pressed, the host controller 116 advances to a step S19, executes the processing associated to the pressed switch, and then returns to the step S17. If any functional operation switch is not pressed at the step S18, it is determined at a step S20 whether the pressed switch is the Help-mode switch 168. If the Help-mode switch 168 is pressed, the host controller 116 advances to a step S21, executes Help processing (HAB), and then returns to the step S16. Next, it is determined at a step S22 whether the pressed switch is any one in the caption area 137. If a switch in the caption area 137 is pressed, Operation Screen Selection (Z) shown in FIG. 38 is executed.

At a step S23, it is determined whether the screen hierarchy up switch 153 is pressed. If the screen hierarchy up switch 153 is pressed, the host controller 116 returns to the main operation screen process (A) shown in FIG. 37. it is determined at a step S24 whether it is instructed to shift the operation screen to a lower hierarchy. If it is instructed to shift the operation screen to a lower hierarchy, a date setting screen process (ABA), which will be described later, is executed. At a step S25, it is determined whether the operator setting screen select switch 147 is pressed. If the operator setting screen select switch 147 is pressed, an operator setting screen process (AD) is executed. If the determination made at any of the steps S18 to S25 is in the negative, the host controller 116 advances to a step S26, executes the command reception from equipment shown in FIG. 39, and then returns to the step S17.

Figure 27:
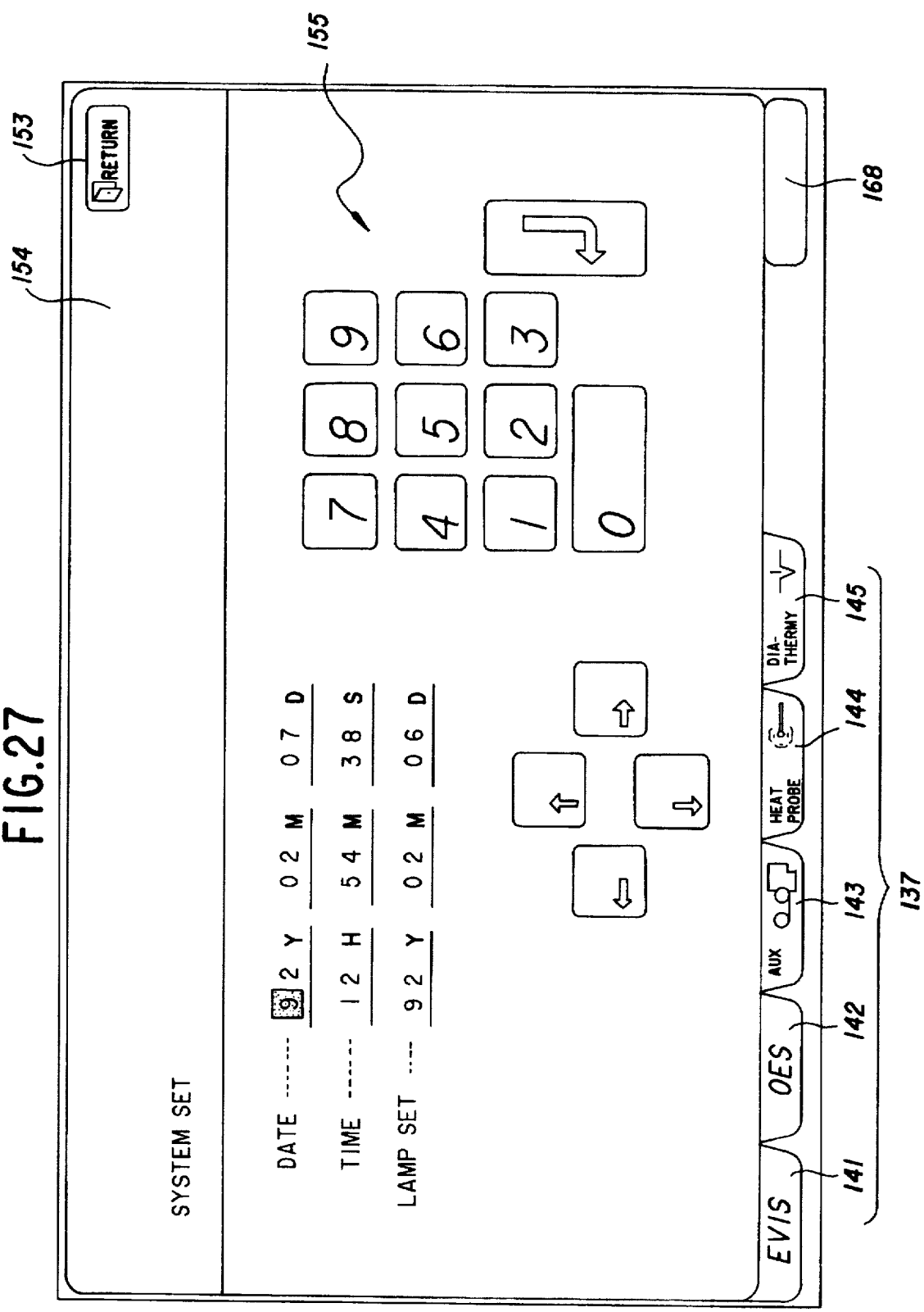

In this embodiment, when the electronic endoscope setting screen select switch 151 is re-pressed in the electronic endoscope setting screen 132, the date setting screen 154 shown in FIG. 27 is selected. When it becomes necessary in the electronic endoscope setting screen 132 to modify set values, for example, a date in the system and a date of exchanging lamps, the date setting screen 154 is displayed. The date setting screen 154 has setting keys 155 for use in setting a date, and also includes, similarly to the electronic endoscope setting screen 132, the screen hierarchy up switch 153. After a date is set using the setting keys 155, the screen hierarchy up switch 153 is pressed to return to the one of a higher hierarchy (herein, the electronic endoscope setting screen 132).

Figure 41:
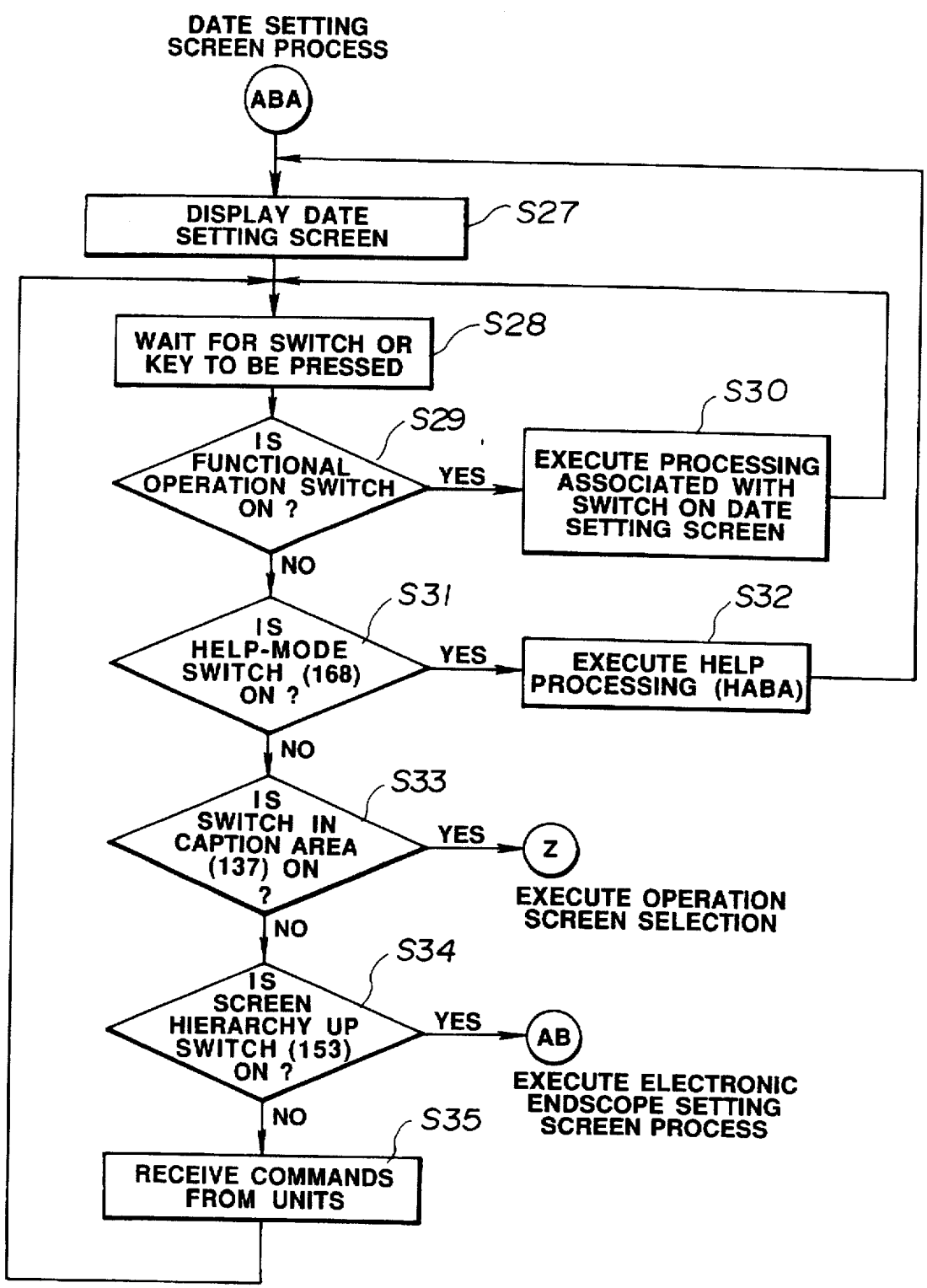
FIG. 41 is a flowchart showing the operations in a date setting screen process.

FIG. 41 shows the operations in the date setting screen process (ABA). The host controller 116 displays the date setting screen at a step S27, and then waits at a step S28 until any operation switch or key in the date setting screen 154 is pressed. If an operation switch is pressed, it is determined at a step S29 whether the pressed switch is a functional operation switch for designating a function in the date setting screen 154. If a functional operation switch is pressed, the host controller 116 advances to a step S30, executes the processing associated with the pressed switch, and then returns to the step S28. If it is determined at the step S29 that a functional operation switch is not pressed, it is determined at a step D31 whether the pressed switch is the Help-mode switch 168. If the Help-mode switch 168 is pressed, the host controller 116 advances to a step S32, executes Help processing (HABA), and then returns to the step S27.

At a step S33, it is determined whether the pressed switch is any one in the caption area 137. If a switch in the caption area 137 is pressed, Operation Screen Selection (Z) shown in FIG. 38 is executed. At a step S34, it is determined whether the screen hierarchy up switch 153 is pressed. If the screen hierarchy up switch 153 is pressed, the host controller 116 returns to the electronic endoscope setting screen process (AB) shown in FIG. 40. If the determination made at any of the steps S29 to S34 is in the negative, the host controller 116 advances to a step S35, executes the command reception from equipment shown in FIG. 39, and then returns to the step S28.

Like the main operation screen 131, even an operation screen of a lower hierarchy; such as, the electronic endoscope setting screen 132 and date setting screen 154 has the caption area 137. Specifically, multiple card-like operation screens are structured hierarchically so that operation screens of lower hierarchies comes immediately under operation screens of higher hierarchies. Card-like hierarchical operation screens are turned sequentially to display or change screens. When any of the operation screen select switches 141 to 145 is selected from the caption area 137 serving as the operation screen selecting section, as if any caption were selected from a file, an operation screen for an intended unit can be displayed regardless of the hierarchy of a current operation screen. The caption area 137 is shaped differently from other operation switches, which is therefore clearly visible and easily identifiable.

When a fiberscope is to be operated, the OES switch 142 in the caption area 137 is pressed to select the fiberscope operation screen 133 shown in FIG. 21. The fiberscope operation screen 133 has operation switches 156 related to a fiberscope. The operation of the light source apparatus 6, air/water supply apparatus 125, or the like is controlled using the operation switches 156.

Figure 42:
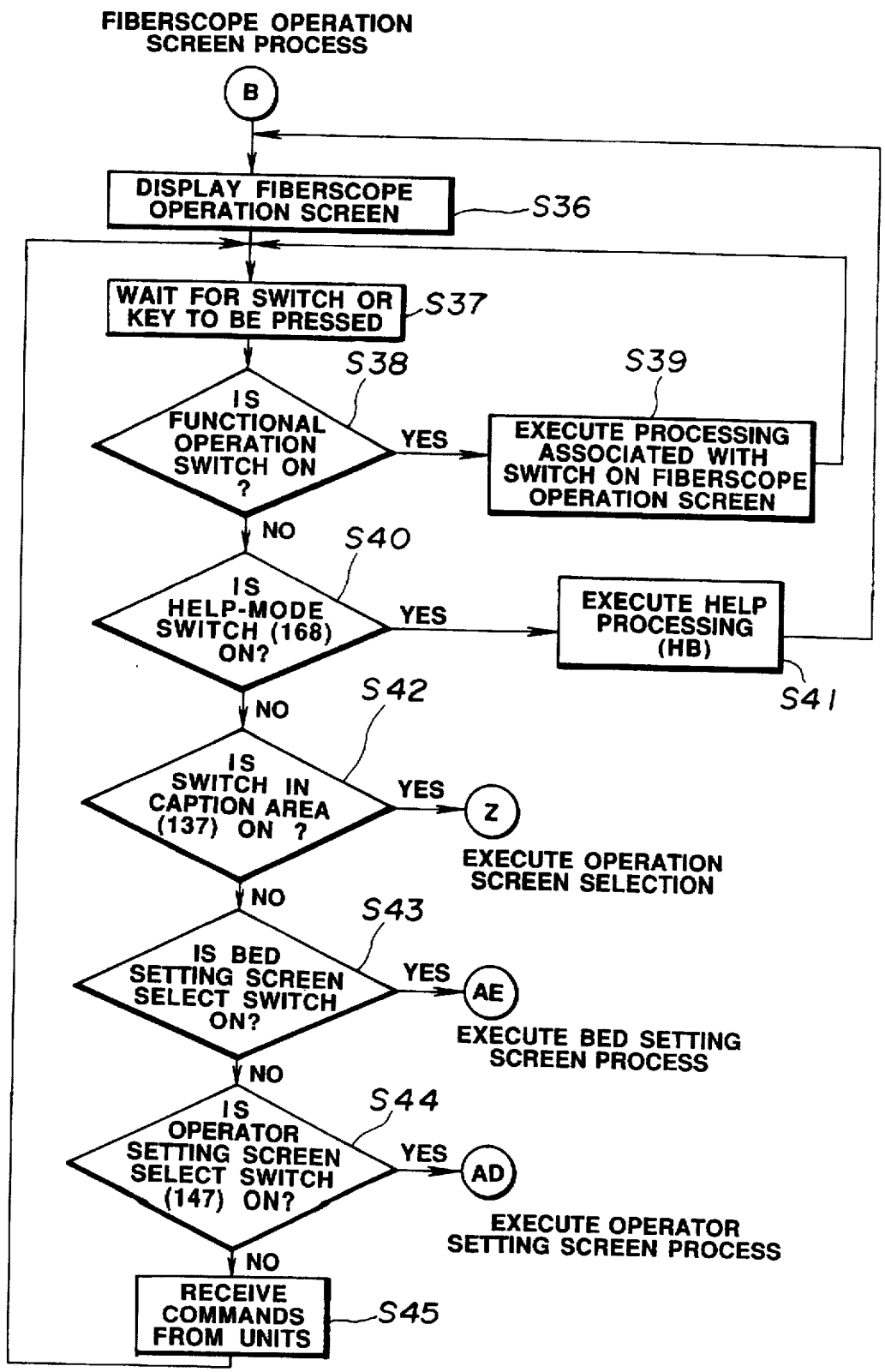
FIGS. 42 and 44 are flowcharts showing the operations in a fiberscope operation screen process.

FIG. 42 shows the operations in a fiberscope operation screen process (B). The host controller 116 displays the fiberscope operation screen at a step S36, and then waits at a step S37 until any operation switch or key in the fiberscope operation screen 133 is pressed. If an operation switch is pressed, it is determined at a step S38 whether the pressed switch is a functional operation switch for designating a function in the fiberscope operation screen 133. If a functional operation switch is pressed, the host controller 116 advances to a step S39, executes the processing associated with the pressed switch, and then returns to the step S37. If any functional operation switch is not pressed at the step S38, it is determined at a step S40 whether the pressed switch is the Help-mode switch 168. If the Help-mode switch 168 is pressed, the host controller 116 advances to a step S41, executes Help processing (HB), and then returns to the step S36.

At a step S42, it is determined whether the pressed switch is any one in the caption area 137. If any switch in the caption area 137 is pressed, Operation Screen Selection (Z) shown in FIG. 38 is executed. At a step S43, it is determined whether the bed setting screen select switch 150 is pressed. If the bed setting screen select switch 150 is pressed, the bed setting screen process (AE) is executed. At a step S44, it is determined whether the operator setting screen select switch 147 is pressed. If the operator setting screen select switch 147 is pressed, the operator setting screen process (AD) is executed. If the determination made at any of the steps S38 to S44 is in the negative, the host controller 116 advances to a step S45, executes the command reception from equipment shown in FIG. 38, and then returns to the step S37.

Figure 43:
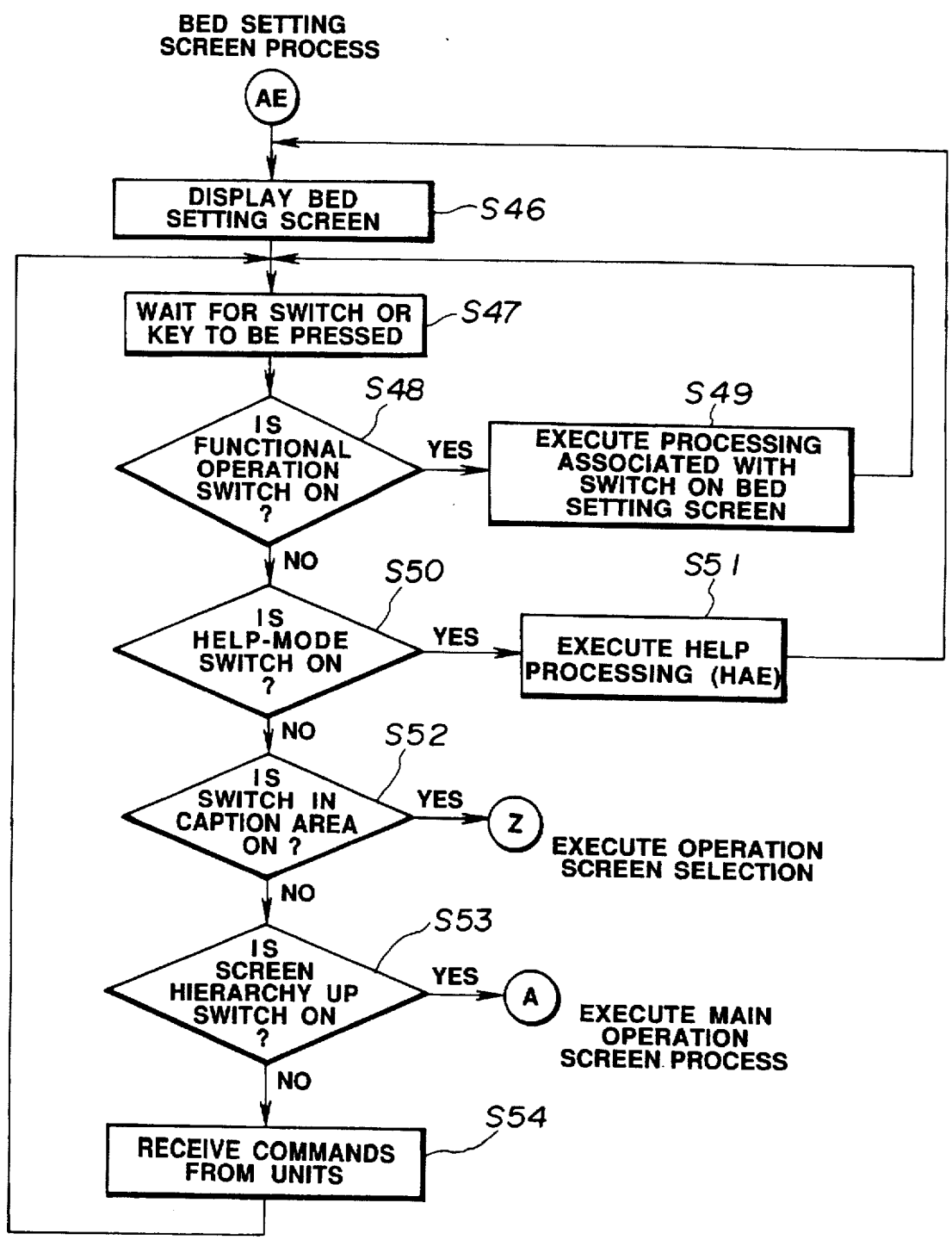
FIG. 43 is a flowchart showing the operations in a bed setting screen process.

FIG. 43 shows the operations in the bed setting screen process (AE). The motor-driven bed 17 can be operated using a motor-driven bed operating section formed in the right lower part of the main operation screen 131 or fiberscope operation screen 133. When a bed setting screen change switch 150 is pressed, the bed setting screen is selected. In the bed setting screen, the position of the motor-driven bed 17 is set for each operator and the set value is stored in memory. The host controller 116 displays the bed setting screen at a step S46, and then waits at a step S47 until any operation switch or key in the bed setting screen is pressed. If an operation switch is pressed, it is determined at a step S48 whether the pressed switch is a functional operation switch for designating a function in the bed setting screen. If a functional operation switch is pressed, the host controller 116 advances to a step S49, executes the processing associated with the pressed switch, and then returns to the step S47. It is determined at a step S48 that any functional operation switch is not pressed, it is determined at a step S50 whether the pressed switch is the Help-mode switch. If the Help-mode switch is pressed, the host controller 116 advances to a step S51, executes Help processing (HAE), and then returns to the step S46.

At a step S52, it is determined whether the pressed switch is any one in the caption area. If any switch in the caption area is pressed, Operation Screen Selection (Z) shown in FIG. 38 is executed. At a step S53, it is determined whether the screen hierarchy up switch is pressed. If the screen hierarchy up switch is pressed, the host controller 116 returns to the main operation screen process (A) in FIG. 37. If the determination made at any of the steps S48 to S53 is in the negative, the host controller 116 advances to a step S54, executes the command reception from equipment shown in FIG. 39, and then returns to the step S47.

Figure 44:
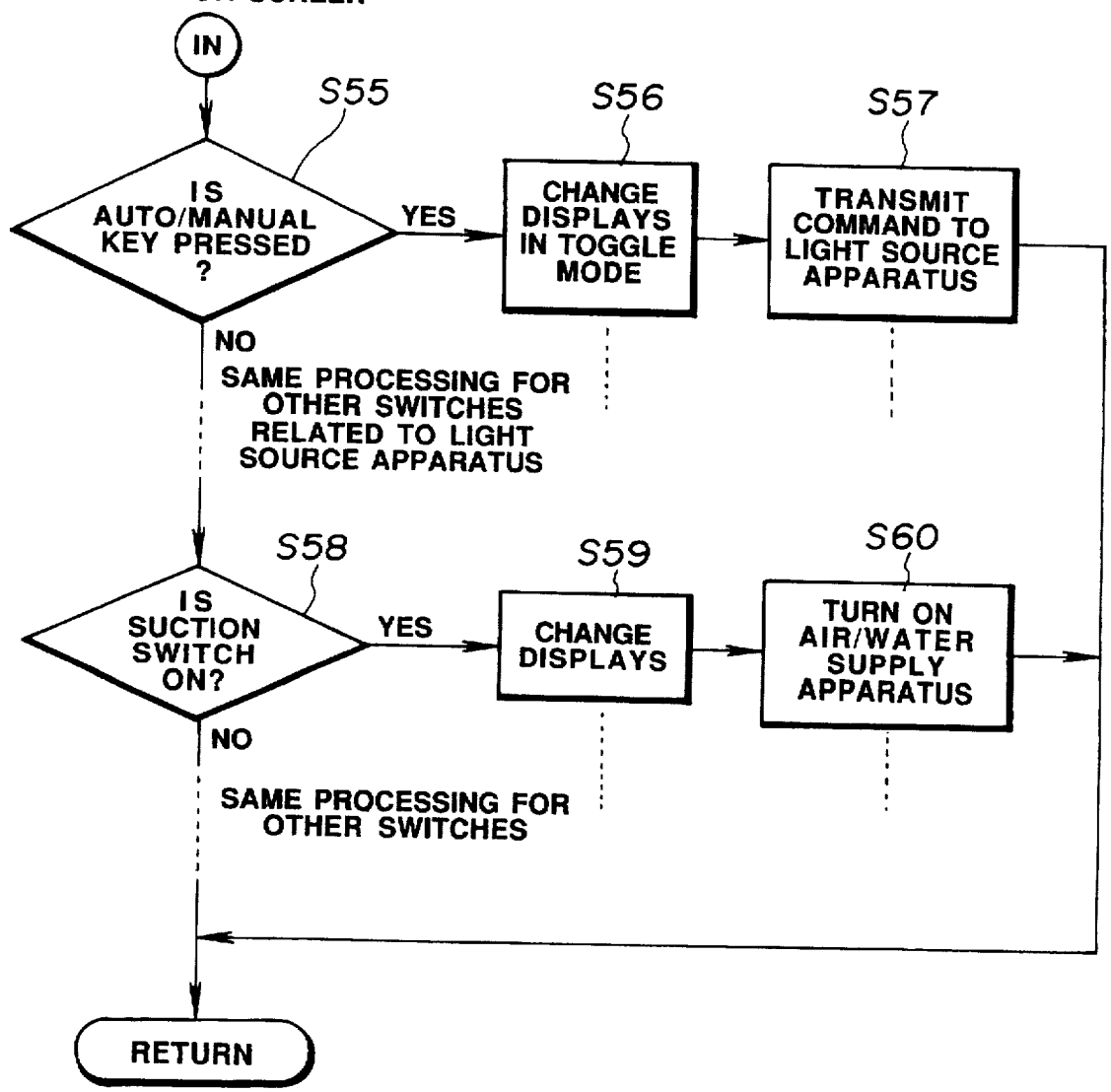

FIG. 44 shows the processing operation associated with a switch or key in the fiberscope operation screen which is executed at the step S39. If the AUTO/MANUAL key for changing modes for adjusting a quantity of light in the light source apparatus, which is located in the right center of the fiberscope operation screen 133, is pressed, the host controller 116 determines at a step S55 whether the AUTO/MANUAL key is pressed. The host controller 116 changes the display of the AUTO/MANUAL key to AUTO or MANUAL in toggle mode at a step S56, and then transmits a mode change command to the light source apparatus 6 at a step S57. Either automatic or manual mode is thus selected for adjusting a quantity of light in the light source apparatus. The same processing is performed for other switches related to the light source apparatus in the fiberscope operation screen 133.

Even when any of the operation switches related to peripheral equipment, which are located in the lower left part of the fiberscope operation screen 133, is pressed, almost the same processing as that mentioned above is performed. For example, the SUCTION switch designating suction is pressed, the host controller 116 determines at a step S58 whether the SUCTION switch is pressed. At a step S59, the display of the SUCTION switch is changed to indicate an on state. At a step S60, a command saying that the suction pump 87 should be turned on is transmitted to the air/water supply apparatus 125. Suction is then carried out. The same processing is performed for other operation switches.

When the VTR 81 is to be used, the AUX switch 143 in the caption area 137 is pressed to select an external video unit operation screen 134 shown in FIG. 22. The external video unit operation screen 134 has operation switches 157 for the VTR 81. The operation of the VTR 81 is controlled using the operation switches 157.

Figure 45:
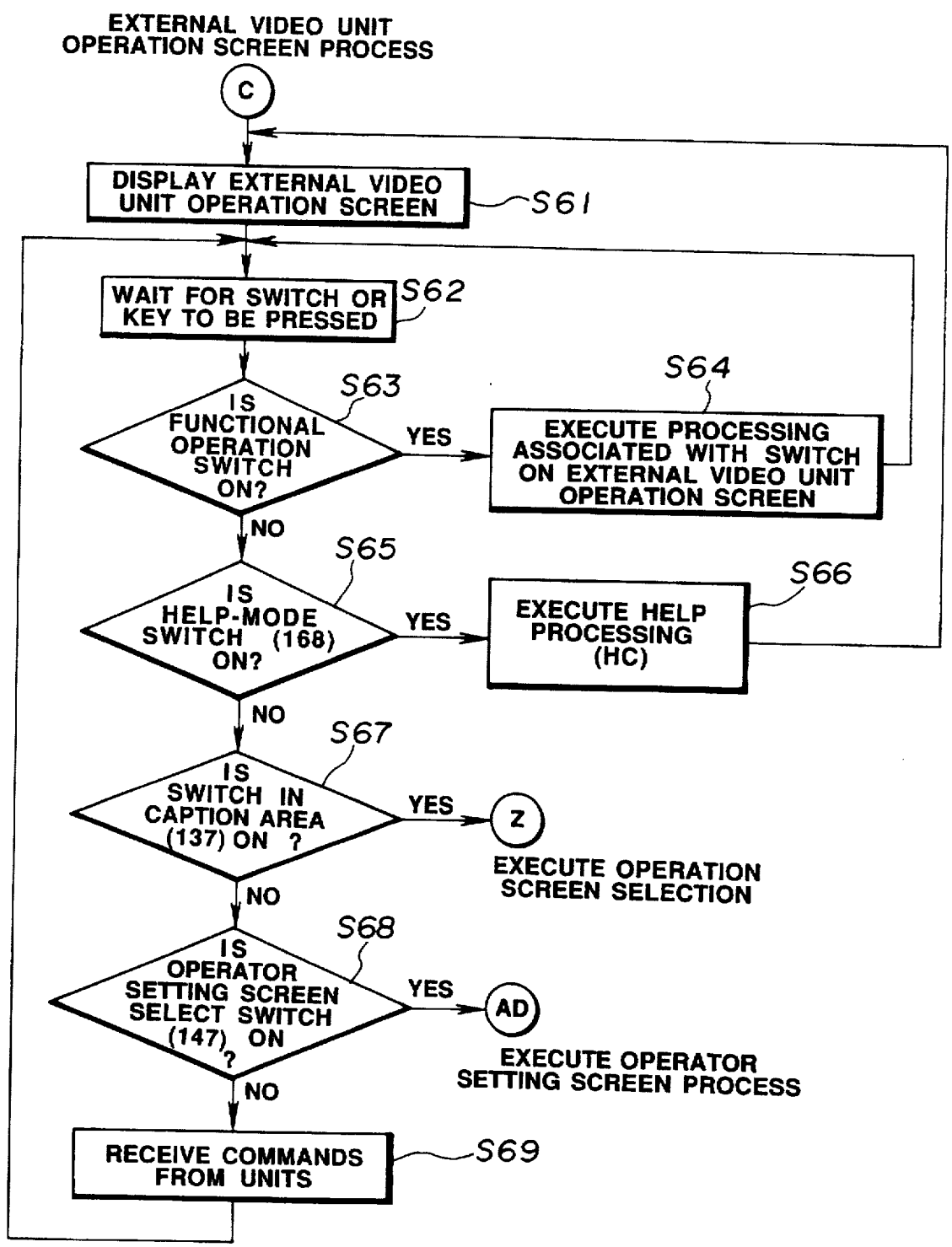
FIGS. 45 and 46 are flowcharts showing the operations in an external video unit operation screen process.

FIG. 45 shows the operations in an external video unit operation screen process (C). The host controller 116 displays the external video unit operation screen at a step S61, and then waits at a step S72 until any operation switch or key in the external video unit operation screen 134 is pressed. When the operation switch is pressed, it is determined at a step S63 whether the pressed switch is a functional operation switch for designating a function in the external video unit operation screen 134. If a functional operation switch is pressed, the host controller 116 advances to a step S64, executes the processing associated with the pressed switch, and then returns to the step S62. If it is determined at the step S63 that an functional operation switch is not pressed, it is determined at a step S65 whether the pressed switch is the Help-mode switch 168. If the Help-mode switch 168 is pressed, the host controller 116 advances to a step S66, executes Help processing (HC), and then returns to the step S61.

It is then determined at a step S67 whether the pressed switch is any one in the caption area 137. If any switch in the caption area 137 is pressed, Operation Screen Selection (Z) in FIG. 38 is executed. At a step S68, it is determined whether the operator setting screen select switch 147 is pressed. If the operator setting screen select switch 147 is pressed, the operator setting screen process (AD) is executed. If the determination made at any of the steps S63 to S68 is in the negative, the host controller 116 advances to a step S69, executes the command reception from equipment shown in FIG. 39, and then returns to the step S62.

Figure 46:
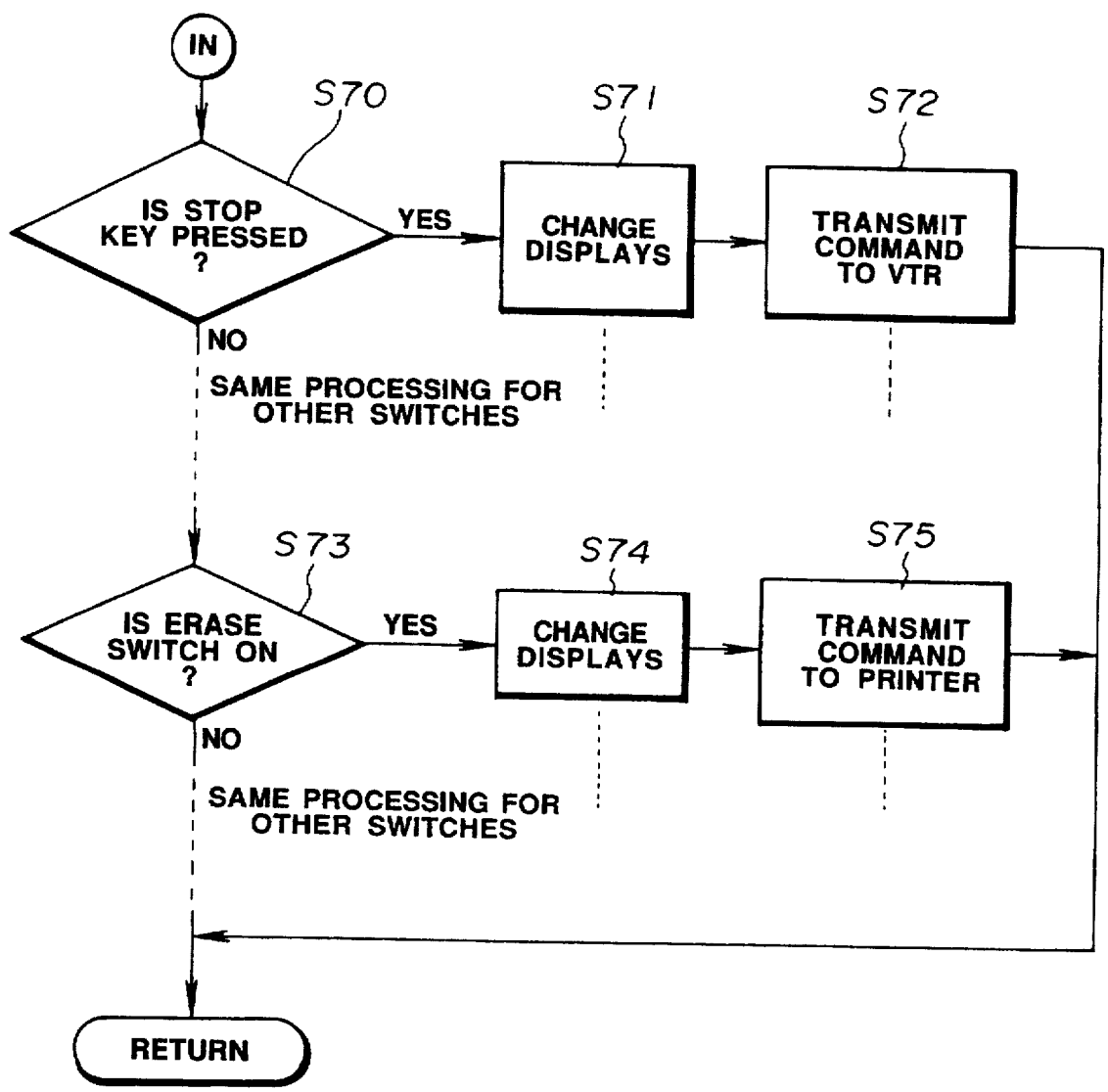

FIG. 46 shows the processing operation associated with a switch or key in the external video unit operation screen which is executed at the step S64. Assuming that the STOP key is pressed among the VTR operation switches located in the lower right part of the external video unit operation screen 134, the host controller 116 determines at a step S70 whether the STOP key is pressed. At a step S71, the display of the STOP key is changed to indicate an on state. At a step S72, a stop command is transmitted to the VTR 81. The VTR then stops. The same processing is performed for other VTR-related switches in the external video unit operation screen 134.

When any of the operation switches related to a video printer, which are located in the lower left part of the external video unit operation screen 134, is pressed, almost the same processing is performed. Assuming that the ERASE key for erasing data is pressed, the host controller 116 determines at a step S73 whether the ERASE key is pressed. At a step S74, the display of the ERASE key is changed to indicate an on state. At a step S75, an erasion command is transmitted to the video printer 82. Data is then erased from the memory of the video printer 82. The same processing is performed for other operation switches.

For using the heat probe unit 23, the HEAT PROBE switch 144 in the caption area 137 is pressed to select the heat probe unit operation screen 135 shown in FIG. 23.

Figure 47:
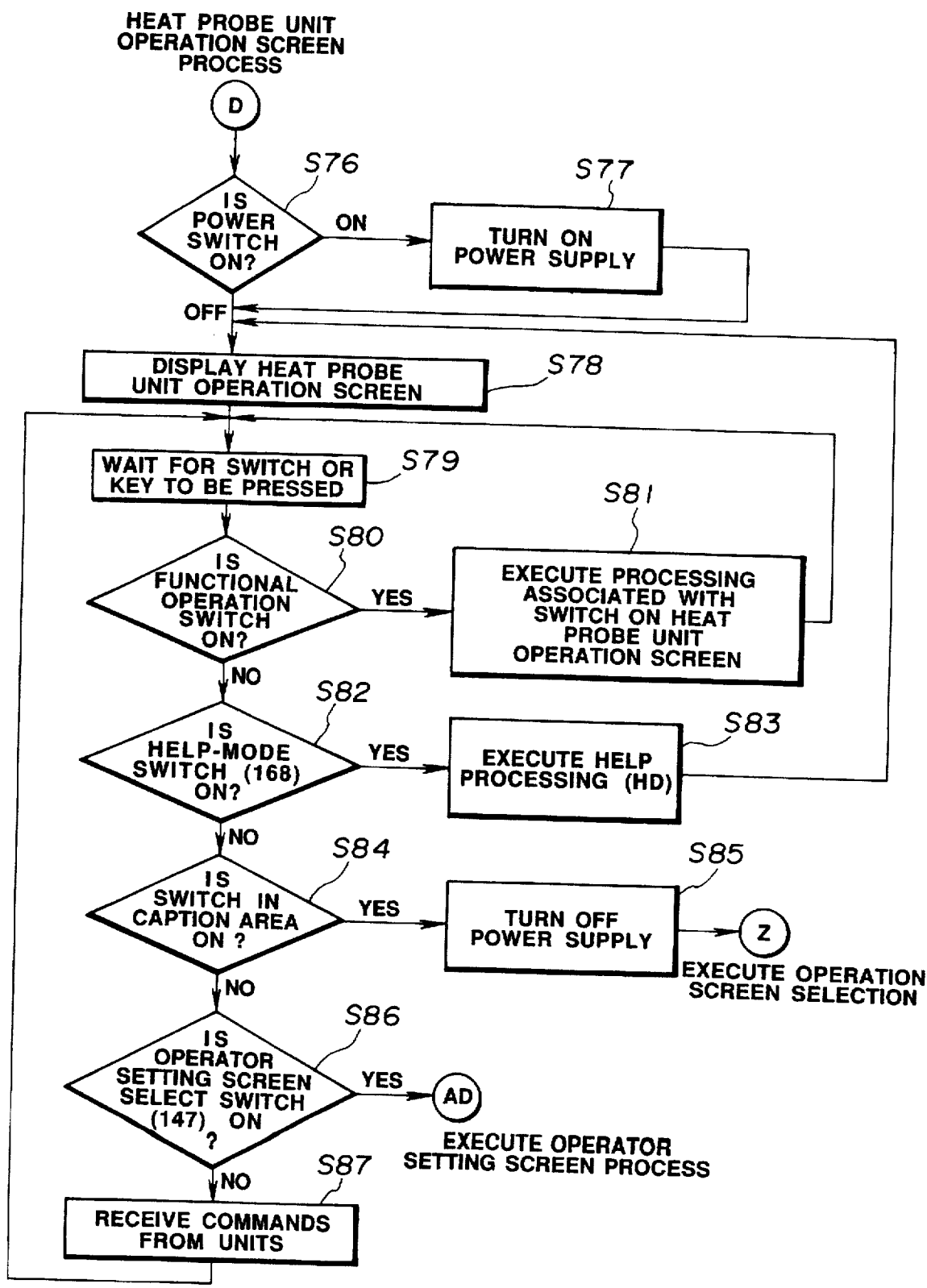
FIGS. 47 and 48 are flowcharts showing the operations in a heat probe unit operation screen process.

FIG. 47 shows the operations in the heat probe unit operation screen process (D). The host controller 116 references the data stored in a memory or the like to see if the power supply of the heat probe unit 23 was on during the previous display of the heat probe unit operation screen 135. If the power supply was on, the host controller 116 advances to a step S77, turns on the power supply of the heat probe unit 23, and then passes to a step S78. If the power supply was off, the host controller 116 advances from the step S76 to the step S78 as it is.

The host controller 116 displays the heat probe unit operation screen at the step S78, and then waits at a step S79 until any operation switch in the heat probe unit operation screen 135 is pressed. When an operation switch is pressed, it is determined at a step S80 whether the pressed switch is a functional operation switch for designating a function in the heat probe unit operation screen 135. If a functional operation switch is pressed, the host controller 116 advances to a step S81, executes the processing associated with the pressed switch, and then returns to the step S79. If it is determined at the step S80 that a functional operation switch is not pressed, it is determined at a step S82 whether the pressed switch is the Help-mode switch 168. If the Help-mode switch 168 is pressed, the host controller 116 advances to a step S83, executes Help processing (HD), and then returns to the step S78.

At a step S84, it is determined whether the pressed switch is any one in the caption area 137. If any switch in the caption area 137 is pressed, the host controller 116 advances to a step S85, turns off the power supply of the heat probe unit 23, and then executes Operation Screen Selection (Z) shown in FIG. 38. At a step S86, it is determined whether the operator setting screen select switch 147 is pressed. If the operator setting screen select switch 147 is pressed, the operator setting screen process (AD) is executed. If the determination made at any of the steps S80 to S86 is in the negative, the host controller 116 advances to a step S87, executes the command reception from equipment shown in FIG. 39, and then returns to the step S79.

Figure 48:
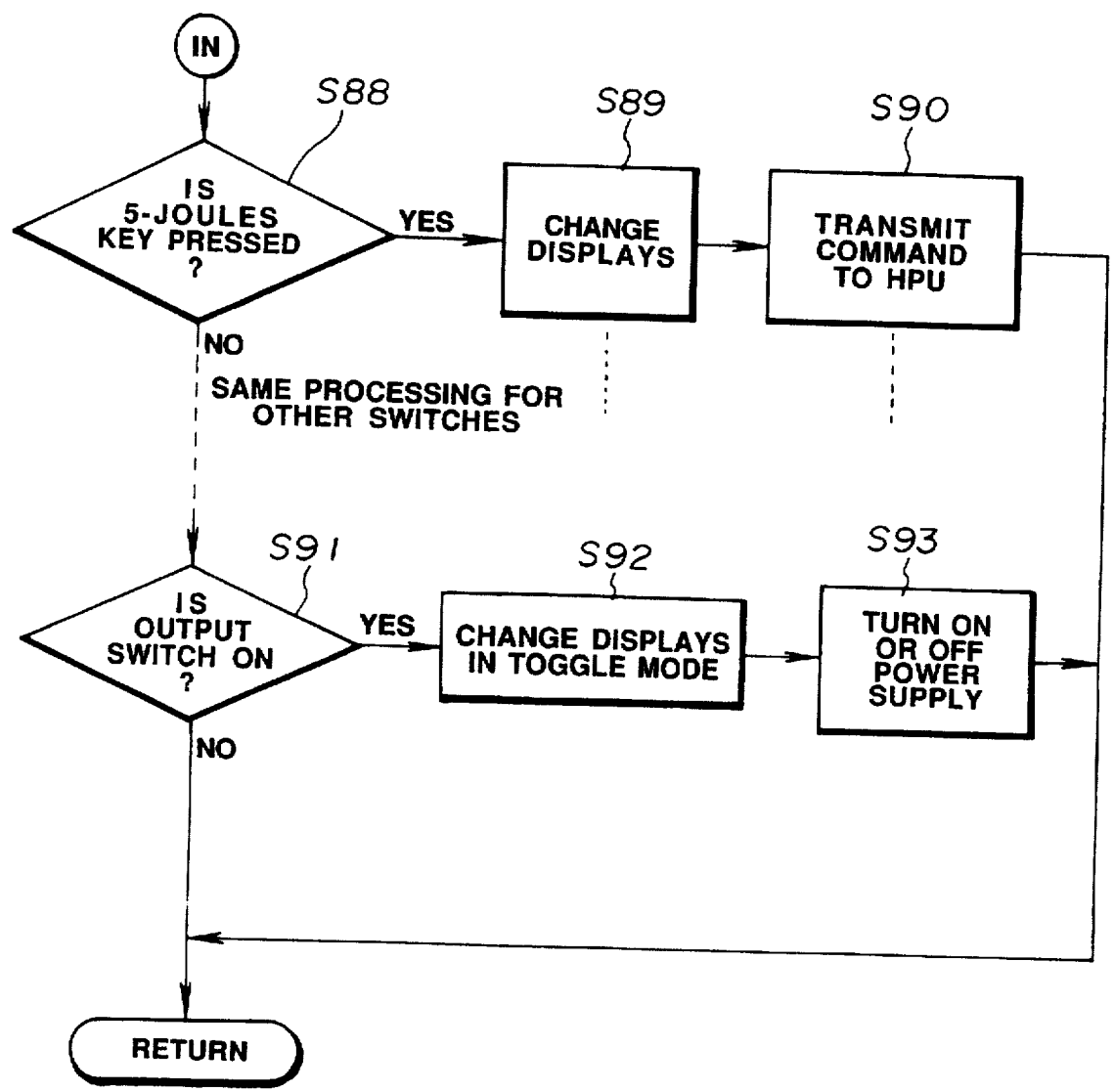

FIG. 48 shows the processing operation associated with a switch or key in the heat probe unit operation screen which is executed at the step S81. Assuming that a 5 JOULES key is pressed among the output calorie setting switches for the heat probe unit which are located in the left center of the heat probe unit operation screen 135, the host controller 116 determines at a step S88 whether the 5 JOULES key is pressed. At a step S89, the display of the 5 JOULES key is changed to indicate an on state. At a step S90, an output calorie setting command is transmitted to the heat probe unit 23. With the command, the output of the heat probe unit is set to a minimum value (5 joules). The same processing is performed for other output calorie setting switches and water value setting switches in the heat probe unit operation screen 135.

When an OUTPUT switch located at the right lower corner of the heat probe unit operation screen 135 is pressed, almost the same processing is performed. The host controller 116 determines at a step S91 whether the OUTPUT switch is pressed. At a step S92, the display of the OUTPUT switch is changed to indicate an on or off state in toggle mode. At a step S93, the power supply of the heat probe unit 23 is turned on or off.

For using the electric cautery unit 28, the DIATHERMY switch in the caption area 137 is pressed to select the electric cautery unit operation screen 136 shown in FIG. 24. The electric cautery operation screen 136 has a waveform select area 158 for selecting a waveform of an output of an electric cautery and a waveform display area 159 for displaying output waveforms. When an output waveform is selected from the waveform select area 158, the switch of the selected waveform changes in color so that the selected waveform can be verified. The display of the waveform display area 159 changes accordingly. The current output state of the electric cautery can thus be identified effortlessly.

Figure 49:
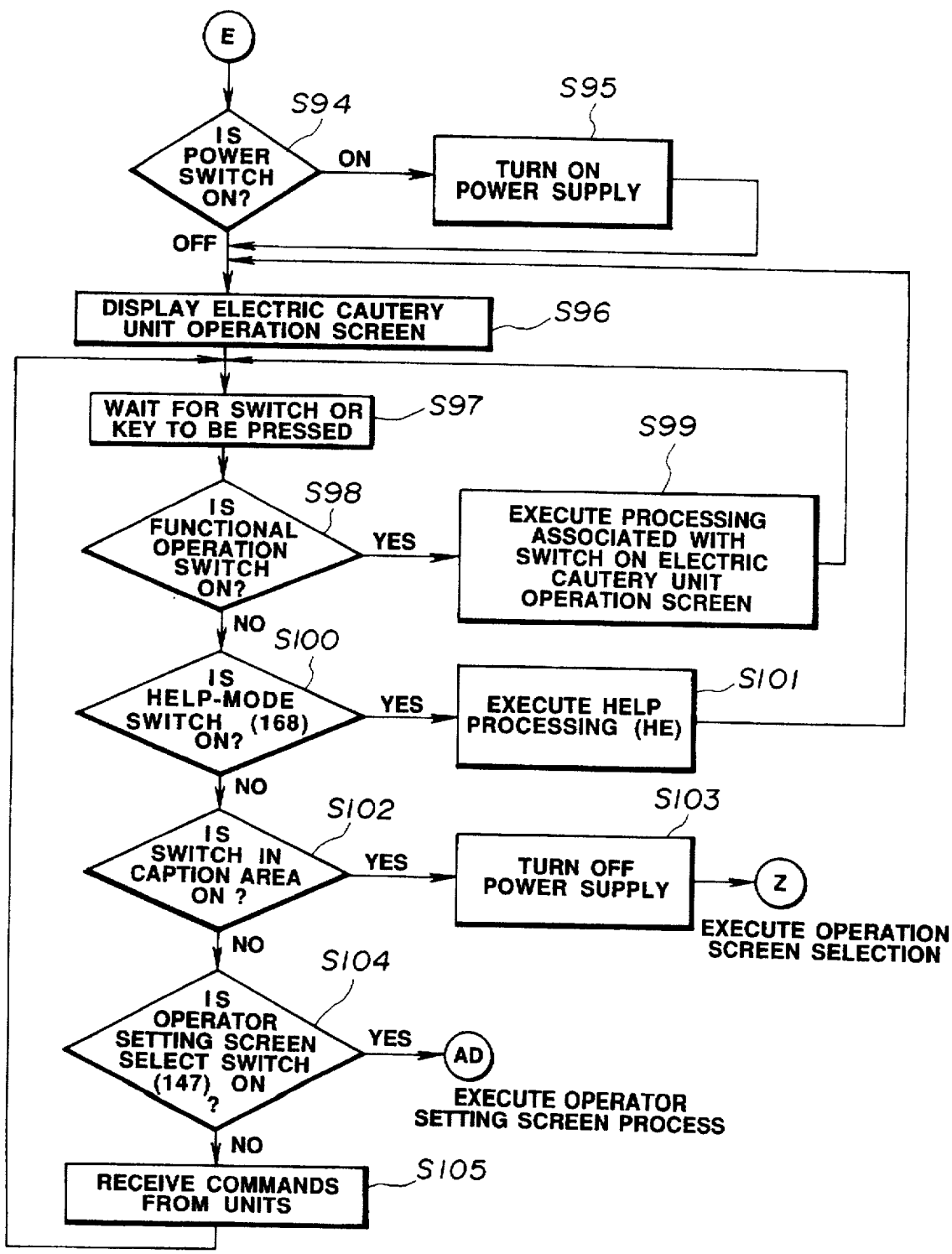
FIGS. 49 and 50 are flowcharts showing the operations in an electric cautery unit operation screen process.

FIG. 49 shows the operations in the electric cautery unit operating screen process (E). Similarly to the process of the heat probe unit operation screen, the host controller 116 references the data stored in a memory or the like at a step S94 to see if the power supply of the electric cautery unit 28 was on during the previous display of the electric cautery unit operation screen 136. If the power supply was on, the host controller 116 advances to a step S95, turns on the power supply, and then passes to a step S96. If the power supply was off, the host controller 116 passes from the step S94 to the step S96 as it is.

The host controller 116 displays the electric cautery unit operation screen at the step S96, and waits at a step S97 until any operation switch or key in the electric cautery unit operation screen 136 is pressed. When an operation switch is pressed, it is determined at a step S98 whether the pressed switch is a functional operation switch for designating a function in the electric cautery unit operation screen 136. If a functional operation switch is pressed, the processing associated with the pressed switch is executed at a step S99. The host controller 116 then returns to the step S97. If it is determined at the step S98 that a functional operation switch is not pressed, it is determined at a step S100 whether the pressed switch is the Help-mode switch 168. If the Help-mode switch 168 is pressed, the host controller 116 advances to a step S101, executes Help processing (HE), and then returns to the step S96.

At a step S102, it is determined whether the pressed switch is any one in the caption area 137. If a switch in the caption area 137 is pressed, the host controller 116 advances to a step S103, turns off the power supply of the electric cautery unit 28, and then executes Operation Screen Selection (Z) shown in FIG. 38. At a step S104, it is determined whether the operator setting screen select switch 147 is pressed. If the operator setting screen select switch 147 is pressed, the operator setting screen process (AD) is executed. If the determination made at any of the steps S98 to S104 is in the negative, the host controller 116 advances to a step S105, executes the command reception from equipment shown in FIG. 39, and then returns to the step S97.

Figure 50:
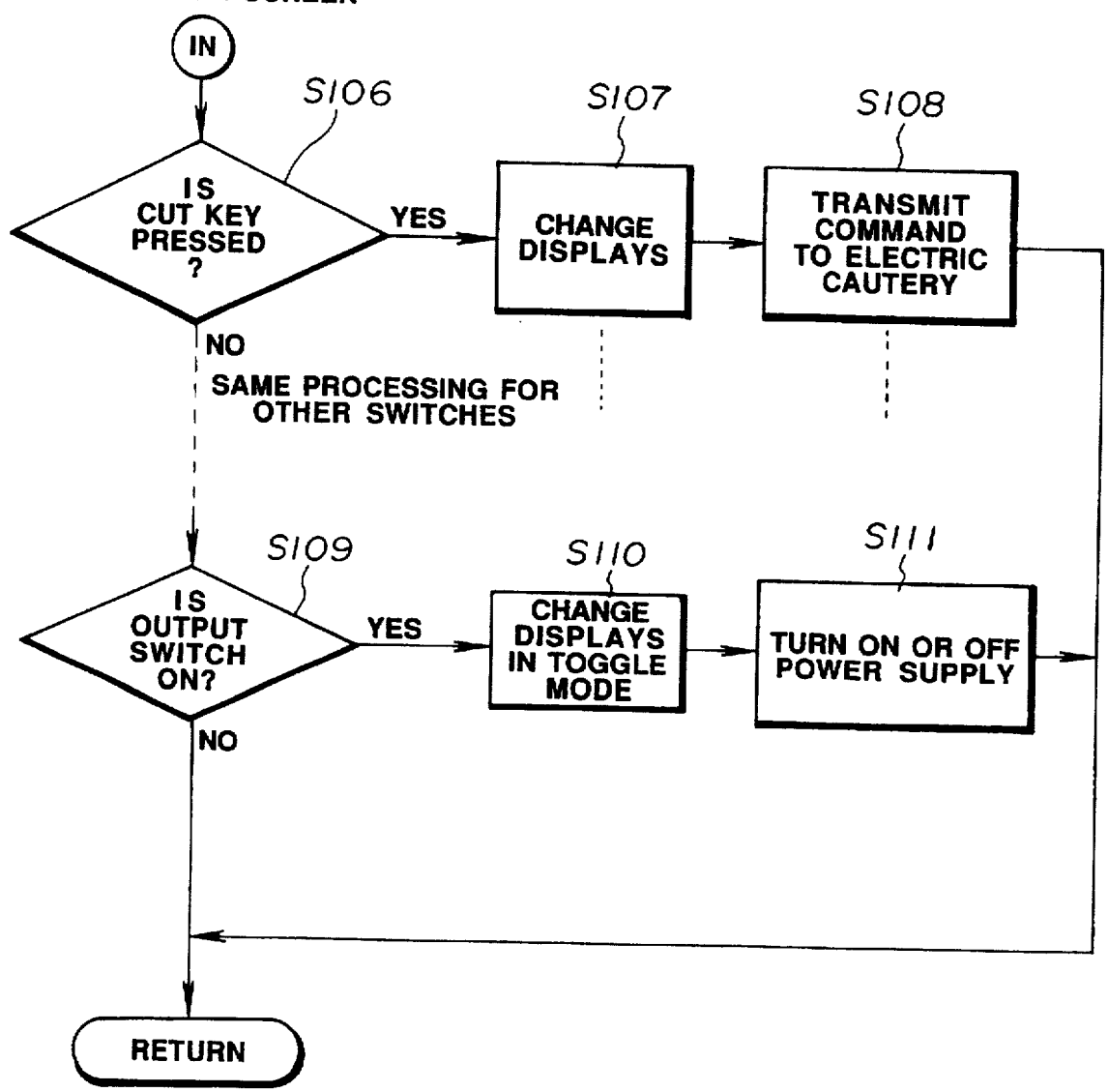

FIG. 50 shows the processing operation associated with a switch or key in the electric cautery unit operation screen which is executed at the step S99. Assuming that a CUT key is pressed among the mode change switches for the electric cautery unit which are located in the lower part of the electric cautery unit operation screen 136, the host controller 116 determines at a step S106 whether the CUT key is pressed, changes the display of the switch to indicate an on state at a step S107, and then transmits a command, which instructs to select a Cut-mode (resection mode) output waveform, to the electric cautery unit 28 at a step S108. The output of the electric cautery unit 28 is then set to the Cut mode. The same processing is performed on other mode setting switches or an output setting switch in the electric cautery unit operation screen 136.

Even when the OUTPUT switch located in the lower right corner of the electric cautery unit operation screen 136 is pressed, almost the same processing s executed. The host controller 116 determines at a step S109 whether the OUTPUT switch is pressed, changes the display of the switch to indicate an on or off state at a step S110, and turns on or off the power supply of the electric cautery unit 28.

Delineated switches in each of the main operation screen 131, electric endoscope screen 132, fiberscope operation screen 133, external video unit operation screen 134, heat probe unit operation screen 135, and electric cautery unit operation screen 136 are grouped by functional fields. The background colors of switches are different among functions. The switches belonging to the same functional field have the same background color. This helps recognize the function of an operation switch easily.

A setting state display area 160 for displaying various set values and operating states for a unit is formed in the main operation screen 131 or fiberscope operation screen 133. The setting state display area 160 consists of an analog indicator 161 for indicating an approximate value depending on the length of a bar graph and a digital indicator 162 for indicating an exact value in the digital form. In the setting state display area 160, an analog value and a digital value are indicated according to a set value entered or selected by an operator. As for the indication by the analog indicator 161, for example, the index gets longer as a value increases, or the color varies depending on a value. Analog indication and digital indication are thus used in conjunction. The analog indication permits recognition of a value with excellent intuitive visibility, while the digital indication offers an exact value with high precision. Various values related to a unit can be set reliably.

The foregoing setting state display area may be replaced with a setting state display area 163, in which stepwise switches serve as indicators, in the heat probe unit operation screen 135 or electric cautery unit operation screen 136. As for the setting state display area 163, when a switch corresponding to a set value is pressed directly, the switch changes in color to indicate a currently-set state. Since the setting state display area 163 is a section in which switches cum indicators are arranged stepwise with incremental values. The setting state display area 163 therefore permits excellent visibility in recognizing a setting state, and enables direct selection of a desired set value. Setting can therefore be performed instantaneously with good operability.

Figure 28:
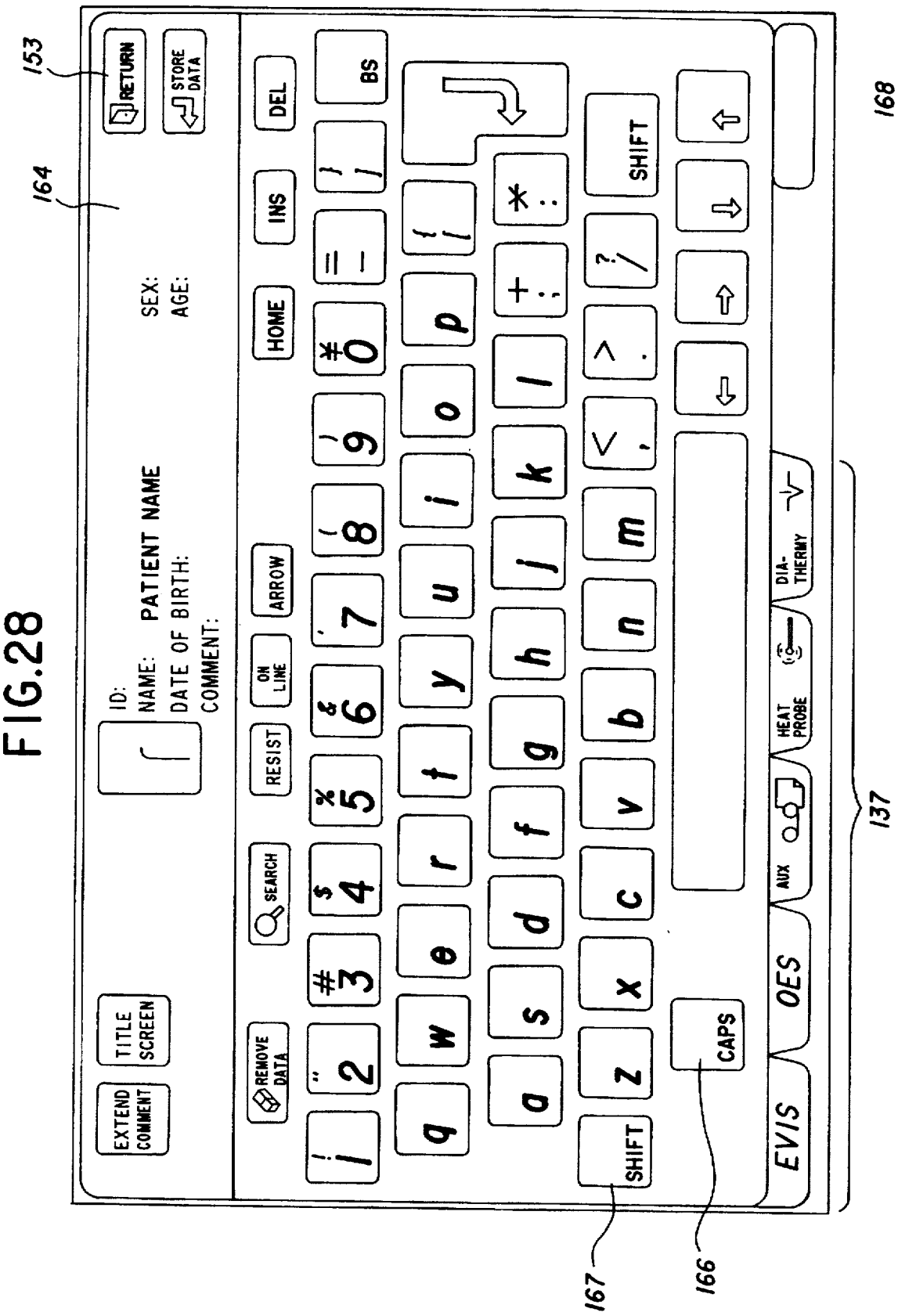
FIGS. 28 and 29 are explanatory diagrams showing a patient data input screen for use in entering patient data.
Figure 29:
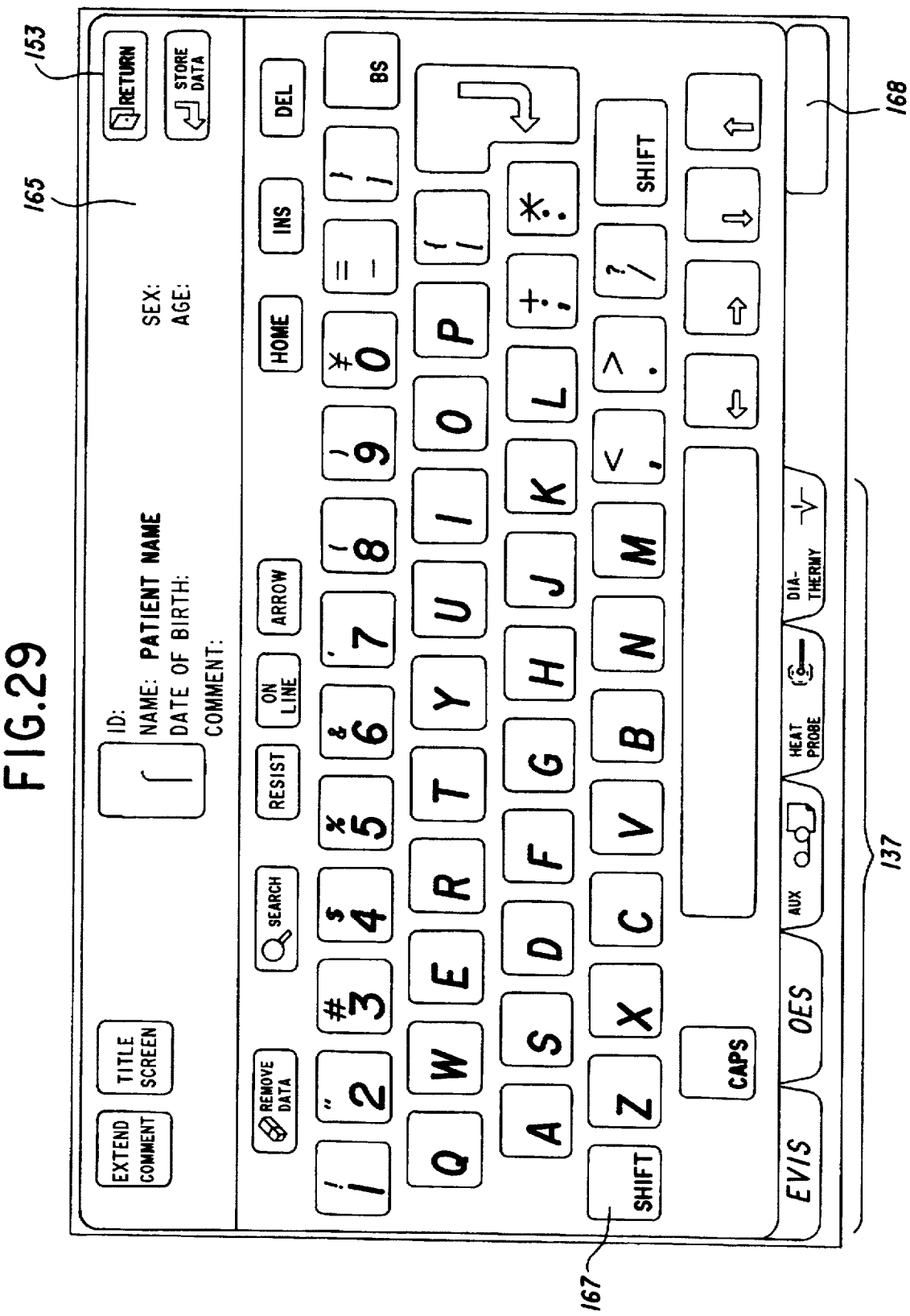

When the patient data input screen select switch 148 in the main operation screen 131 is pressed, the patient data input screen (1) 164 shown in FIG. 28 is selected. Keys displayed in the patient data input screen (1) 164 are pressed to enter patient data with any lower-case alphabets and numerical characters. For entering any upper-case characters, a CAPS key 166 is pressed to designate a patient data input screen (2) 165 shown in FIG. 29. In the patient data input screen (2) 165, the displays of keys are upper-case characters so that patient data can be entered with any upper-case alphabets and numerical characters. In either the patient data input screen 164 or 165, when a SHIFT key 167 is pressed, the characters displayed in upper parts of keys can be entered. The patient data input screens (1) 164 and (2) 165 have the same functions as normal keyboards and can therefore be used to enter data in the same manner as normal keyboards. After data has been entered, the screen hierarchy up switch 153 is pressed to return to the main operation screen 131.

Figure 51:
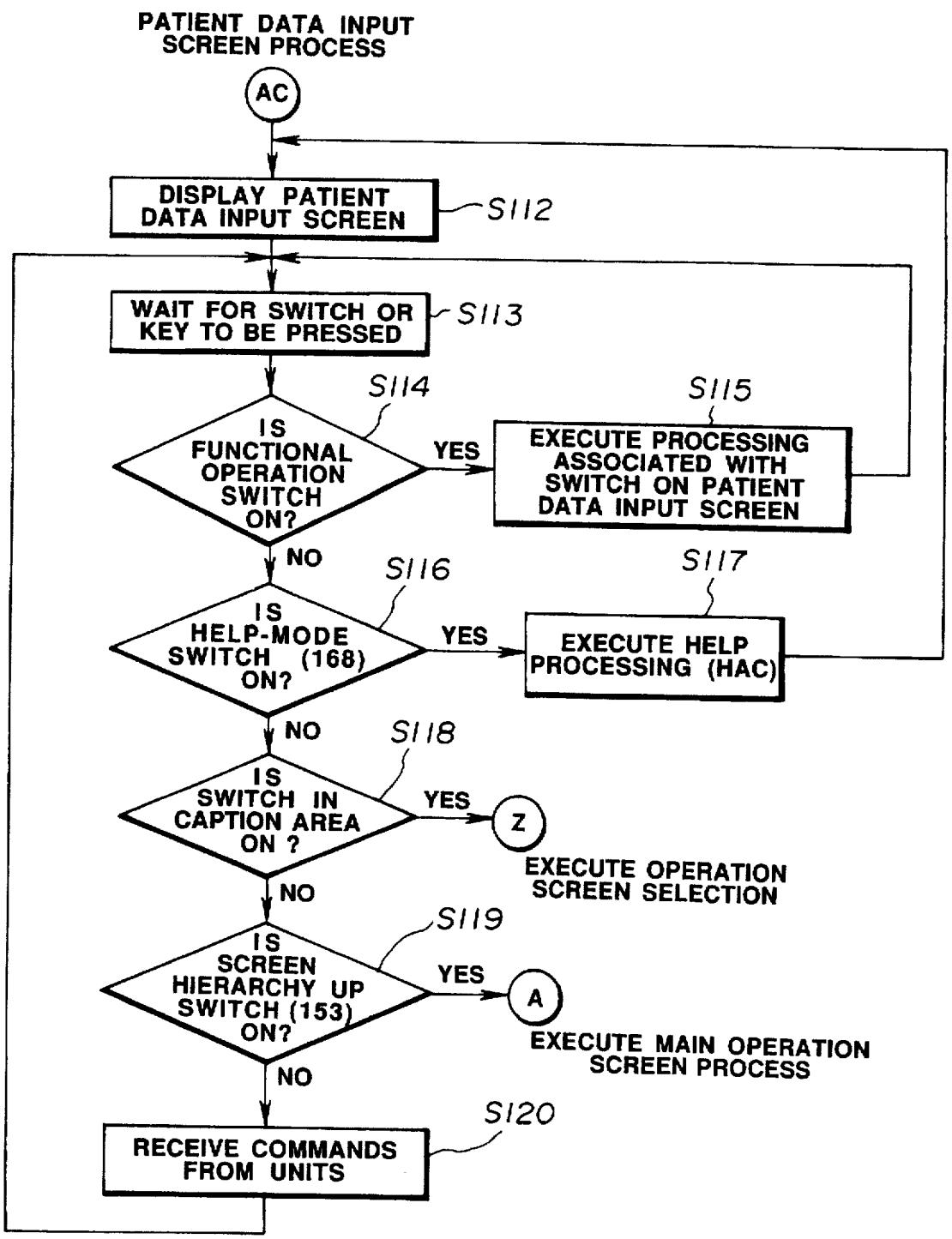
FIGS. 51 and 52 are flowcharts showing the operations in a patient data input screen process.

FIG. 51 shows the operations in the patient data input screen process (AC). The host controller 116 displays the patient data input screen at a step S112, and then waits at a step S113 until any operation switch in the patient data input screen (1) 164 or (2) 165 is pressed. If an operation switch is pressed, it is determined at a step S114 whether the operation switch is a functional operation switch for designating a function in the patient data input screen. If a functional operation switch is pressed, the host controller 116 advances to a step S115, executes the processing associated with the pressed switch, and then returns to the step S113. If it is found at the step S114 that a functional operation switch is not pressed, it is determined at a step S116 whether the pressed switch is the Help-mode switch 168. If the Help-mode switch is pressed, the host controller 116 advances to a step S117, executes Help processing (HAC), and then returns to the step S112.

At a step S118, it is determined whether the pressed switch is any one in the caption area 137. If any switch in the caption area 137 is pressed, Operation Screen Selection (Z) shown in FIG. 38 is executed. At a step S119, it is determined whether the screen hierarchy up switch 153 is pressed. If the screen hierarchy up switch is pressed, the host controller 116 returns to the main operation screen process (A) shown in FIG. 37. If the determination made at any of the steps S114 to S119 is in the negative, the host controller 116 advances to a step S120, executes the command reception for equipment shown in FIG. 39, and then returns to the step S113.

Figure 52:
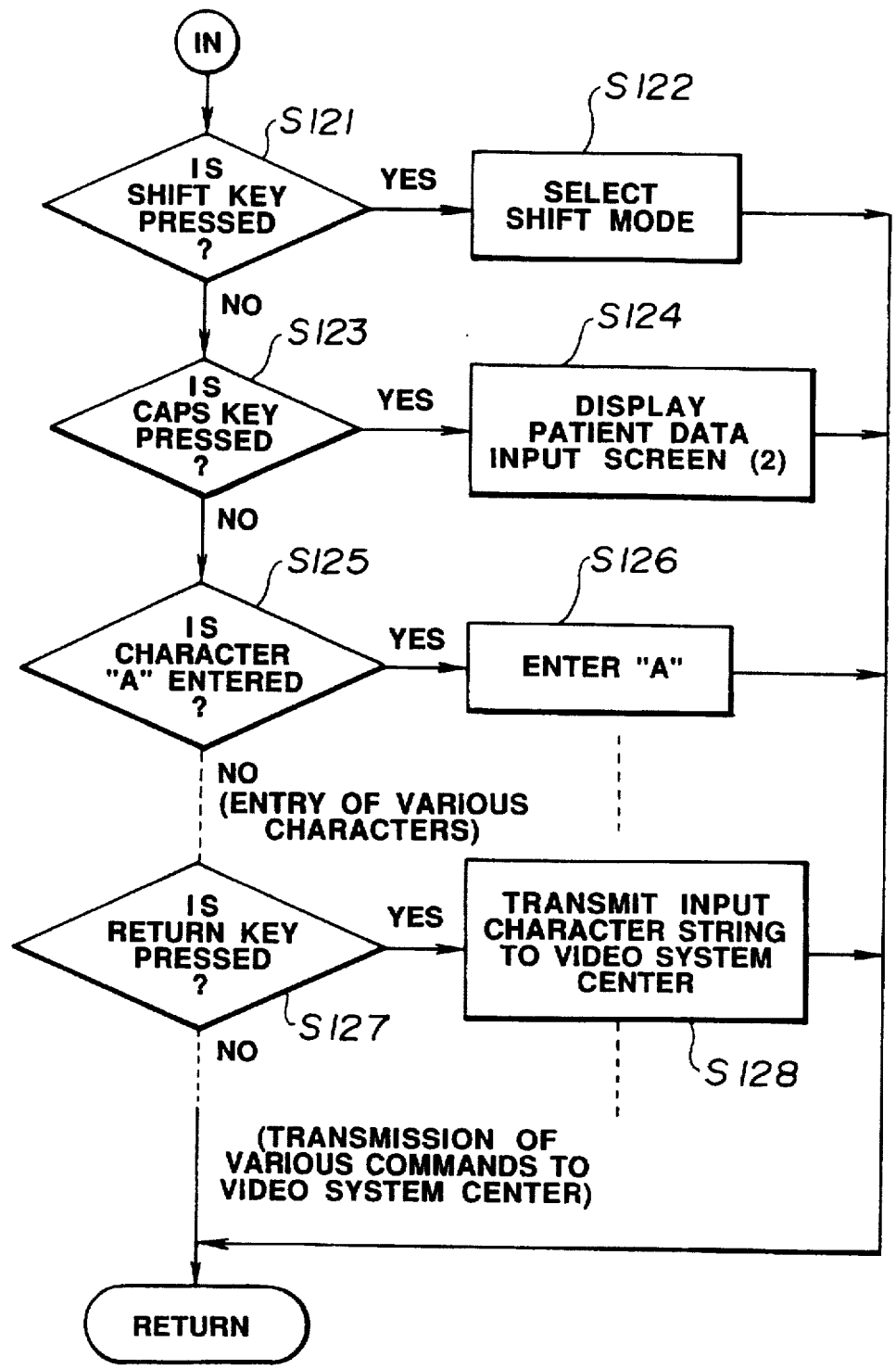

FIG. 52 shows the processing operation associated with a switch or key in the patient data input screen. The host controller 116 determines at a step S121 whether the SHIFT key 167 is pressed in the patient data input screen (1) 164 or (2) 165. If the SHIFT key 167 is pressed, the host controller 116 advances to a step S122, and selects a shift mode enabling input of characters written in the upper parts of keys. At a step S123, it is determined whether the CAPS key 166 is pressed in the patient data input screen (1) 164. If the CAPS key 166 is pressed, the host controller 116 advances to a step S124, and changes the screen to the patient data input screen (2) 165. At a step S125, it is determined whether an A key is pressed. If the pressed key is the A key, the host controller 116 advances to a step S126 and inputs A. The same processing is performed for other characters. At a step S127, it is determined whether the return key denoted with an arrow and located in the right center of the patient data input screen is pressed. If the return key is pressed, the host controller 116 advances to a step S128, and transmits an input character string to the video system center 5. Even when other keys located in the top of the patient data input screen and used to transmit various commands are pressed, the commands associated with the pressed keys are transmitted according to the foregoing sequence.

Figure 30:
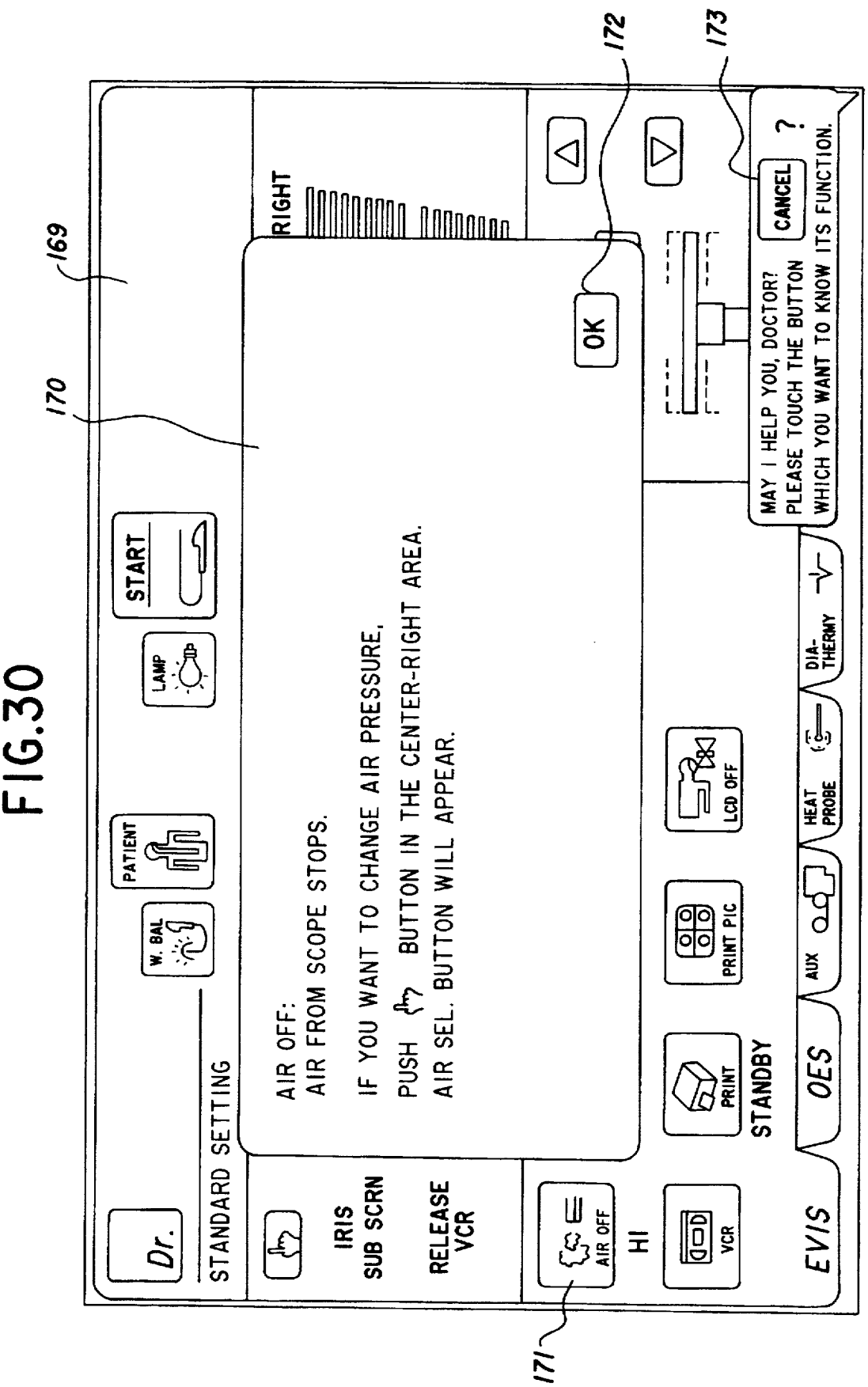
FIG. 30 is an explanatory diagram showing a Help-mode screen in a Help mode for explaining operations of the control panel.

The Help-mode switch 168 is formed at the lower right corner of each of the main operation screen 131, electronic endoscope setting screen 132, fiberscope operation screen 133, external video unit operation screen 134, heat probe unit operation screen 135, and electric cautery unit operation screen 136. When the Help-mode switch 168 is pressed, the Help-mode screen 169 for explaining how to use a unit as shown in FIG. 30 appears. The Help-mode screen 169 is displayed with an explanation display area 170 overlapped on a normal operation screen. FIG. 30 shows a screen appearing when an AIR OFF switch 171 is pressed after the Help-mode switch 168 is pressed in the main operation screen 131. In the Help mode, the explanation appearing in the explanation display section 170 is the explanation of an operation actuated when a switch is pressed but not the one of an operation associated with an operation switch.

The explanation display section 170 is deleted by pressing a verification switch 172 located in the lower right part thereof. If any other operation switch is pressed, the explanation of the switch appears in the explanation display area 170. In the Help mode, a CANCEL switch 173 is located at the lower right corner. When the CANCEL switch 173 is pressed, the Help mode is released to return to a normal operation mode or operation screen.

FIG. 53 shows the operations in Help processing (HA). The aforesaid Help processing in each operation screen is substantially the same as that shown in FIG. 53. The Help processing (HA) activated in the main operation screen 131 will be described as an example.

The host controller 116 displays the Help-mode screen 169 at a step S129, and waits at a step S30 until an operation switch or key in the screen is pressed. At a step S131, it is determined whether the CANCEL switch 173 is pressed. If the CANCEL switch 173 is pressed, the Help mode is released to return to an original operation screen. At a step S132, it is determined whether any other switch is pressed. At a step S133, the explanation of the pressed switch is displayed. The host controller 116 then returns to the step S130. When the explanation of the pressed switch is displayed, if the verification switch is pressed at the step 132, the host controller 116 deletes the explanation and returns to the step S130.

In the Help-mode screen 169, the explanation display section 170 may have a hierarchical structure, so that more detailed explanation can be displayed in the explanation display area 170, or a switch for enabling display of the explanation of a link with any other operation switch can be formed. The Help-mode switch 168 may be formed in all operation screens, so that the Help mode can be designated to display explanation of use.

Figure 31:
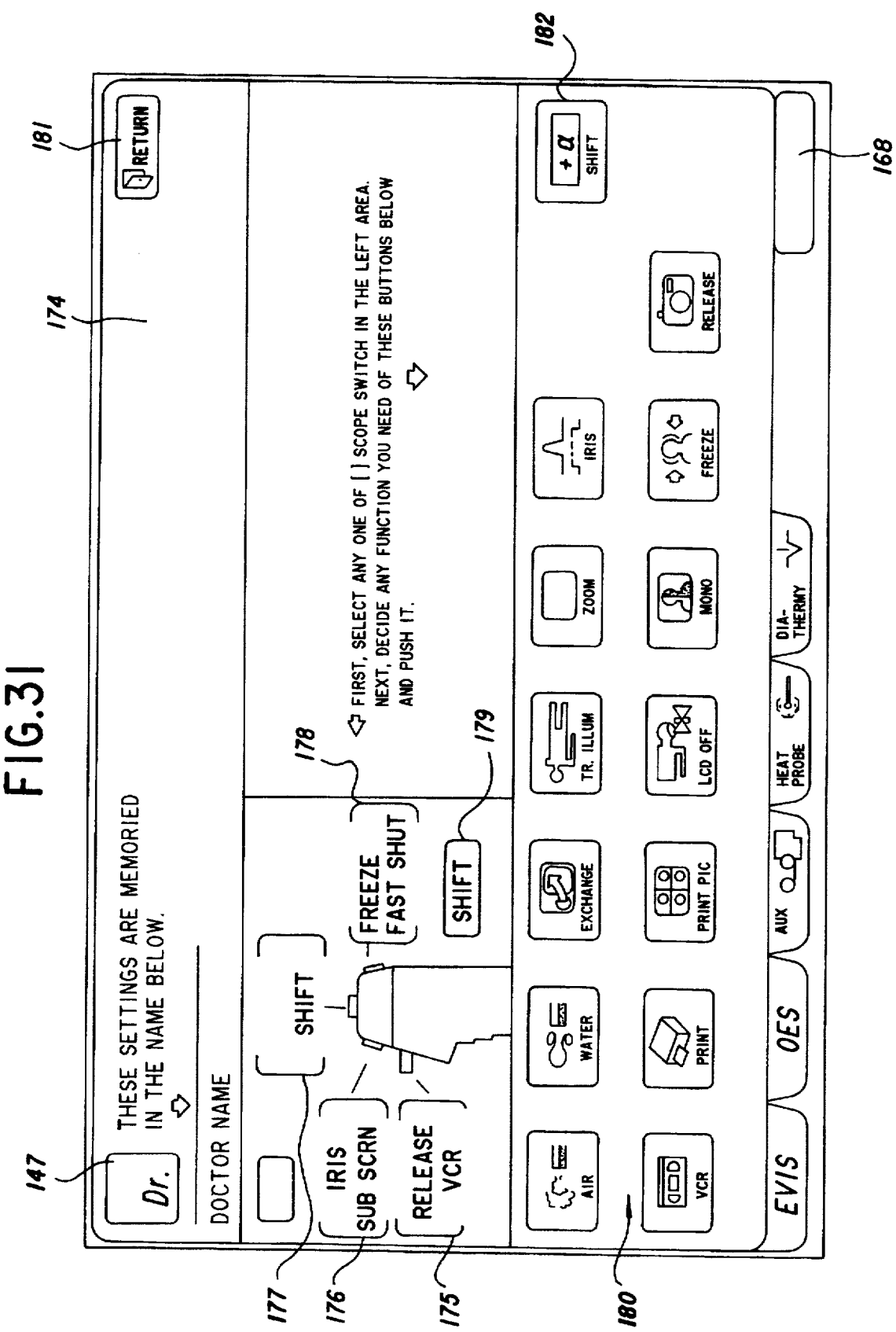
FIG. 31 is an explanatory diagram showing a scope switch setting screen for use in setting functions of operation switches of an endoscope.
Figure 32:
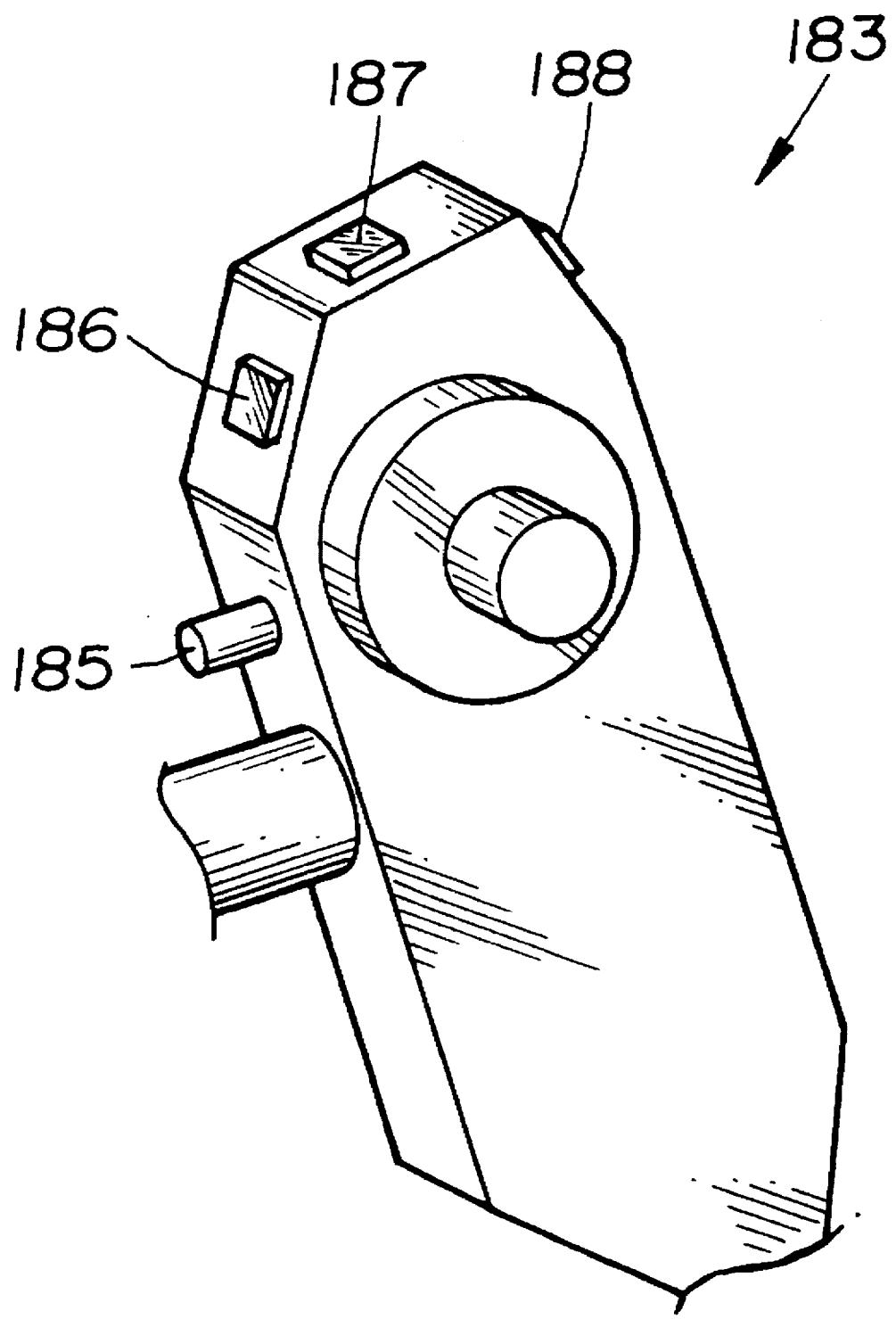
FIG. 32 is an oblique view of an operation unit of an endoscope.

Next, setting the functions of operation switches formed in an operational part of an endoscope will be described. In the main operation screen 131, the scope switch setting screen select switch 149 is pressed to select the scope switch setting screen 174 shown in FIG. 31. In the scope switch setting screen 174, the functions of operation switches on an endoscope can be specified. As shown in FIG. 32, an operational endoscope part 83 has four operation switches (A) 185, (B) 186, (C) 187, and (D) 188. A picture of the operational endoscope part is displayed in the scope switch setting screen 174. Switch select keys 175, 176, 177, and 178 are formed in association with the four operation switches. A SHIFT select key 179 is formed to allocate a Shift function to any switch in an extension mode which will be described later. Function select keys 180 are located in the lower part of the scope switch setting screen 174. A decision key 181 is formed at the upper right corner thereof.

In this embodiment, setting the functions of the operation switches of an endoscope is achieved in two modes; that is, a standard mode in which a total of four functions are set by allocating one function to each switch, and an extension mode in which a total of six functions are set by allocating a Shift function to a certain switch and then using the Shift switch and other three switches in combination.

When functions are set in the standard mode, if a function is allocated to the operation switch (A) 185 of an endoscope, the associated switch select key 175 is pressed first. The rim of the key then changes in color, indicating that the switch is selected. Next, a desired function is selected from the function select keys 180, and the associated one of the function select keys 180 is pressed to allocate the desired function to the operation switch (A) 185. Functions can be allocated to the other operation switches 186 to 188 according to the foregoing procedure.

When functions are set in the extension mode, the function of the SHIFT key 182 is allocated to any of the operation switches 185 to 188. Assuming that the Shift function is allocated to the operation switch (C) 187, functions different from those specified by pressing the operation switch (A) 185, (B) 186, and (D) 188 respectively can be specified by pressing the operation switch (A) 185, (B) 186, and (D) 188 with the operation switch (C) 187 held down. A total of six functions can thus be activated using the operation switches 185 to 188 on an endoscope.

To allocate the Shift function to the operation switch (C) 187, the switch select key 177 must be pressed first. The operation switch (C) 187 is then selected. Next, the SHIFT key 182 is pressed to specify the operation switch (C) 187 as a Shift switch. Assuming that a Release function is to be allocated to the operation switch (A) 185 and a Water function is to be allocated to a combination of the operation switches (C) 187 and (A) 185, the switch select key 175 is pressed to select the operation switch (A) 185. A RELEASE key is selected from among the function select keys 180, and then pressed to allocate a function exclusively to the operation switch (A) 185. Thereafter, the SHIFT select key 179 is pressed, and then a WATER key among the function select keys 180 is pressed to allocate a function to a combination of the operation switches (C) 187 and (A) 185. Two kinds of functions are thus allocated to the operation switch (A) 185. Functions can be allocated to other operation switches (B) 186 and (D) 188, according to the foregoing procedure.

After the functions are allocated to the operation switches of an endoscope, the decision key 181 is pressed to decide on the specified functions. The main operation screen 131 is then returned. The main operation screen 131 shows the specified functions of the operation switches together with the picture of an operational endoscope part. The scope switch setting table listing the functions specified for the operation switches is stored in a memory in, for example, the host controller 116.

Figure 54:
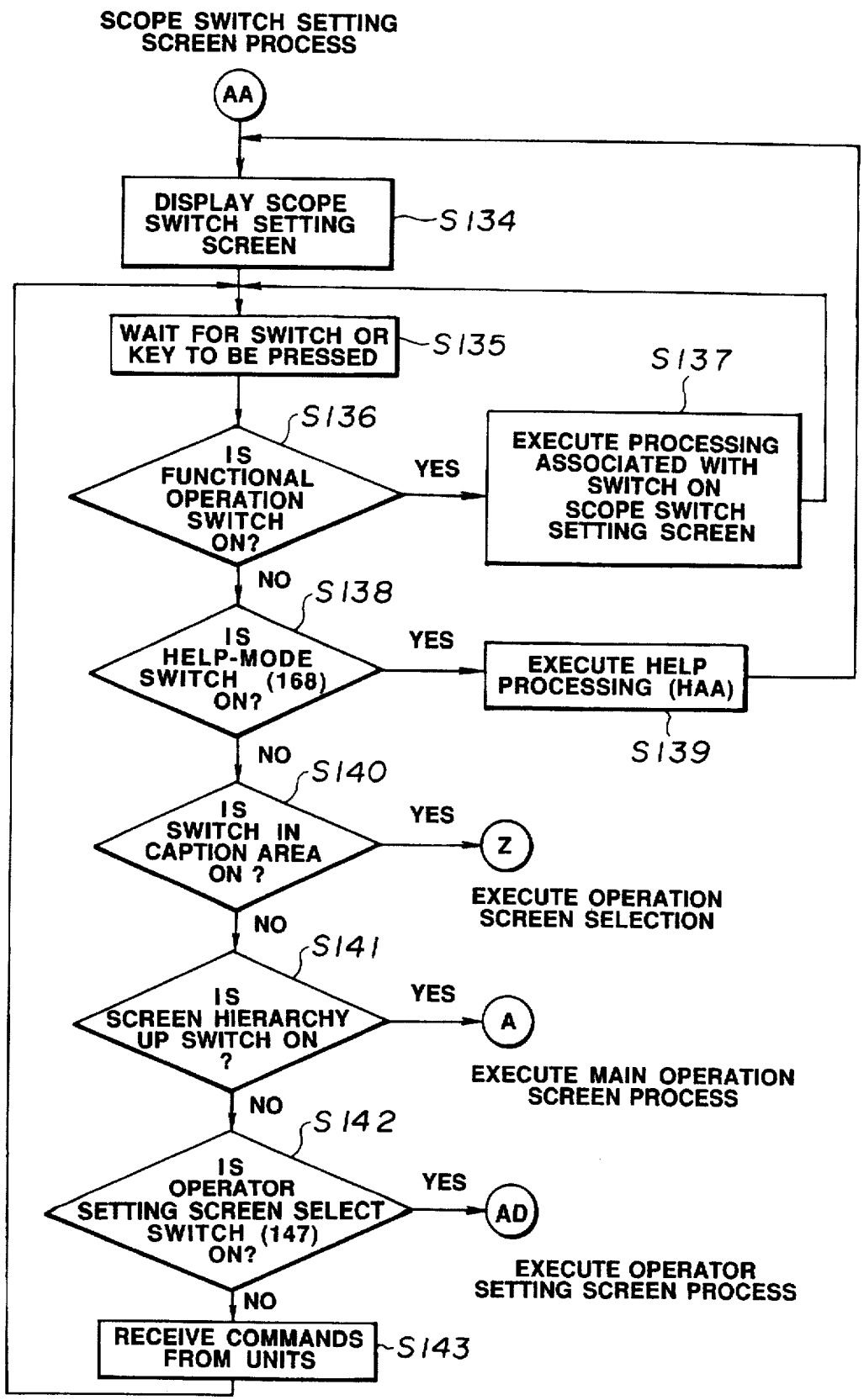
FIGS. 54 and 55 are flowcharts showing the operations in a scope switch setting screen process.

FIG. 54 shows the operations in the scope switch setting screen process (AA). The host controller 116 displays the scope switch setting screen at a step S134, and then waits at a step S135 until any operation switch or key in the scope switch setting screen 174 is pressed. If an operation switch is pressed, the host controller 116 advances to a step S137, executes the processing associated with the pressed switch, and then returns to the step S135. If it is found at the step S136 that a functional operation switch is not pressed, it is determined at a step S138 whether the pressed switch is the Help-mode switch 168. If the Help-mode switch 168 is pressed, the host controller 116 advances to a step S139, executes the aforesaid Help processing (HAA), and then returns to the step S134.

At a step S140, it is determined whether the pressed switch is any one in the caption area 137. If a switch in the caption area 137 is pressed, Operation Screen Selection (Z) shown in FIG. 38 is executed. At a step S141, it is determined whether the screen hierarchy up switch (herein, the decision key 181) is pressed. If the decision key is pressed, the host controller 116 returns to the main operation screen process (A) shown in FIG. 37. At a step S142, it is determined whether the operator setting screen select switch 147 is pressed. If the operator setting screen select switch 147 is pressed, the operator setting screen process (AD) is executed. If the determination made at any of the steps S136 to S142 is in the negative, the host controller 116 advances to a step S143, executes the command reception from equipment shown in FIG. 39, and then returns to the step S135.

Figure 55:
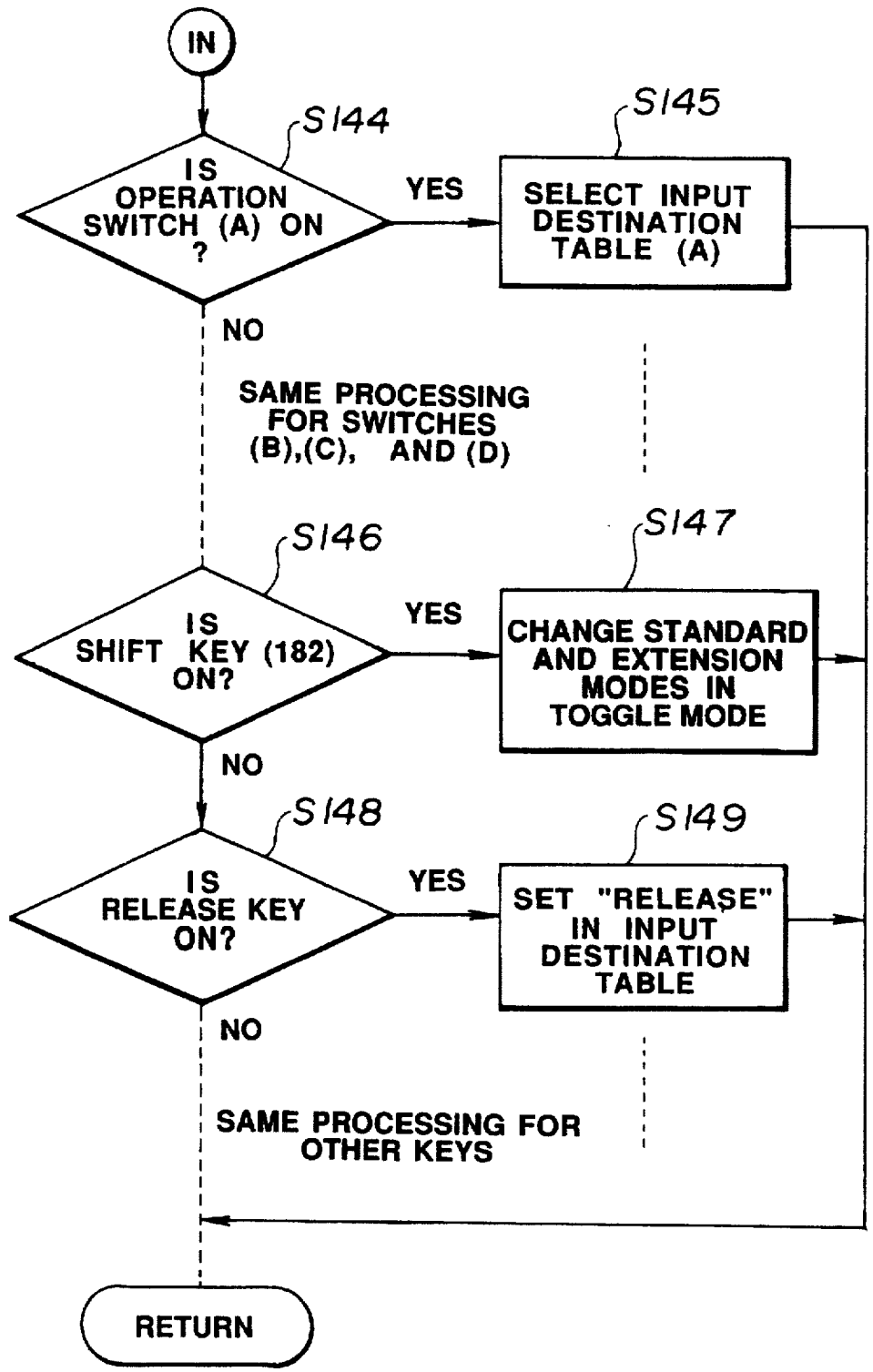

FIG. 55 shows the processing operation associated with a switch or key in the scope switch setting screen which is executed at the step S137. In the scope switch setting screen 174, assuming that the select key 175 for allocating a function to the operation switch (A) of an endoscope is pressed, the host controller 116 determines at a step S144 whether allocation to the operation switch (A) is selected. For allocation to the operation switch (A), A is specified as a table listing input destinations of set functions in the scope switch setting table. The same processing is performed for the operation switches (B), (C), and (D). At a step S146, it is determined whether the SHIFT key 182 is pressed. If the SHIFT key 182 is pressed, the host controller 116 advances to a step S147 and changes the standard and extension modes in toggle mode.

For example, when the RELEASE key is selected from the function select keys 180, it is determined at a step S148 whether the RELEASE key is pressed. At a step S149, "Release" is allocated as a function of the operation switch (A) in the input destination table. The same processing is performed when any other function select key is pressed.

Instruction information sent from the operation switches 185 to 188 on the operational endoscope part 183 is transmitted from the endoscope 111 to the video system center 5 in FIG. 18. The information is then sent as commands to the host controller 116 via the serial controller 117. The host controller 116 then transmits instructions concerning the allocated functions to the associated units. Units are thus controlled by means of the operation switches 185 to 188 of the operational endoscope part 83.

As described above, desired functions can be allocated to the operation switches 185 to 188 of the operational endoscope part 83, and peripheral equipment can be controlled using the operation switches of the endoscope. Allocation of functions can be modified effortlessly.

Next, operator-specific setting of peripheral equipment will be described.

Figure 33:
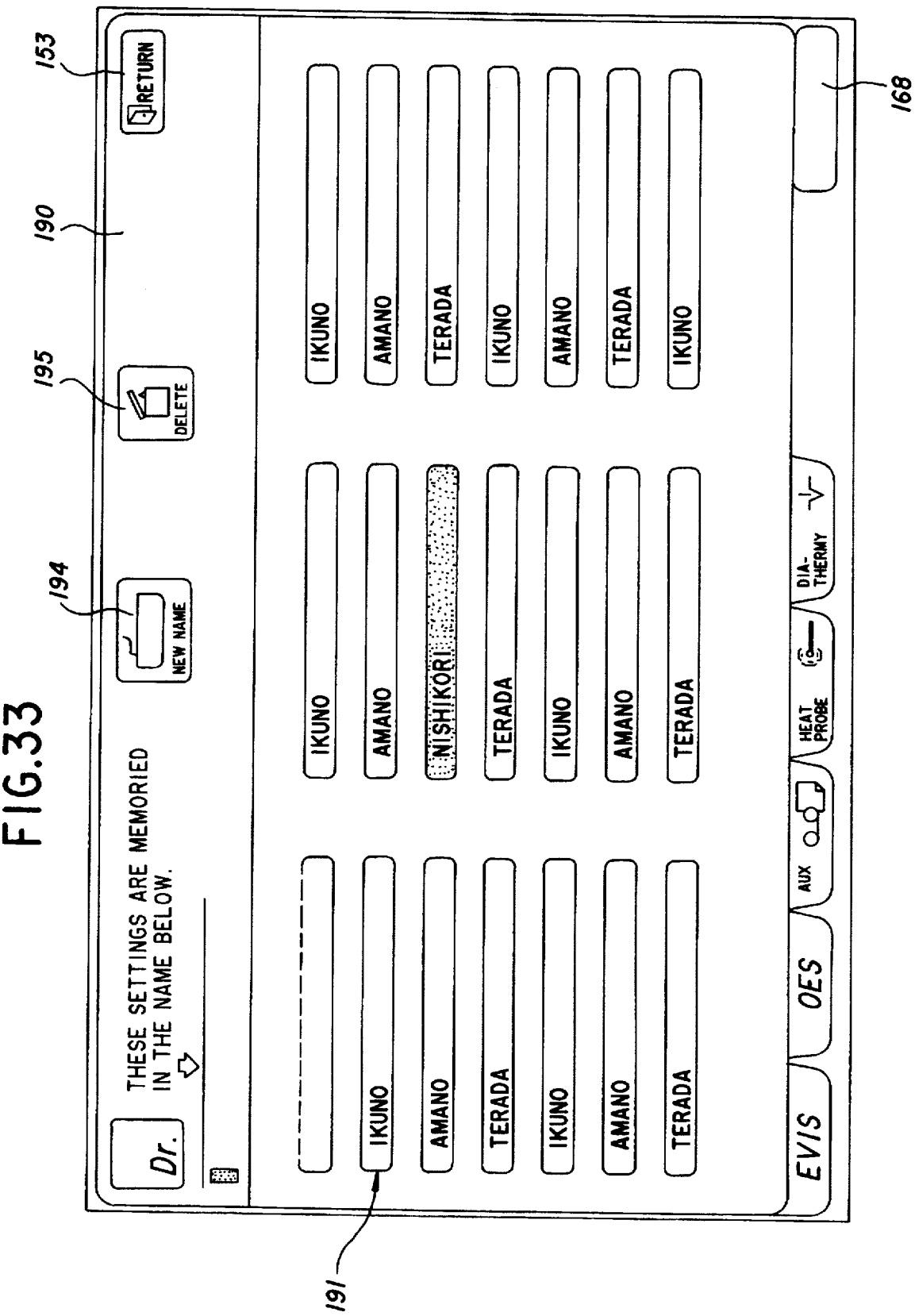
FIG. 33 is an explanatory diagram showing an operator setting screen for use in selecting operator-specific set values for peripheral equipment.

In this embodiment, the set values of each peripheral equipment, which are set to desired values by each operator, are stored in memory. When operators change, set values are read out. Peripheral equipment are thus set up immediately according to specified set values. When the set values for each peripheral equipment are to be modified, the operator setting screen select switch 147 in the main operation screen 131 or the like is pressed to select the operator setting screen 190 shown in FIG. 33. The operator setting screen select switch 147 is formed in all operation screens except the operation screens whose set values may be modified; that is, the date setting screen 154 and patient data input screens (1) 164 and (2) 165. The operator setting screen 190 can therefore be called immediately.

The operator setting screen 190 has an operator name select switch area 191 from which an operator name is selected. Operator-specific set values for peripheral equipment can be called by selecting an operator name from the operation name select switch area 191. After an operator name is selected, if the screen hierarchy up switch 153 is pressed, an original operation screen appears. In an operation screen, similarly to, for example, the electronic endoscope setting screen 132 shown in FIG. 20, a current operator name is displayed in an operator name display area 192. For entering a new operator name, a new input key 194 is pressed in the operator setting screen 190. An input screen identical to the patient data input screen (1) 164 is then displayed to enter data. For deleting an operator name, a DELETE key 195 is pressed.

Referring to FIG. 26, the aforesaid operator-specific setting will be described. After an operator name is selected, a quantity of light in the light source apparatus 6 and a tone in the video system center 5 are specified in, for example, the electronic endoscope setting screen 132. The set values are sent to the host controller 116. The host controller 116 then sends a command to the serial interface 126, whereby the set value of a quantity of light is fed to the light source apparatus 6 via the light source interface 127 and the set value of a tone is fed to the video system center 5 via the video processor interface 128. The light source apparatus and video system center are thus controlled. At the same time, the host controller 116 transmits the set values to a set value storage means 138, and stores the set values in association with the operator name. The set value storage means 138 stores the sent set values in the order of operators displayed in the operator name display area 192.

The set values thus stored operator by operator are called by the host controller 116 when an operator name is selected by selecting a corresponding switch from among the operator name select switch area 191 in the operator setting screen 190. The host controller 116 sets up peripheral equipment again, displays an operator name associated with the selected set values in the operator name display area 192, and then modifies the display of setting states in the operation screen.

Figure 56:
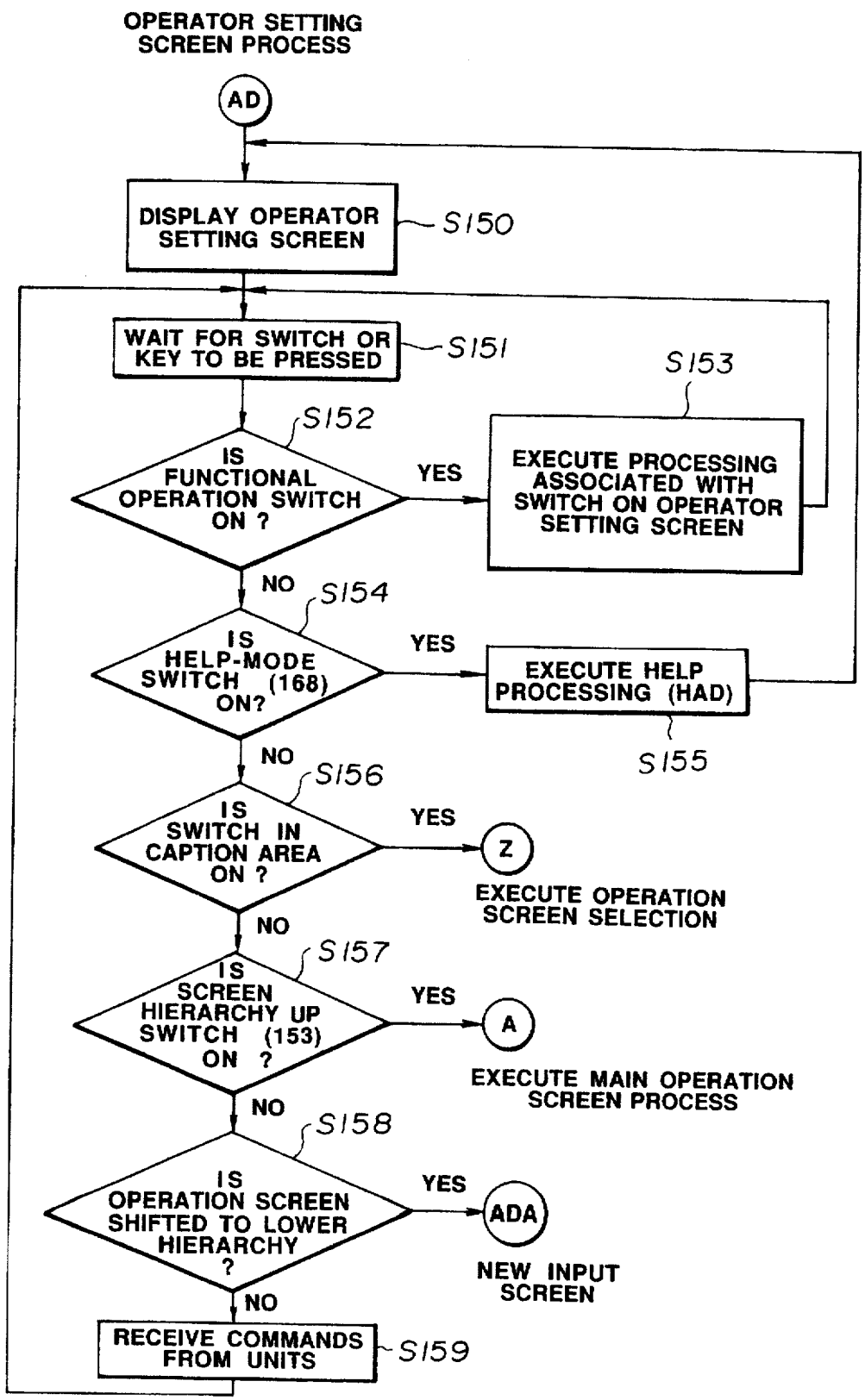
FIGS. 56 and 57 are flowcharts showing the operations in an operator setting screen process.

FIG. 56 shows the operations in the operator setting screen process (AD). The host controller 116 displays the operator setting screen at a step S150, and then waits at a step S151 until an operation switch or key in the operator setting screen 190 is pressed. When an operation switch is pressed, it is determined at a step S152 whether the pressed switch is a functional operation switch for designating a function in the operator setting screen 190. If a functional operation screen 190 is pressed, the host controller 116 advances to a step S153, executes the processing associated with the pressed switch, and then returns to the step S151. If it is found at a step S152 that a functional operation switch is not pressed, it is determined whether the pressed switch is the Help-mode switch 168. If the Help-mode switch 168 is pressed, the host controller 116 advances to a step S155, executes the aforesaid Help processing (HAD), and then returns to the step S150.

At a step S156, it is determined whether the pressed switch is any one in the caption area 137. If a switch in the caption area 137 is pressed, Operation Screen Selection (Z) shown in FIG. 38 is executed. If the screen hierarchy up switch 153 is pressed, the host controller 116 returns to the main operation screen process (A) shown in FIG. 37. However, the host controller 116 may not return to the main operation screen process (A) but may return to the process of the operation screen selected before the operator setting screen.

At a step S158, it is determined whether it is instructed to shift the operation screen to a lower hierarchy; that is, whether the new input key 194 is pressed. If the new input key 194 is pressed, a new input screen process (ADA) is executed. The operations in the new input screen process (ADA) are identical to those in the patient data input screen process (AC) shown in FIGS. 51 and 52. If the determination made at any of the steps S152 to S158 is in the negative, the host controller 116 advances to a step S159, executes the command reception from equipment shown in FIG. 39, and then returns to the step S151.

In the past, the set values for each peripheral equipment must have been re-entered every time operators change. For example, when operators take turns to conduct diagnosis or treatment because of quite a few cases a day, an operator may have to modify set values as he/she likes, or may use set values specified by any other operator while being unaware of the fact and then execute an operation different from the intended one. According to this embodiment, an operator need not verify or re-set set values every before examination. Once an operator stores set values in memory, what the operator have to do is only to select his/her own name from the operator setting screen 190. Peripheral equipment can thus be set up effortlessly.

Figure 34:
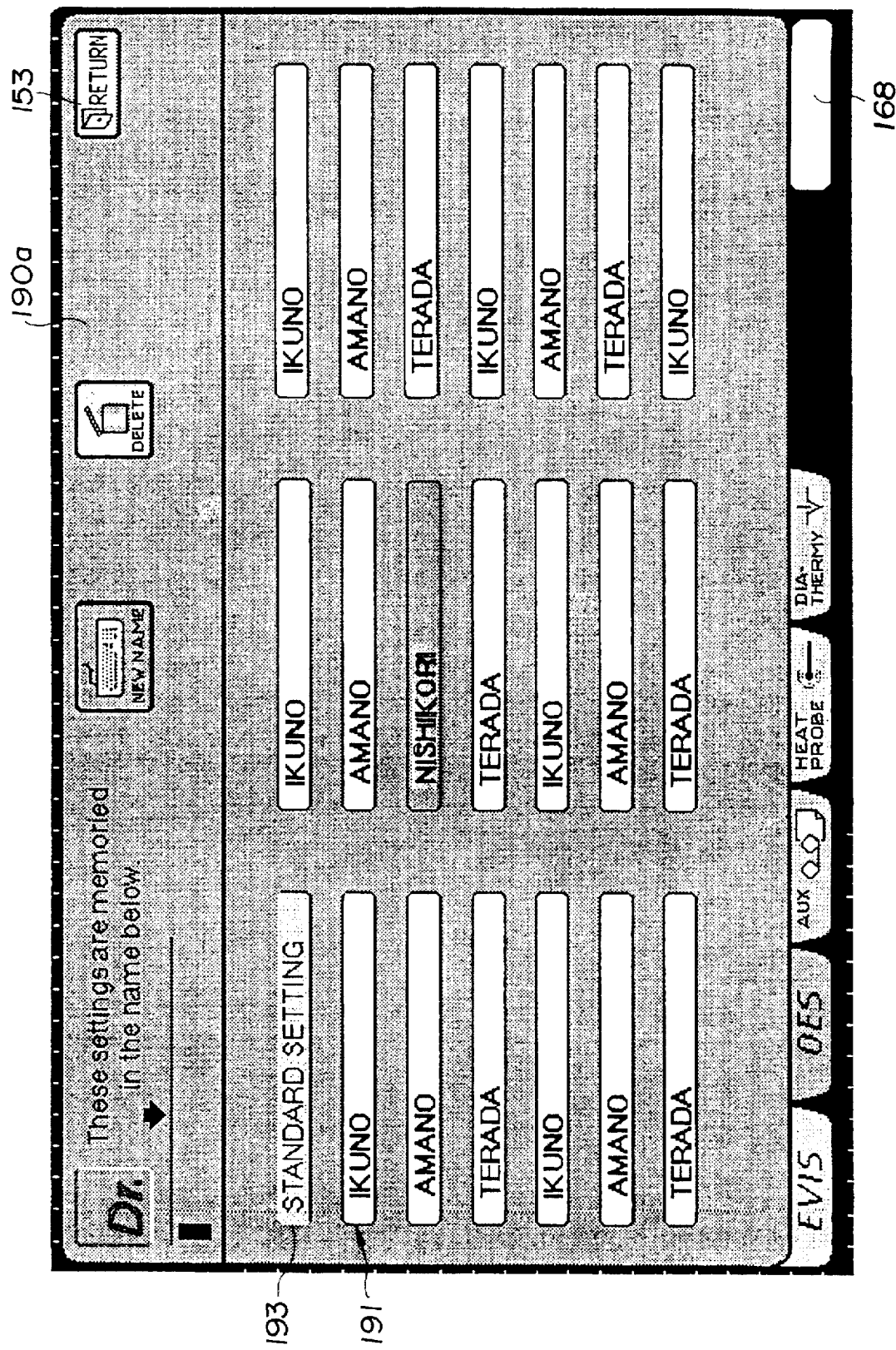
FIG. 34 is an explanatory diagram showing a variant of the operator setting screen.

As shown in FIG. 34, a standard setting select switch 193 for selecting standard set values may be formed in a operator setting screen 190a. Set values used on a standard basis in the system are stored in the set value storage means 138. When the standard setting select switch 193 is selected, the standard set values are called from the set value storage means 138. Peripheral equipment are then set up according to the standard set values. Meanwhile, STANDARD SETTING indicating a standard setting state appears in the operator name display area 192 as the one in the main operation screen 131 shown in FIG. 19. The standard setting state is therefore easily identified.

FIG. 57 shows the processing operation of a switch or key in the operator setting screen which is performed at the step S153 within the operator setting screen process. When the standard setting select switch 193 is formed in the operator setting screen, the host controller 116 determines at a step S160 whether the standard setting select switch 193 is pressed. At a step S161, the display of the switch is changed to an on state. The standard set values (fixed values) for peripheral equipment are read out at a step S162. Set commands are then transmitted to the peripheral equipment at a step S163. When a select switch for designating a certain operator is selected from among the operator name select switches 191, it is determined at a step S164 whether the operator select switch is pressed. At a step S165, the display of the switch is changed to an on state. At a step S166, the associated set values specified by the operator are read from the table in the set value storage means 138. At a step S167, set commands corresponding to the read set values are transmitted to the equipment. The same processing is performed for other operator select switches.

Figure 35:
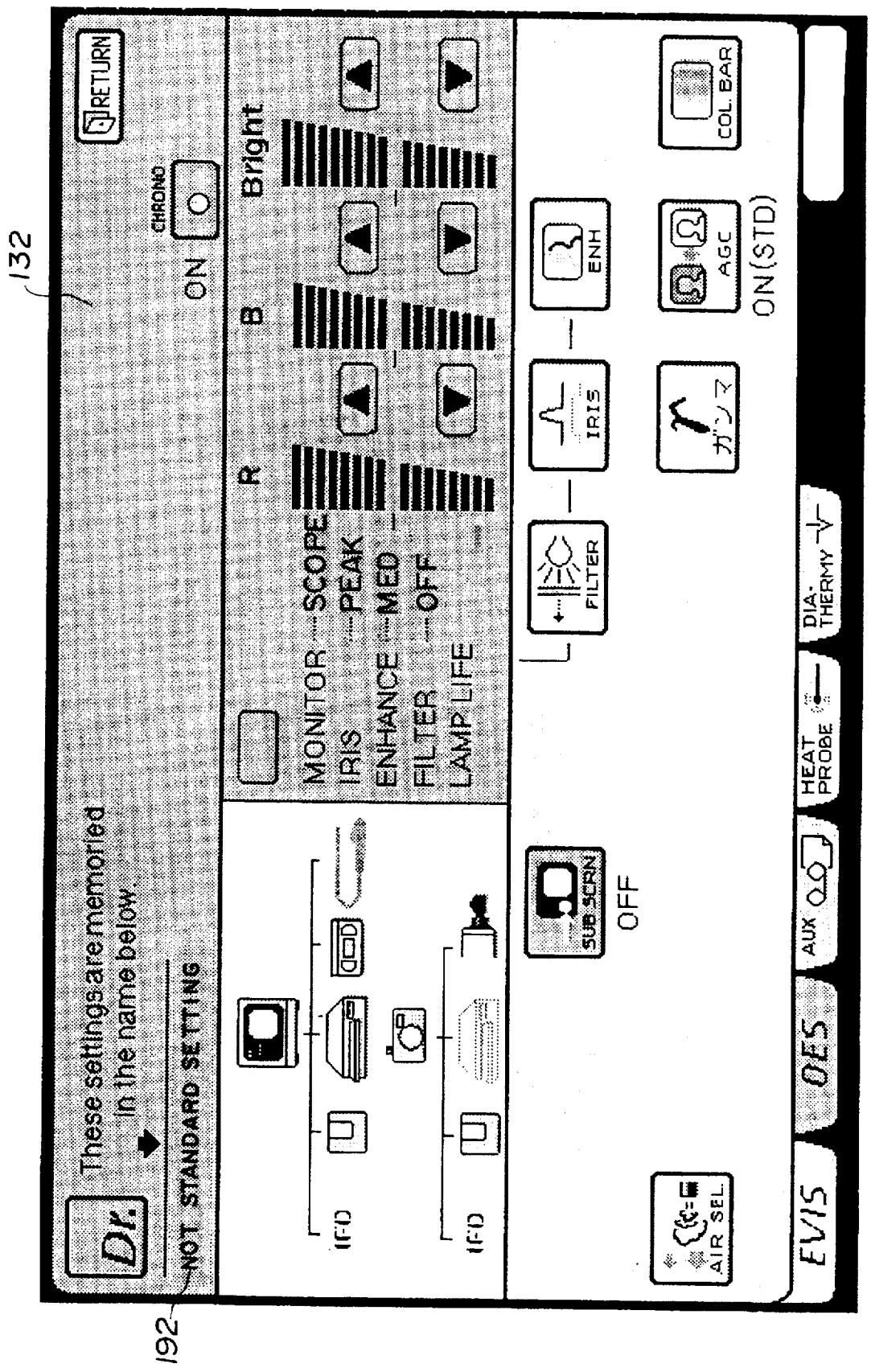
FIG. 35 is an explanatory diagram showing an operation screen appearing when the standard set values of the system have been modified.

When set values are modified in the standard setting state, as shown in FIG. 35, NOT STANDARD SETTING appears in the operator name display area 192 to indicate that the standard set values have been modified. If the standard set values should be modified intentionally or accidentally, an operator can be informed of or warned about the fact.

Since the standard set values are specified, even an operator unfamiliar with the system can use the system easily without any trouble merely by selecting the standard set values. On some occasions, for example, at a meeting of an association, the same parameters must be shared for use among multiple systems or operators. This can be achieved effortlessly by adopting the standard set values.

As described above, according to this embodiment, a desired operation screen can be displayed immediately irrelevant of the hierarchy of a current operation screen merely by selecting an associated one of the operation screen select switches 141 to 145 in the caption area 137. An unnecessary operation such as changing operation screens sequentially can therefore be eliminated, thus improving the operability of an endoscope system for diagnosis or treatment. Even an operator unfamiliar with an endoscopic procedure can use an endoscope system easily to conduct diagnosis or treatment.

The operation screen displayed in the control panel includes multiple operation screens associated with functions or units. Screens associated with functions of peripheral equipment to be controlled can be displayed selectively. Using the control panel, numerous functions can be used with excellent operability. Erroneous use can therefore be prevented.

The operation screen select switches 141 to 145 are formed in the caption area 137 and shaped differently from other operation switches. This improves visibility, simplifies identification, and prevents erroneous use.

Furthermore, the setting state display area 160 for displaying various set values for units is based on both analog indication and digital indication. The analog indication permits intuitive recognition of a value with excellent visibility. The digital indication of a set value, which is interlocked with the analog indication, permits easy recognition of an exact numerical value with high precision. Even when precision is required, various set values can be specified for units reliability. Safety is therefore ensured in endoscopic examination.

Multiple arbitrary functions can be allocated to operation switches on an operational endoscope part, and displayed in association with the switches on operation screens. The allocated functions can therefore be verified easily. Consequently, a desired function can be used correctly by manipulating the operational endoscope part.

As for set values for peripheral equipment, each operator can set and store desired values. By designating an operator name, set values can be changed effortlessly. This obviates the need of verifying or re-setting set values at every examination. An operator can use the system with the set values specified by himself/herself. Improved operability ensues.

Standard set values are stored in memory in association with peripheral equipment, which enables easy accomplishment of standard setting. Even an operator unfamiliar with the use of an endoscope system can operate the endoscope system with ease.

A variant of the aforesaid configuration of an endoscope system in the second embodiment will be described below.

FIGS. 58 to 61 show the first variant.

Figure 58:
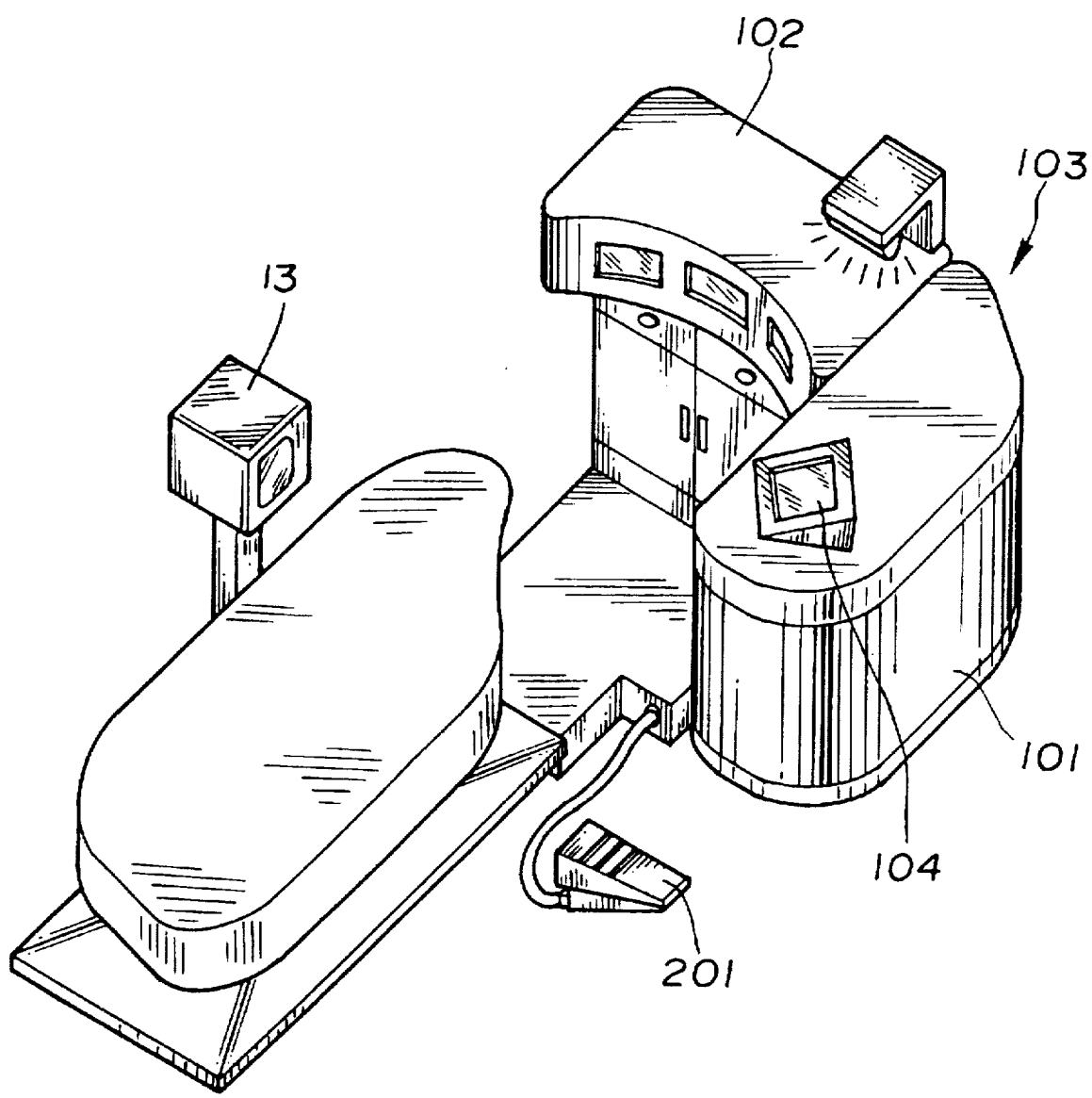
FIGS. 58 to 61 relate to the first variant of the second embodiment.

The first variant includes variants of operation screens to be displayed on the control panel 104 of an endoscope system. As shown in FIG. 58, the endoscope system consists mainly of, similarly to that in the second embodiment, a system body 103 made up of a doctor workstation 101 and a nurse workstation 102, a control panel 104 serving as a main operational instruction means for operating the system on a centralized basis, and a monitor 13 for displaying endoscopic images. In this variant, a foot switch 201 for designating or executing a specified function can be connected to the system body 103.

Similarly to the second embodiment, under the control of the host controller 116, operation screens are displayed on the control panel 104. Using the operation screens on the control panel 104, peripheral equipment of the endoscope system can be operated or controlled on a centralized basis.

Figure 59:
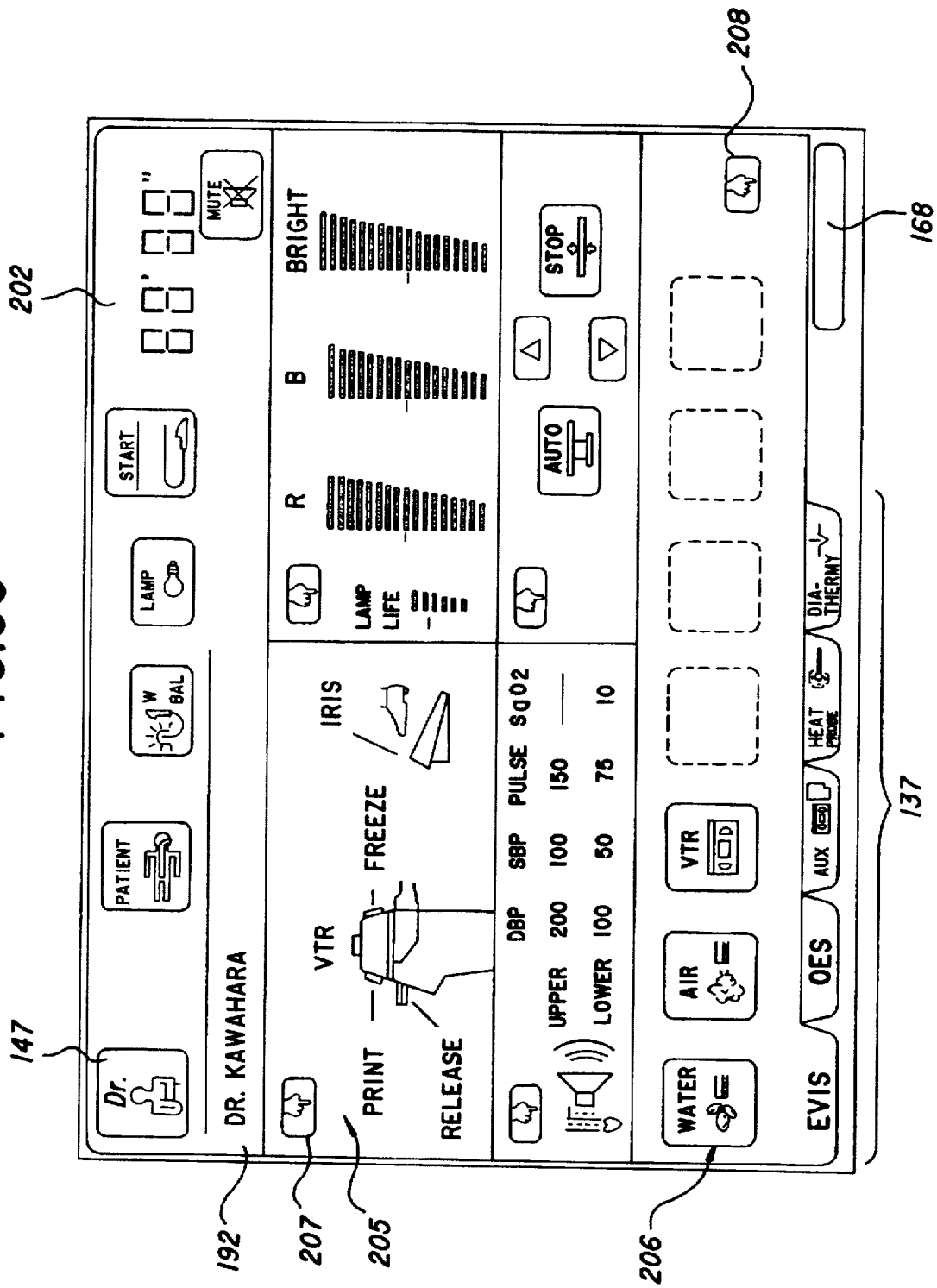
Figure 60:
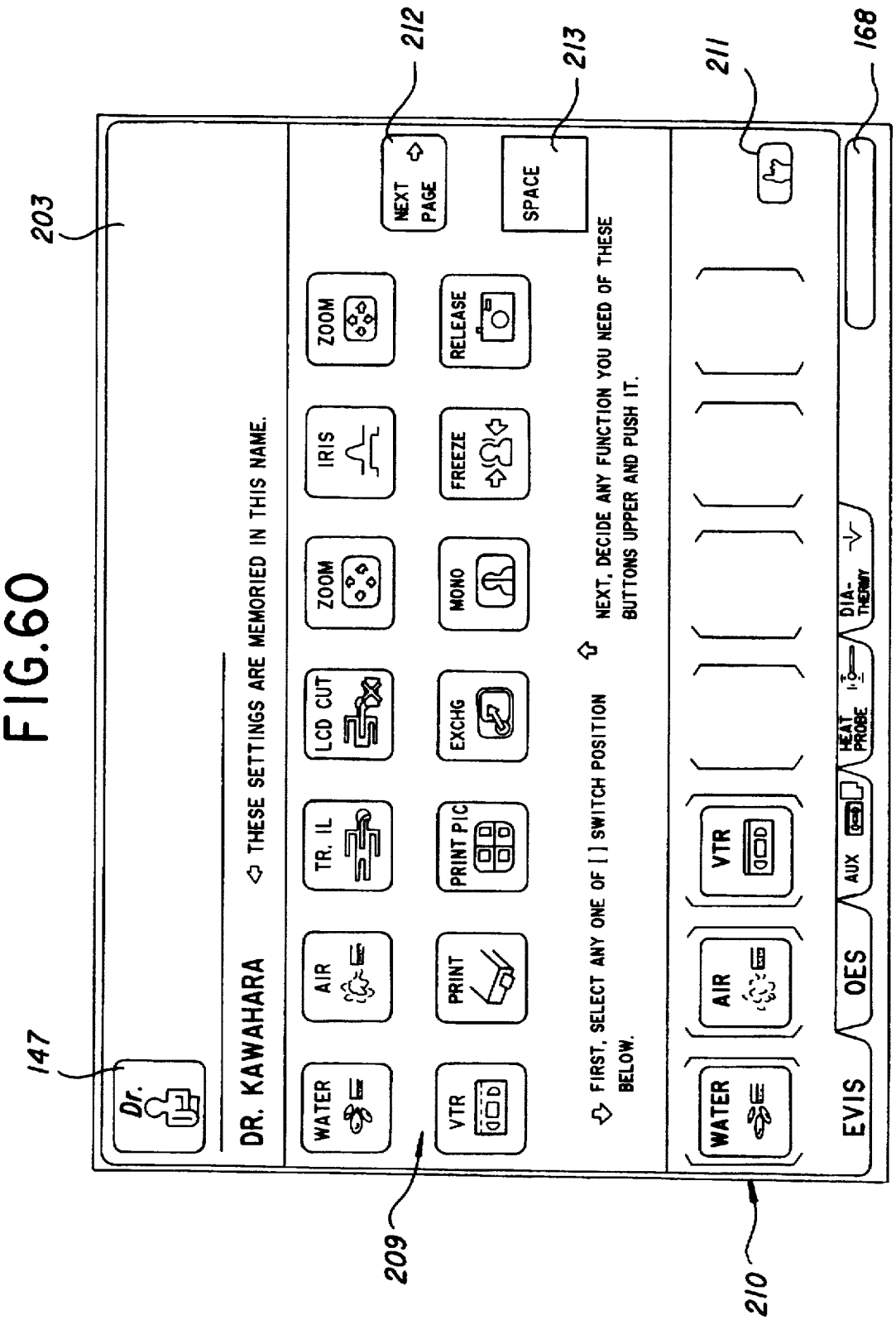
Figure 61:
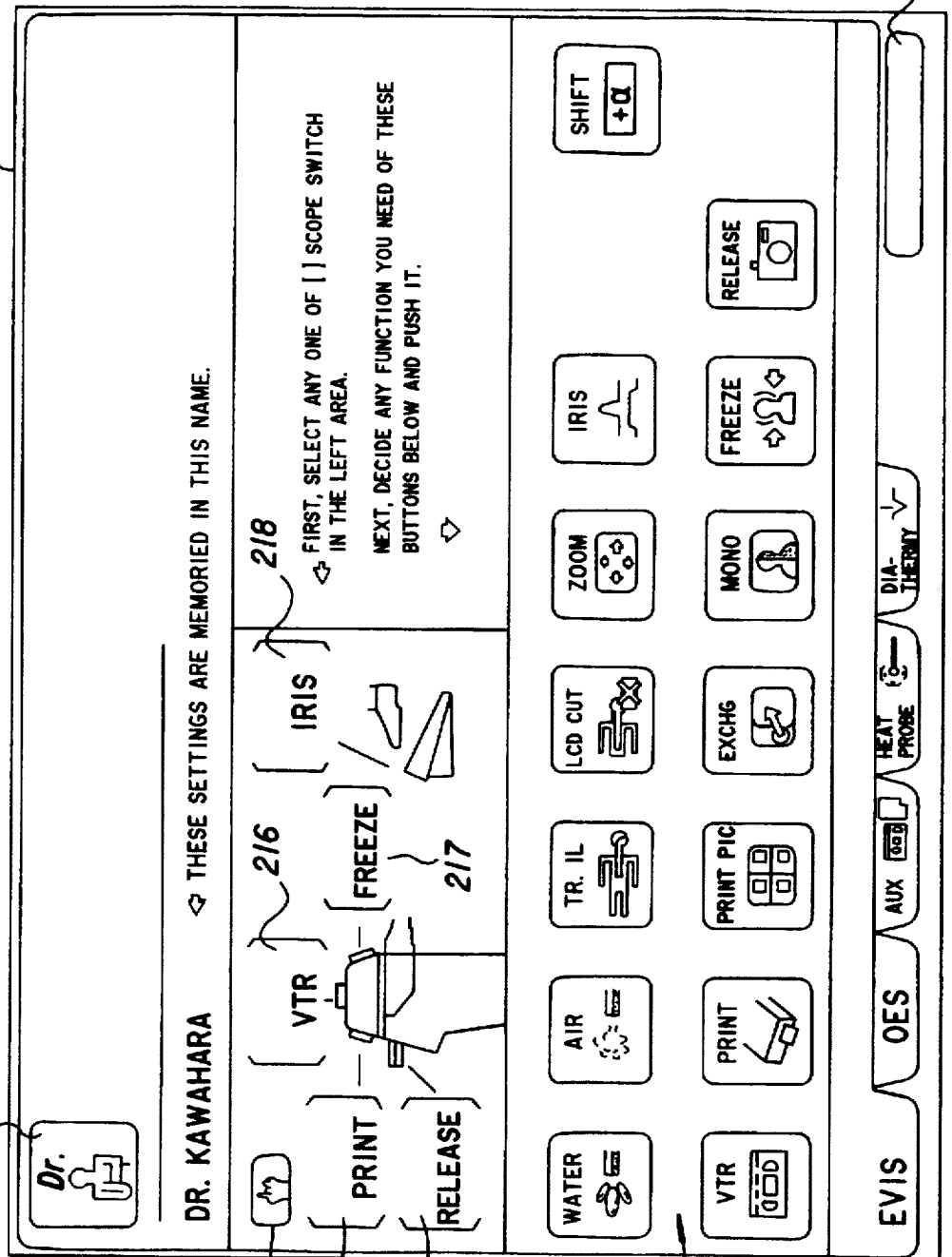

In this variant, the operation screen to be displayed on the control panel 104 includes a main operation screen 202 shown in FIG. 59, an operation switch layout setting screen 203 shown in FIG. 60 for setting the locations of switches in an operation screen, and a scope/foot switch setting screen 204 shown in FIG. 61 for setting the functions of scope and foot switches. Other operation screens related to peripheral equipment are identical to those in the second embodiment, of which description will therefore be omitted.

When the power supply of the system is turned on, the main operation screen 202 appears on the control panel 104. The use of an electronic endoscope or the like is then enabled.

The main operation screen 202 includes at least a function setting display area 205 for displaying the functions allocated to the operation switches of an endoscope and the foot switch, which is located in the left center of the main operation screen 202, an operation switch display area 206 for displaying operation switches for arbitrary functions related to an endoscope or peripheral equipment, which is located in the lower part thereof, and an operator name display area 192 and an operator setting screen select switch 147 which are located in the upper part thereof. Furthermore, a scope/foot switch setting screen select switch 207 for selecting the scope/foot switch setting screen 204 and an operation switch layout setting screen select switch 208 for selecting an operation switch layout setting screen 203 are formed in the main operation screen 202. By pressing the select switches, the associated setting screens are selected.

Allocating a function to an operation switch in the operation switch display area 206 in the main operation screen 202 will be described below.

In the main operation screen 202, the operation switch layout setting screen 203 shown in FIG. 60 is selected by pressing the operation switch layout setting screen select switch 208. The operation switch layout setting screen 203 has function select keys 209 in the center thereof, and location setting keys 210 below the function select keys 209. A screen hierarchy up switch 211 for use in returning to the main operation screen 202 is formed at the lower right corner of the operation switch layout setting screen 203.

In this variant, the operation switch layout setting screen 203 is used to select any function switch. The function associated with the selected function switch can be allocated to a desired location in the operation switch display area 206 in the main operation screen 202. Operation switches to be located in the operation switch display area 206 vary depending on an operator.

To set the location of an operation switch, similarly to that in the second embodiment, first, the operator setting screen select switch 147 is pressed to specify an operator in the operator setting screen 190. An operator name who wants to set the locations of operation switches then appears in the operator name display area 192. The operation switch layout setting screen select switch 208 is pressed to select the operation switch layout setting screen 203. An operator can also be specified in the operation switch layout setting screen 203.

A key at a desired location is selected from among the location setting keys 210, and then pressed. The pressed key is then colored more conspicuously than other keys. The location of the selected key can therefore be easily identified. The operator then selects an operation switch, which is associated with a function which the operator wants to display in the operation switch display area 206 in the main operation screen 202 because he/she uses the function frequently, from among the function select keys 209. The operator then presses the selected key, whereby the selected operation switch associated with the intended function is set and displayed in a specified location in the operation switch display area 206.

The aforesaid procedure is repeated by the number of desired functions. After switch selection terminates, when the screen hierarchy up switch 211 is pressed, the main operation screen 202 is returned. Switches numbering seven at maximum or zero at minimum, which an operator has selected as he/she likes, are displayed in the operation switch display area 206 in the main operation screen 202. The example shown in FIG. 59 is the setting made by Dr. Kawahara whose name is indicated in the operator name display area 192, wherein Water, AIR, and VTR operation switches are allocated in that order from the left end of the operation switch display area 206. When the operation switches are pressed, instructions concerning the functions of the switches are sent to intended units. The functions are thus activated.

When a next page switch for function selection 212 is pressed in the operation switch layout setting screen 203, operation switches other than those appearing in the function select keys 209 appear. Any function can be selected by pressing any of the operation switches. Numerous functions can therefore be set in the operation switch display area 206 in the main operation screen 202. The number of pages for the function select keys 209 is not limited to two, but may be set to an value according to the number of functions operable using operation switches.

After a function is allocated to any location in the operation switch display area 206, if it is intended that the operation switch of the function will not be displayed but be a blank, a SPACE switch 213 formed in the operation switch layout setting screen 203 is used. That is to say, the operation switch at a location at which the SPACE switch is pressed is not displayed.

Next is allocating functions to the operation switches 185 to 188 formed on an operational endoscope part shown in FIG. 32 and to the remote switches including the foot switch 201 shown in FIG. 58.

When the scope/foot switch setting screen select switch 207 is pressed in the main operation screen 202, the scope/foot switch setting screen 204 shown in FIG. 61 appears. The pictures of an operational endoscope part and a foot switch are displayed in the scope/foot switch setting screen 204. The scope/foot switch setting screen 204 includes scope switch select keys 214 to 217 and a foot switch select key 218. Function select keys 219 are arranged in the lower part of the scope/foot switch setting screen 204.

In this variant, desired functions can be allocated to the operation switches 185 to 188 on an endoscope in the similar manner as that in the second embodiment. Furthermore, any function can be selected and allocated to the foot switch 201. A function to be allocated to the foot switch can be made specific to each operator.

When functions are to be allocated to the operation switches 185 to 188 on an endoscope and the foot switch 201, the operator setting screen select switch 147 is pressed first. An operator name is specified in the operator setting screen 190 in the same manner as that in the second embodiment. The name of an operator who performs function allocation then appears in the operator name display area 192. The scope/foot switch setting screen select switch 207 is then pressed, and the scope/foot switch setting screen 204 appears. An operator name can be specified in the scope/foot switch setting screen 204.

A scope switch select key corresponding to an intended one of the operation switches 185 to 188 on an endoscope is then pressed. The pressed key is then colored more conspicuously than other keys, whereby the selected operation switch can be identified easily. The operator selects and presses a switch having a function, which the operator wants to allocate to the designated operation switch of the endoscope because he/she uses it very frequently, from among the function select keys 219. The desired function can thus be allocated to the designated operation switch of the endoscope by selecting the associated operation switch. Functions can be allocated to other operation switches of the endoscope and the foot switch 201 according to the same procedure.

After function allocation to all of the operation switches 185 to 188 of an endoscope and to the foot switch 201 has terminated, when the screen hierarchy up switch 220 is pressed, the main operation screen 202 is returned. The functions of the operation switches 185 to 188 on an endoscope and of the foot switch 201 are displayed in a function setting display area 205 in the main operation screen 202. The functions displayed in the function setting display area 205 are associated with the operation switches 185 to 188 on an endoscope and the foot switch 201 respectively. Using these switches, the functions an operator has allocated according to his/her likes are executed.

The example shown in FIG. 59 represents the setting of Dr. Kawahara whose name is displayed in the operator name display area 192, wherein Release is allocated to the operation switch (A) 185 on an endoscope, Print is allocated to the operation switch (B) 186 thereon, VTR is allocated to the operation switch (C) 187 thereon, Freeze is allocated to the operation switch (D) 188 thereon, and Iris is allocated to the foot switch 201. When the remote switches are pressed, instructions concerning the functions allocated to the switches are sent to intended units. The units are thus activated.

As described above, according to this variant, only the switches an operator uses frequently can be displayed as operator-specific functions in the operation switch display area 206. This improves operability, and avoids an incident that a redundant switch that is unused normally is pressed by mistake, and an endoscope system is therefore placed in a state an operator does not intend. When an endoscope system is provided with diverse functions on the assumption of many users, a certain operator may be annoyed by a large number of switches or has to call operation screens of lower hierarchies from time to time. In this variant, however, since a minimum number of operation switches required by a certain operator can be displayed in the main operation screen, the foregoing problems will not occur but only the operation switches used most frequently can be used smoothly.

An operator can not only set the operation functions of an endoscope system in an operation screen of the control panel but also allocate any functions to the operation switches of an endoscope and the foot switch which are remote switches. Using these remote switches, an operator can designate the allocated functions. The allocated functions can thus be used at a place other than the control panel, which permits free and easy operation even during endoscopic examination. The system operability thus improves.

Figure 62:
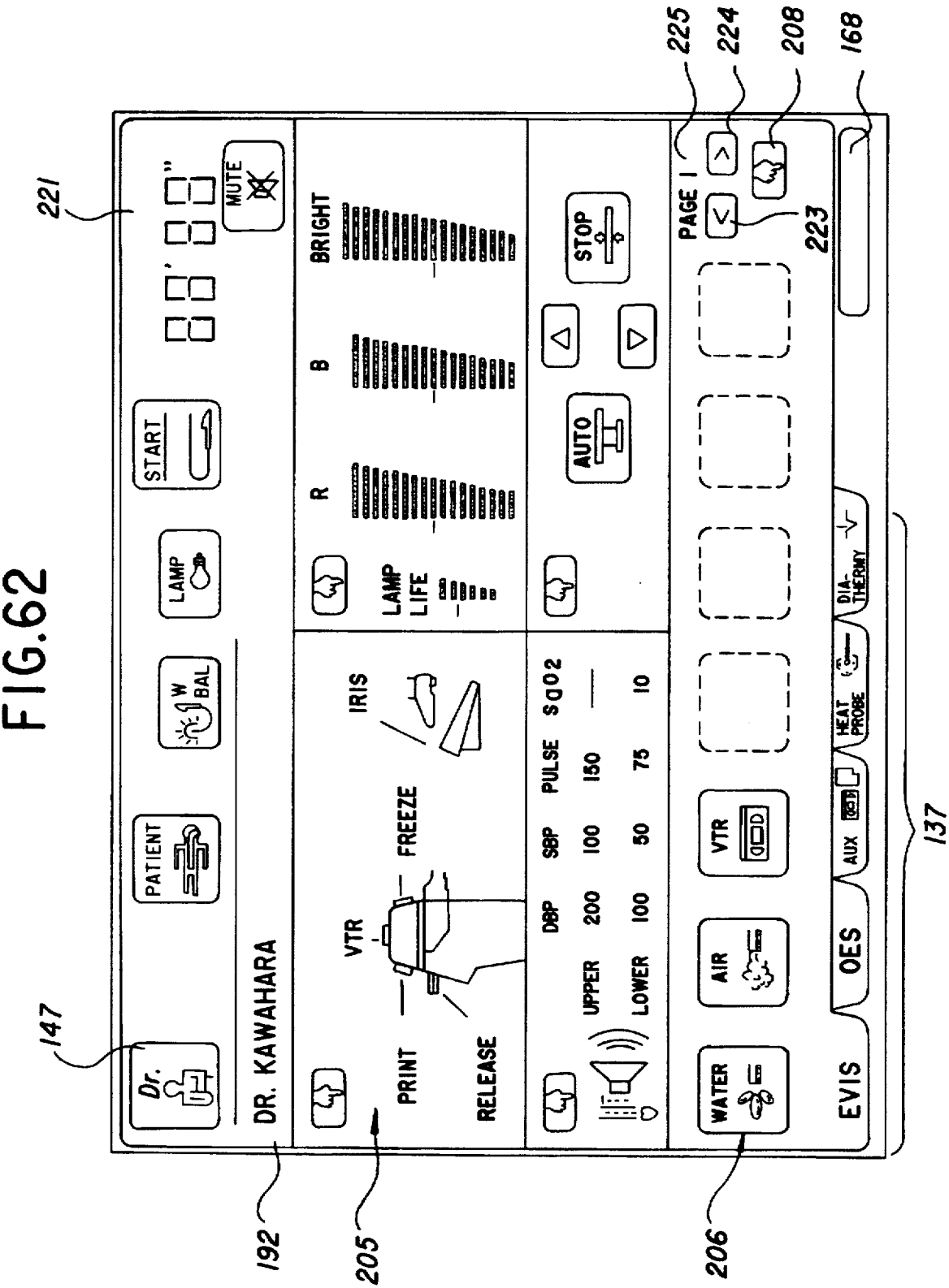
FIGS. 62 and 63 relate to the second variant of the second embodiment.
Figure 63:
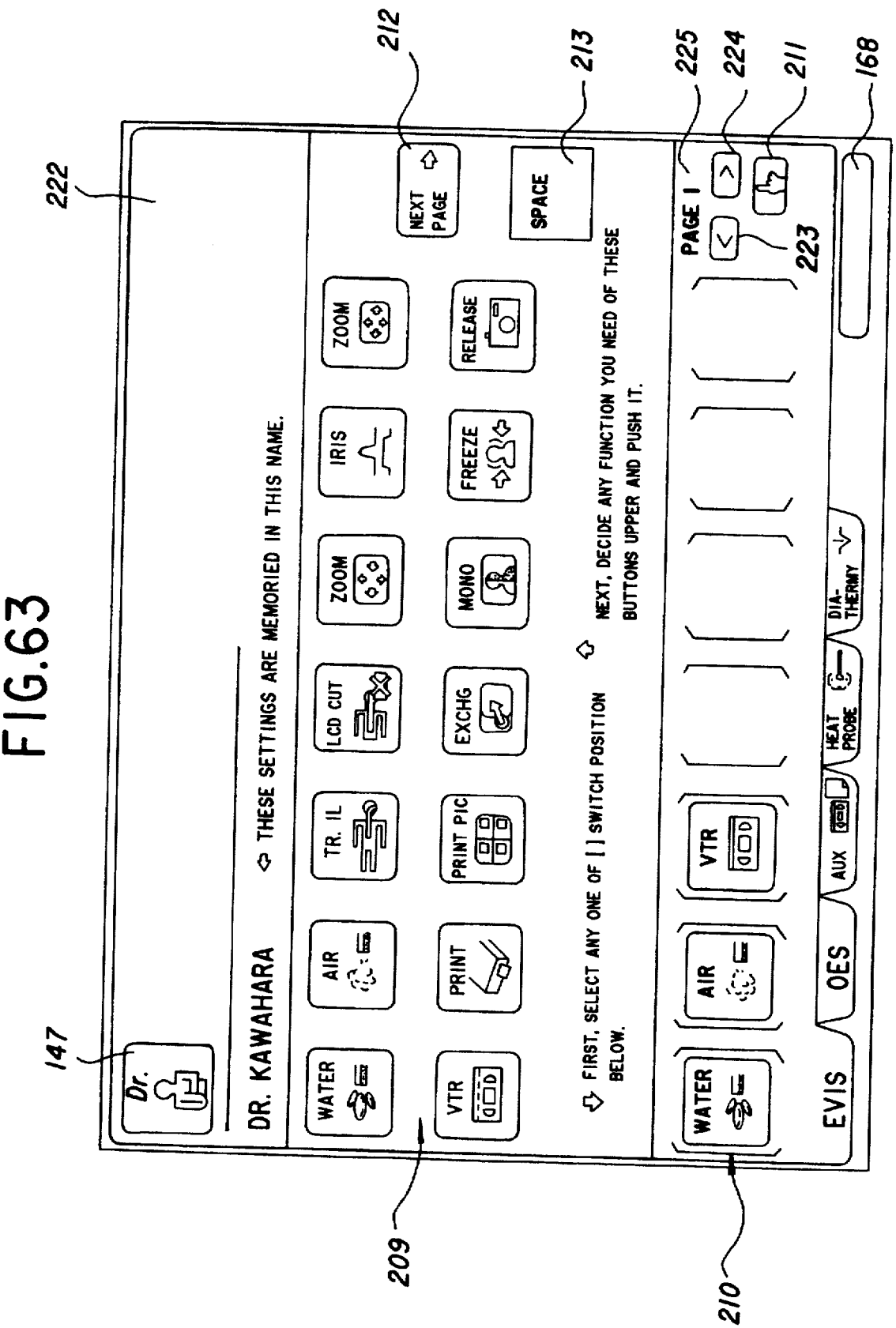

FIGS. 62 and 63 show the second variant.

The second variant includes variants of the main operation screen and operation switch layout setting screen in the first variant.

A main operation screen 221 shown in FIG. 62 or a operation switch layout setting screen 222 shown in FIG. 63 has the same screen format as that in the first variant except the addition of a previous page switch 223 for operation switches, a next page switch 224 for operation switches, and a page indicator 225 for operation switches, which are located at the lower right corner thereof.

In this variant, the number of operation switches to be displayed in the operation switch display area 206, which is seven at most in the first variant, is expanded. For example, seven operation switches are grouped as one page, and multiple pages are included in the operation switch display area 206. The procedure of setting the locations of operation switches is the same as that in the first variant.

For changing pages of operation switches in the operation switch display area 206, the previous page switch 223 for operation switches is pressed. The operation switches are then replaced with those in the previous page. When the next page switch 224 for operation switches is pressed, the operation switches are replaced with those in the next page. A current page number is indicated in the page indicator 225 for operation switches, which helps identify the hierarchy of the operation switch display area 206.

As described above, according to this variant, the following advantage is made available in addition to the advantages of the first variant: an operator can create a hierarchical structure made up of operation switches according to his/her own use frequency and paginate the hierarchies. A larger number of operation switches can be arranged easily with good operability.

Furthermore, no particular illustration is provided though, if the number of switches per page to be displayed in the operation switch display area 206 is smaller than a maximum number of switches to be displayed, the area or shape of each switch can be widened or altered depending on the number of switched to be displayed. This further improves operability.

The aforesaid power supply control for the heat prove unit 23 or electric cautery unit 28 will be detailed with reference to FIGS. 64 to 66.

When the power supplies of various peripheral equipment are controlled by instructing a host controller at a control panel, after a power supply of an equipment is turned on in an operation screen for controlling the equipment, if the operation screen is changed to another one, control is usually extended to hold the power supply on. In this kind of power supply control, when the power supply of a certain equipment should be turned off in case of emergency, it becomes necessary to call the operation screen related to the equipment. For example, after the power supply of, for example, an electric cautery is turned on, if operation screens are changed, an operator cannot verify either output values or a state of the power supply. Nevertheless, the operator may step on an output foot switch by accident. For solving these problems, as long as an equipment providing output such as an electric cautery is concerned, after the operation screen related to the equipment is escaped, the power supply of the equipment may be turned off. However, when the equipment is reused, the operation screen related to the equipment must be called to turn on the power supply. The procedure is rather a nuisance.

In this variant, as for the heat probe unit 23 or electric cautery unit 28, the state of the power switch set in the associated operation screen is stored in memory. When the operation screen for the unit is displayed again, the on or off state of the power supply of the unit is controlled according to the stored state of the power switch.

Figure 64:
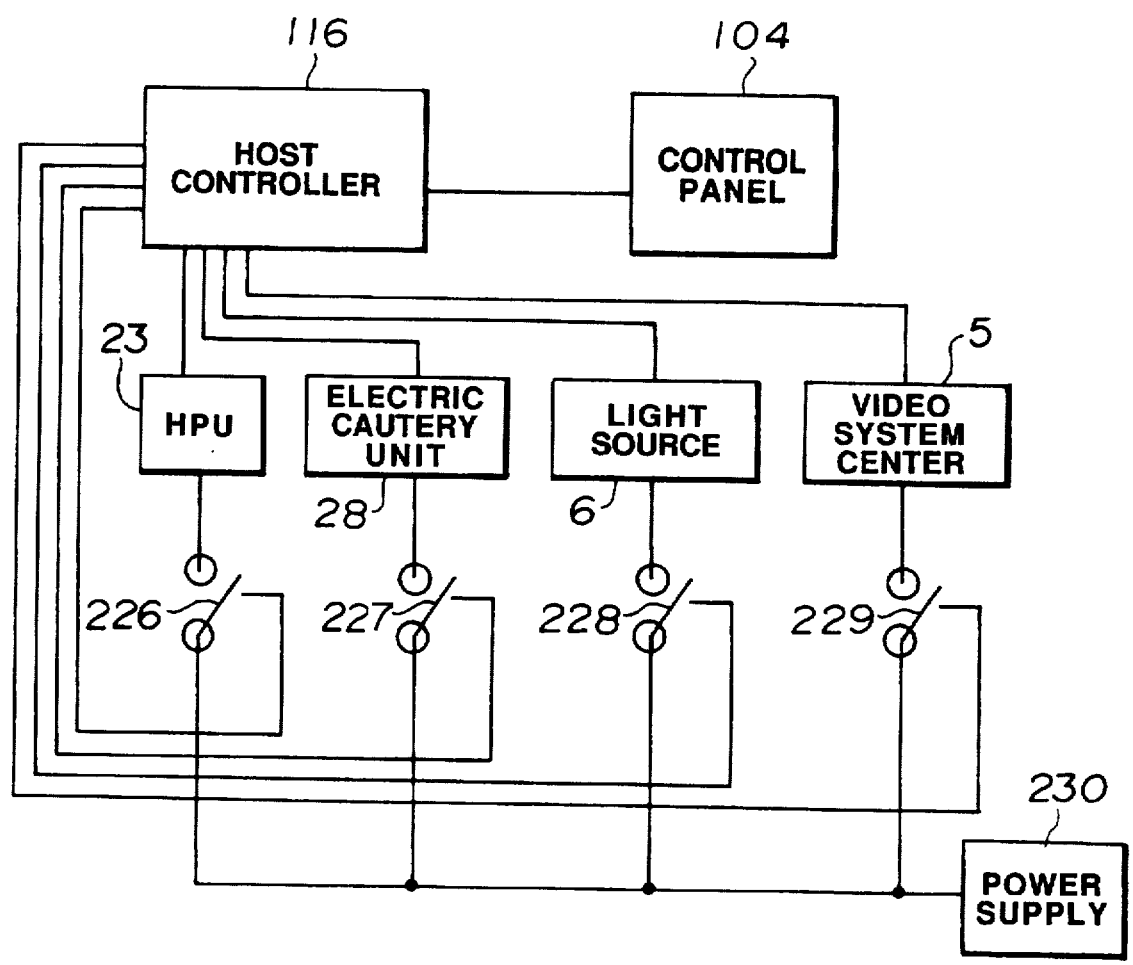
FIG. 64 is a block diagram showing a functional structure related to power supply control for peripheral equipment in the second embodiment.

FIG. 64 is a block diagram showing a functional structure for power supply control in an endoscope system. The host controller 116 receives input entered at the control panel 104, and controls the heat prove unit (HPU) 23, electric cautery unit 28, light source apparatus 6, and video system center 5 respectively. The HPU 23, electric cautery unit 28, light source apparatus 6, and video system center 5 are connected to a power supply 230 via relay switches 226, 227, 228, and 229. The on or off states of these relay switches 226, 227, 228, and 229 are controlled by the host controller 116.

In the main operation screen 131 shown in FIG. 19, when the HEAT PROBE switch 144 displayed in the lower center of the screen 131 is pressed, the host controller 116 changes the screen of the control panel 104 to the heat probe unit operation screen 135 shown in FIG. 23. The host controller 116 turns on the relay switch 226 only when the OUTPUT switch, which is located at the moderately lower right corner of the screen 135 and has a capability of a power switch, is pressed. The heat probe unit 23 is thus energized. Meanwhile, the host controller 116 stores the state of the power switch set in the operation screen in memory.

In the heat probe unit operation screen 135, when the EVIS switch 141 displayed in the lower left end thereof is pressed, the host controller 116 calls the original main operation screen 131. At the same time, the host controller 116 turns off the relay switch 226 to de-energize the heat probe unit 23. According to this kind of control sequence, even when the output of the heat probe unit 23 cannot be monitored; that is, for example, the main operation screen 131 shown in FIG. 19 is displayed, an accident caused by stepping on the output foot switch by mistake can be avoided.

When the HEAT PROBE switch 144 is pressed again, the host controller 116 references the stored state of the power switch and determines whether the relay switch 226 should be turned on or off. Specifically, in this case, since operation screens were changed with the relay switch 226 on, the relay switch 226 is turned on to energize the heat probe unit 23.

According to the foregoing control sequence, after the power supply is turned off because the associated operation screen is escaped, when the operation screen is called again, an operator will not be bothered by a nuisance of turning on the power switch.

The same is true for the control of the electric cautery unit 28. When the DIATHERMY switch 145 displayed in the moderately right-hand lower center of the main operation screen 131 is pressed, the host controller 116 calls the electric cautery unit operation screen 136 shown in FIG. 24. The relay switch 227 connected to the electrical cautery unit 28 is turned on only when the electric cautery unit operation screen 136 is displayed and the OUTPUT switch, which is located in the moderately lower right end of the operation screen 136 and has a capability of a power switch, is turned on. The state of the power switch is stored in memory in the host controller 116. When the operation screen 136 is called from another operation screen, if the stored state of the power switch is on, the host controller 116 turns on the relay switch 227. If the stored state of the power switch is off, the relay switch 227 is turned off.

Figure 65:
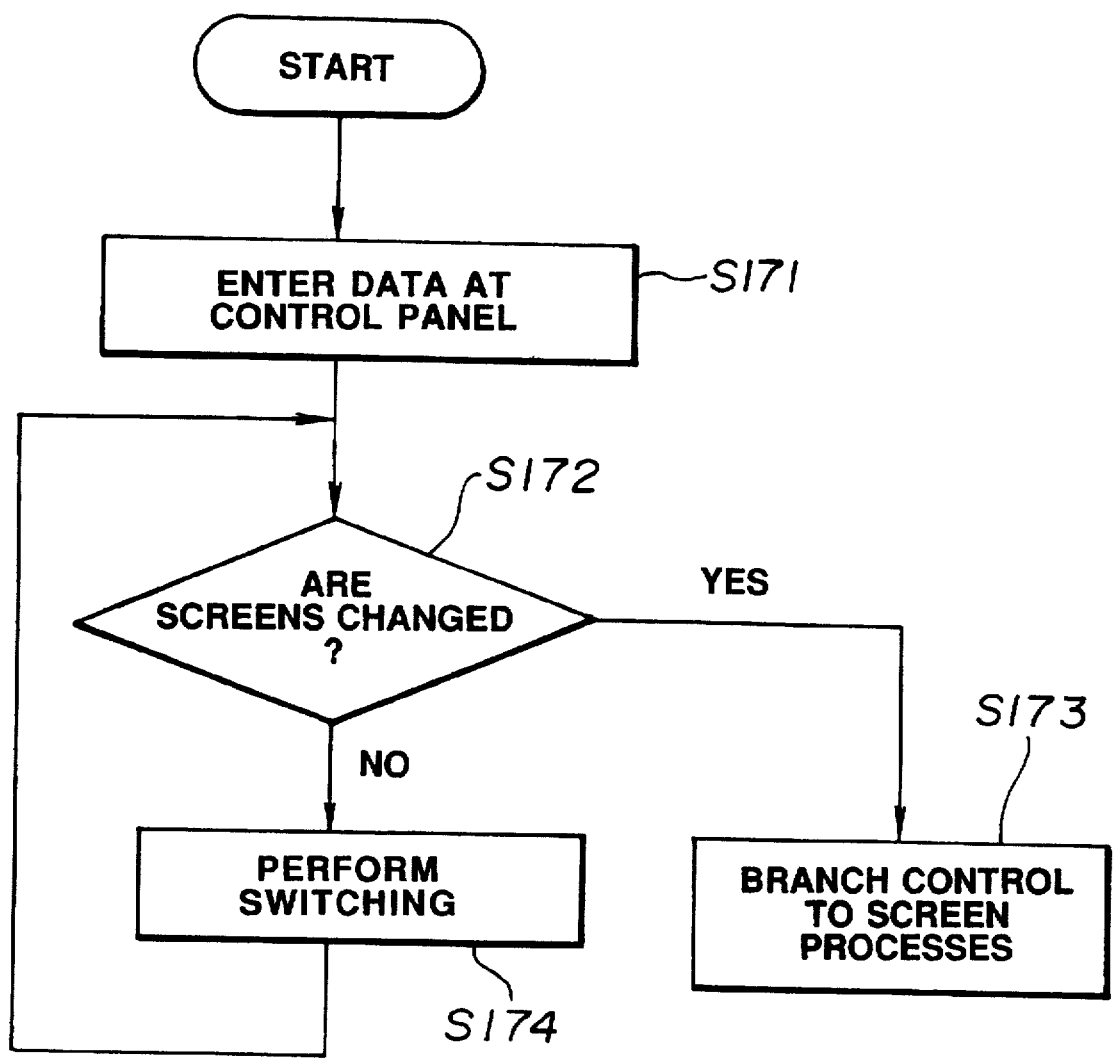
FIG. 65 is a flowchart showing the control operations not including the on or off control of power supply to be performed when the main operation screen or the like is displayed.
Figure 66:
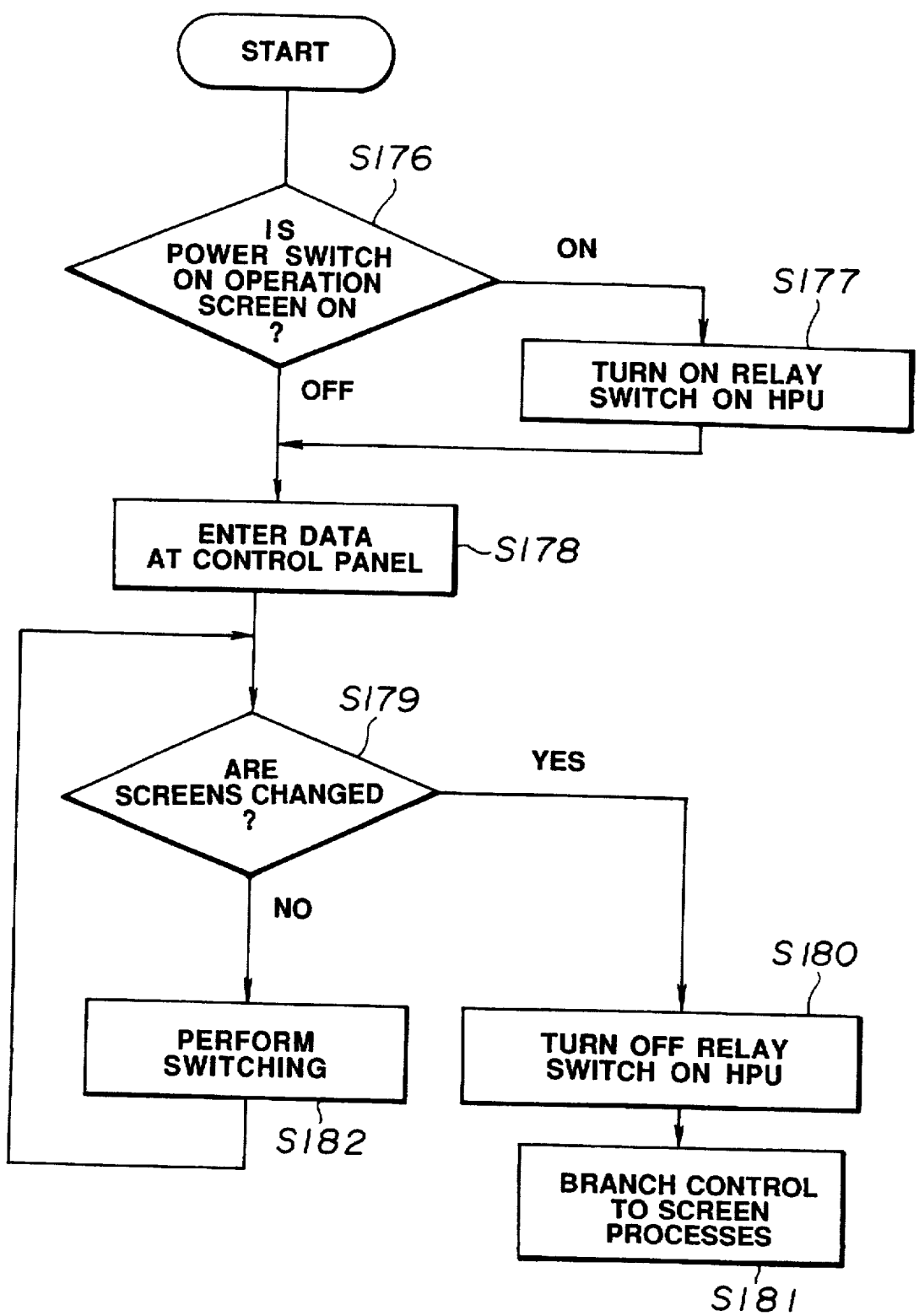
FIG. 66 is a flowchart showing the operations including power supply control to be performed when a heat probe unit operation screen is displayed.

FIGS. 65 and 66 show the foregoing control sequences. FIG. 65 is a flowchart of control extended when the main operation screen is displayed. FIG. 66 is a flowchart of control extended when the heat probe unit operation screen is displayed.

For the main operation screen or any other operation screen in which the power supply of a unit is not controlled, as shown in FIG. 65, input is provided at the control panel at a step S171. At a step S172, it is determined whether the input designates screen change. If the input designates screen change, the host controller 116 advances to a step S173 and branches control to any other screen process. If the input does not designate screen change, switching is performed according to the input at a step S174. Thereafter, the host controller 116 returns to the step S172 and determined if the input designates screen change.

Referring to FIG. 66, power supply control for a heat probe unit will be described.

When the heat probe unit operation screen 135 is selected, it is determined at a step S176 whether the power switch displayed in the operation screen of the control panel 104 is on or off. If the stored state of the power switch is on, the host controller 116 turns on the relay switch 226 at a step S177 and provides the touch panel with input at a step S178. If the power switch is off, the host controller 116 advances to the step S178 as it is and provides the touch panel with input. When input is provided at the control panel 104 at the step S178, it is determined at a step S179 whether the input designates screen change. If the input designates screen change, the host controller 116 advances to a step S180, turns off the relay switch 226, and then branches control to any other screen process at a step S181. If the input does not designate screen change, switching is performed according to the input at a step S182. The host controller 116 then returns to the step S179 and determines whether screen change is designated.

According to the aforesaid power supply control means in peripheral equipment of an endoscope system, the power supplies of the peripheral equipment can be controlled without providing unintended erroneous output and following a bothersome procedure.

FIGS. 67 to 70 show the third embodiment of the present invention.

The third embodiment represents another example of an arrangement of an endoscope system in which the configuration of the second embodiment shown in FIG. 16 is implemented.

Figure 67:
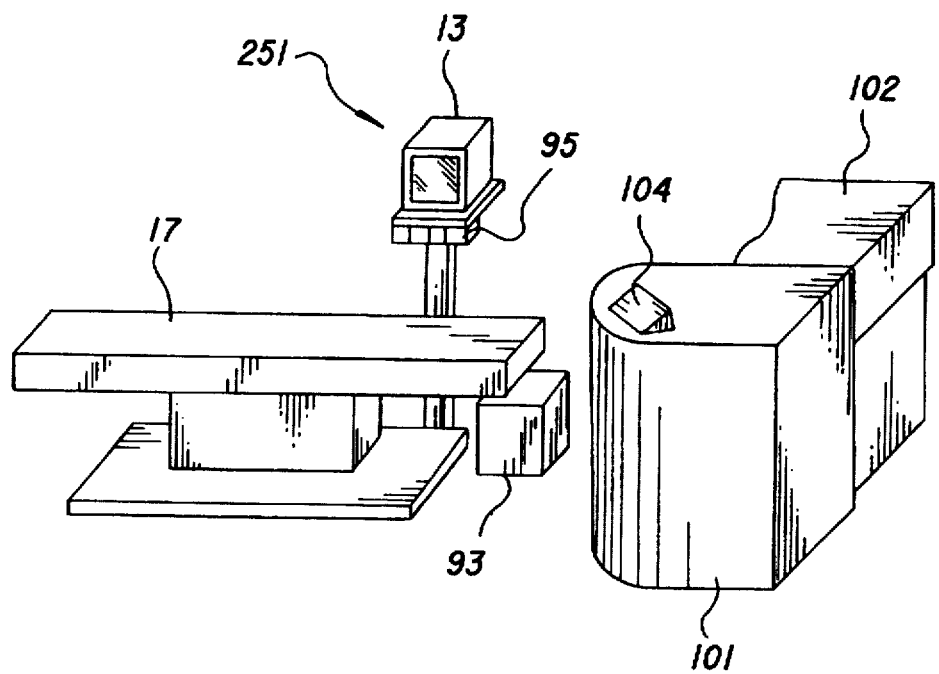

As shown in FIG. 67, an endoscope system 251 of the third embodiment comprises a motor-driven bed capable of moving vertically and longitudinally, a blood pressure gauge 93 for metering a patient's blood pressure, a monitor 13 for displaying endoscopic images, a doctor workstation 101 including an external control panel 104, a nurse workstation 102, a biomedical information display 95 for displaying biomedical information such as a blood pressure, a heart rate, and a blood oxygen saturation, and, for example, a solid-state or mobile stretcher, which is not shown, for carrying a patient thereon.

Figure 68:
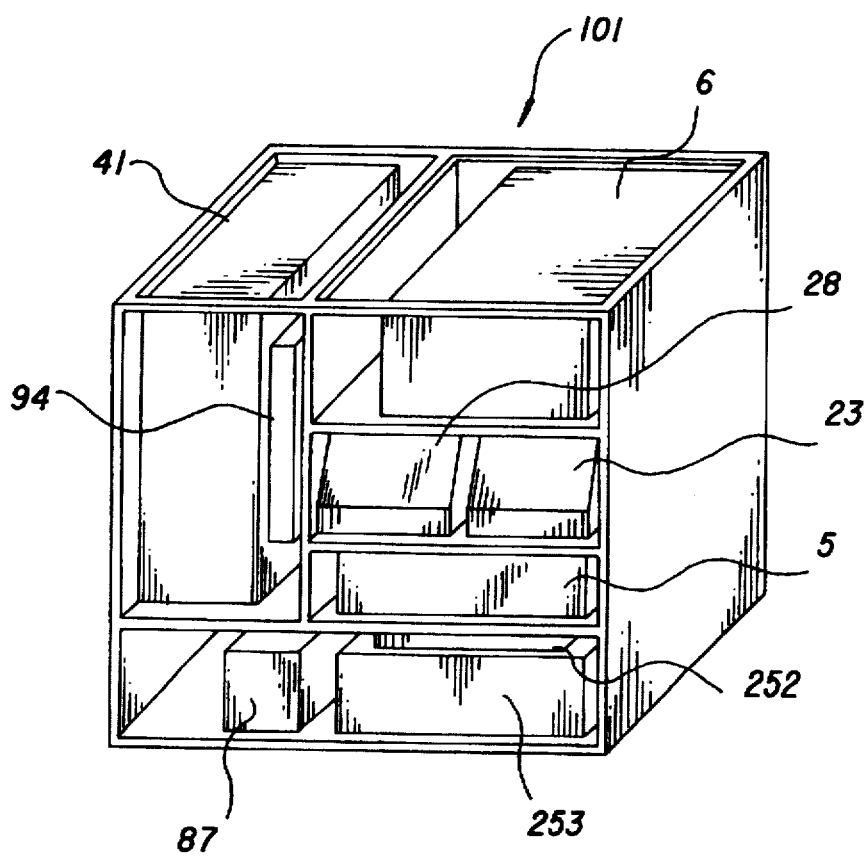

The doctor workstation 101 comprises, as shown in FIG. 68, a blood oxygen saturation measuring unit (pulse oximeter) 94 for metering a patient's heart rate or blood oxygen saturation, a light source apparatus 6 for supplying illumination light to a subject via an endoscope, a video system center 5 for processing image signals sent from an endoscope, a monitor image photography unit 41 that has a monitor, which is not shown, for displaying images sent from an endoscope, and that photographs monitor images, a diathermy (heat probe unit) 23 for cauterizing a lesion for treatment, an electric cautery unit 28 for resecting a lesion, a data acquisition unit 252 for acquiring biomedical information from the blood pressure gauge 93 and pulse oximeter 94, a suction pump 87 for sucking body fluid or the like, and a host controller 253 for controlling the above units.

Figure 69:
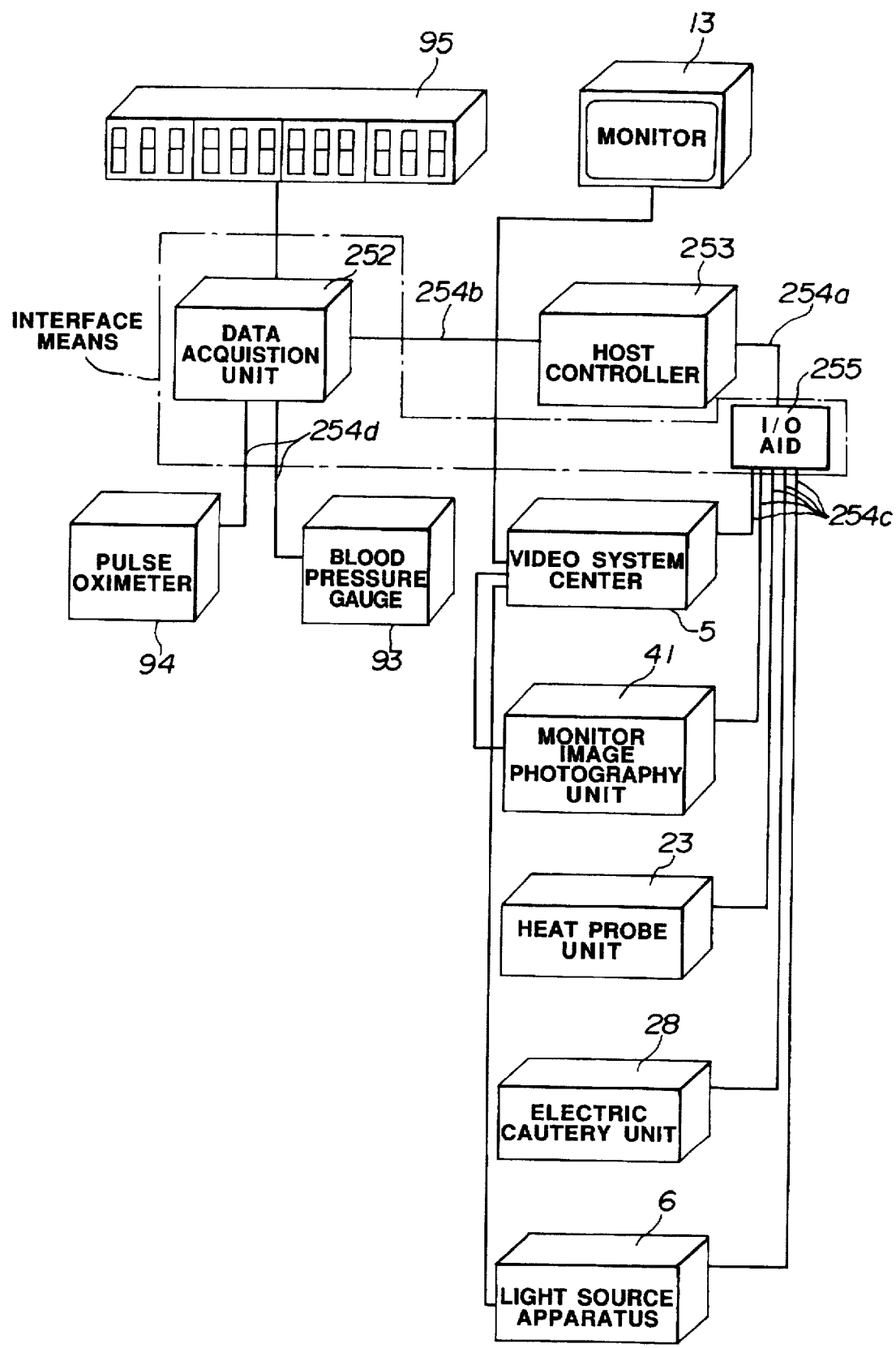

Next, the operation of the endoscope system 251 will be described using FIG. 69 showing a functional structure of the system.

As shown in FIG. 69, the host controller 253 is connected to an input/output (I/O) aid 255 and the data acquisition unit 252 over RS-232C-conformable transmission lines 254a and 254b respectively. The I/O aid 255 is connected to the video system center 5, monitor image photography unit 41, heat probe unit 23, electric cautery unit 28, and light source apparatus 6 over multiple RS-232C-conformable transmission lines 254c. The host controller 253 controls the above units over the transmission lines 254a and 254b, and the transmission lines 254c via the I/O aid 255.

Illumination light is supplied from the light source apparatus 6 into an endoscope which is not shown, a subject is imaged, and then the image signal is processed by the video system center 5. Finally, an endoscopic image is displayed on the monitor 13.

The pulse oximeter 94 and blood pressure gauge 93 are connected to the data acquisition unit 252 over RS-232C-conformable transmission lines 254d. Biomedical information measured by the pulse oximeter 94 and blood pressure gauge 93; such as, a blood oxygen saturation, a heart rate, a maximum blood pressure, and a minimum blood pressure are acquired by the data acquisition unit 252. The data acquisition unit 252 displays the acquired biomedical information on the biomedical information display 95 using a display drive unit, which is not shown, in the data acquisition unit 252. The biomedical information display 95 is installed near the monitor; that is, at a position at which a doctor undertaking treatment can catch an endoscopic image and a biomedical information display within his/her single field of view. Acquired biomedical information is thus displayed at a single place.

As mentioned above, in this embodiment, the host controller 253 is connected to peripheral equipment via interface means that are the data acquisition unit 252 and I/O aid 255. In this state, the peripheral equipment are controlled and biomedical information provided by the peripheral equipment are displayed.

The endoscope system 251 of this embodiment can therefore realizes easy-to-see display which is not limited to a specific field in the monitor screen, does not reduce characters in size, and does not restrict a display range, as long as a biomedical information display and a monitor screen are installed independently of each other. A doctor can obtain endoscopic image information and biomedical information as distinctively separated information. The biomedical information display 95 for displaying biomedical information all together is installed near the monitor 13, which allows a doctor to verify endoscopic image information and biomedical information with ease without moving his/her line of sight drastically. This helps alleviate an operator's fatigue and avoid a use error resulting from movement of a line of sight during an endoscopic procedure.

FIG. 70 shows a variant of the arrangement of a biomedical information display.

This variant is provided with a means enabling a biomedical information display to swivel or rock vertically or laterally. The other components are identical to those of the third embodiment. Only the different component will be described.

Figure 70A:
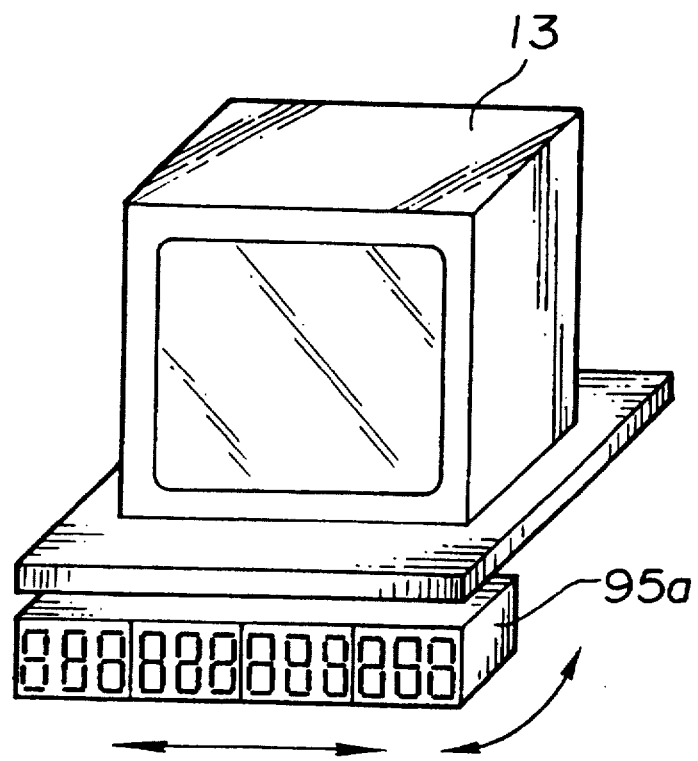
FIGS. 70a and 70b are explanatory diagrams showing a variant of a biomedical information display.
Figure 70B:
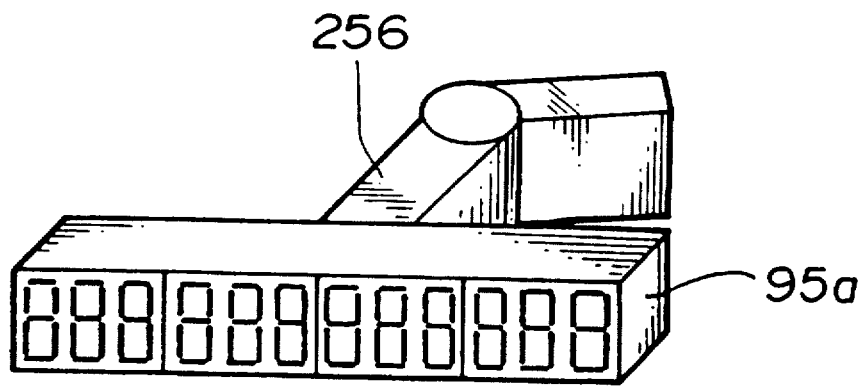

A biomedical information display 95a installed near the monitor 13 as shown in FIG. 70a includes at least one rocker 256 as shown in FIG. 70b. The rocker 256 is driven manually or by a drive unit which is not shown, thus enabling lateral swiveling or rocking. The other components and the operation are identical to those of the third embodiment.

This variant has the same advantages as the third embodiment as well as the following advantages: since the biomedical information display 95a can be oriented in any desired direction, a viewing difficulty a doctor confronts depending on his/her position can be resolved, and visibility can be improved for a nurse and other people concerned who are not doctors.

Lateral swiveling or rocking are achieved by driving the rocker 256. Alternatively, a rocker for enabling vertical swiveling or rocking may be employed, or multiple rockers may be employed to enable vertical and lateral swiveling or rocking.

Figure 71:
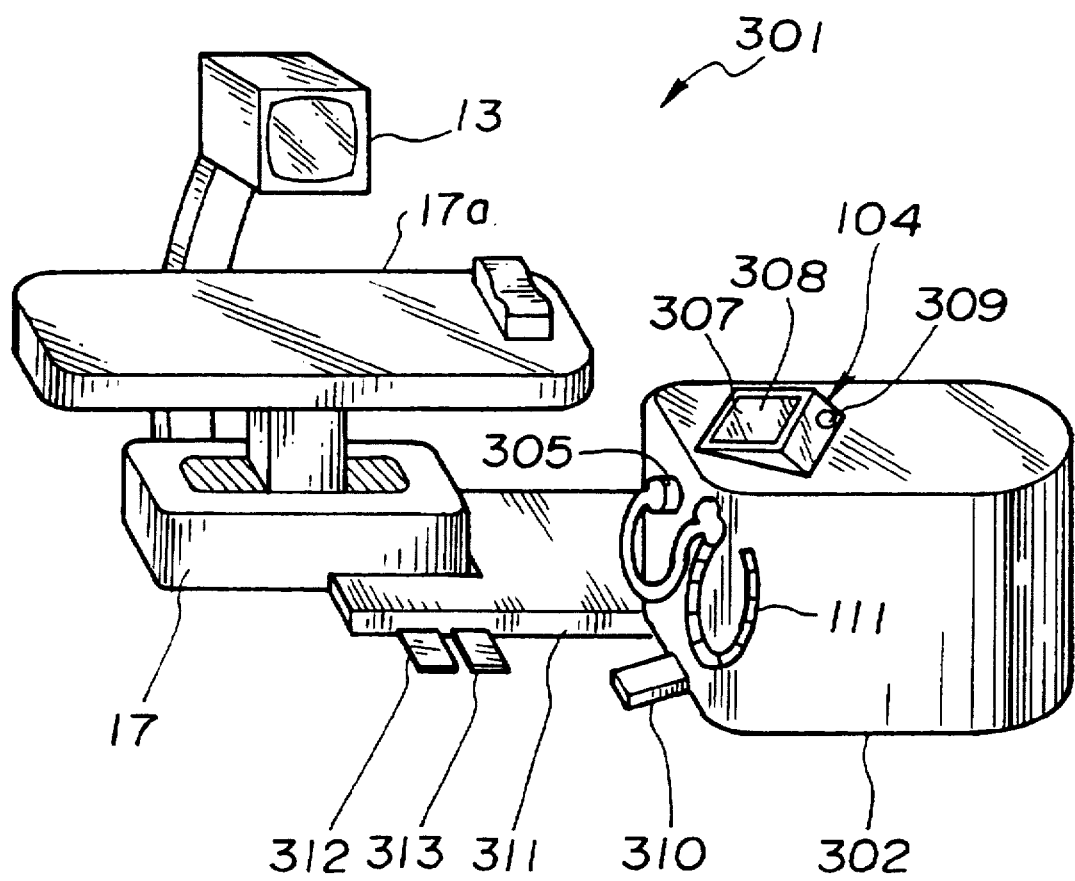
FIGS. 71 and 72 relate to the fourth embodiment of the present invention.
Figure 72:
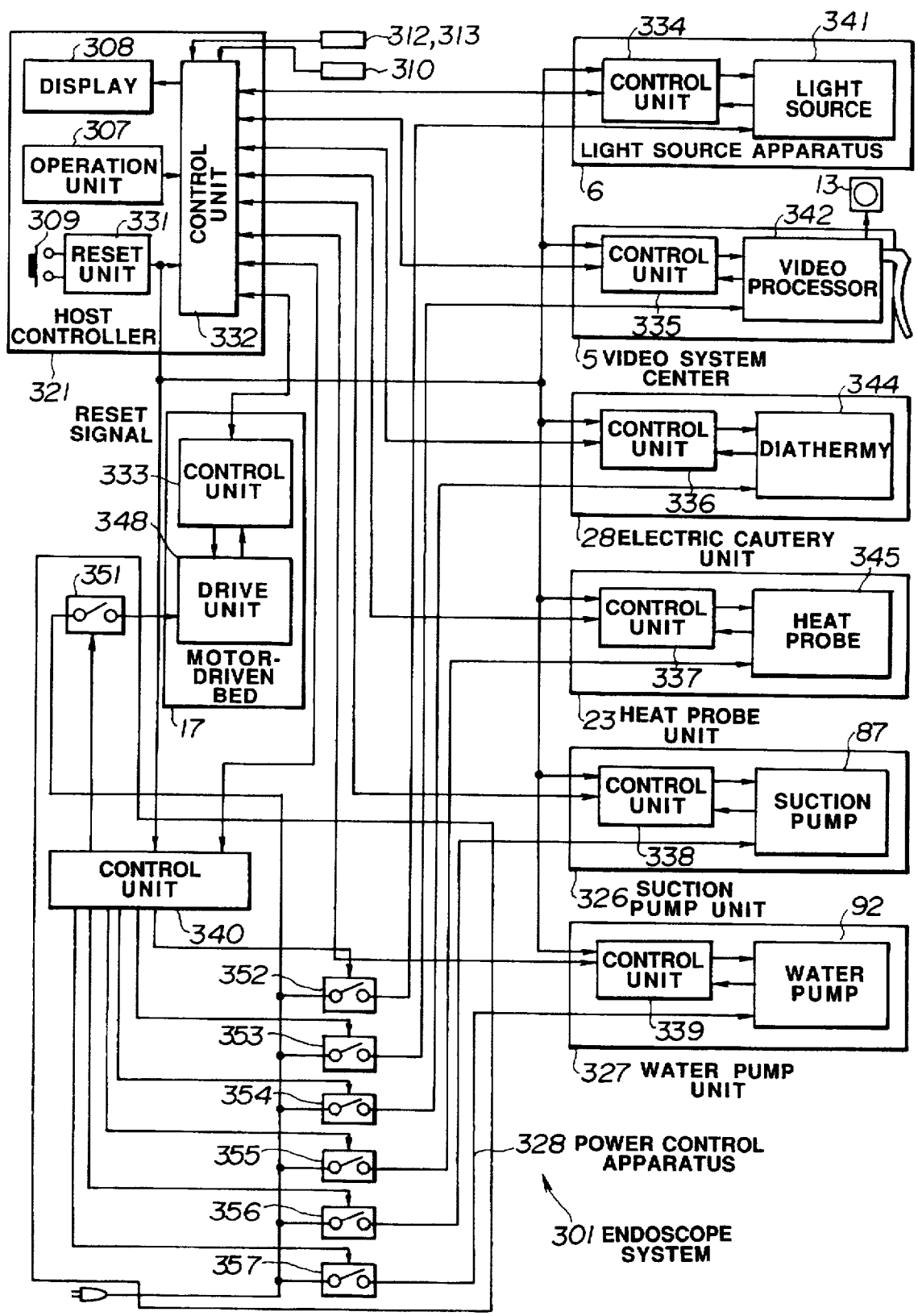

FIGS. 71 and 72 show the fourth embodiment of the present invention.

In an endoscope system using a host controller to centralize the control of peripheral equipment, if any of the peripheral equipment including a light source apparatus or the host controller runs abnormally due to external noises or a software bug, all the equipment of the system may become uncontrollable and unnecessary equipment may be put in an operational state. If an abnormal run occurs in an endoscope system, a user usually turns off the power supply of the entire system in order to protect a patient from being jeopardized by an electric cautery unit, a heat probe unit, a suction pump, a water pump, or a motor-driven bed.

At the time when an endoscope system runs abnormally, an endoscope probe may lie in a patient's body. In this case, even when the power supply of the entire system is turned off and then turned on again, a light source lamp indispensable for picking up endoscopic images will not light until an ignition switch is pressed. In the meantime, endoscopic images cannot therefore be monitored. It is therefore highly possible that the endoscope probe itself lying in a patient's body or a treatment adapter at the tip of the endoscope probe injures the patient.

The fourth embodiment is therefore provided with a reset means that when a system runs abnormally, actuates an endoscope apparatus alone and stops other peripheral equipment. Owing to the means, the system can be reset to a normal state without turning off the power supply of the entire system. Endoscopic images can thus be observed uninterruptedly.

As shown in FIG. 71, an endoscope system 301 adopts a motor-driven bed unit 17 as a patient table. In the motor-driven bed unit 17, a bed 17a can be moved when driven by a drive unit. A monitor unit 13 is located on one side of the motor-driven bed unit 17. An operator (not shown) standing on the other side of the motor-driven bed unit 17 can easily observe endoscopic images on the monitor unit 13 while treating a patient on the bed 17a. A workstation 302 is located alongside of the operator.

A connector 305 is formed on the side of the workstation 302 facing an operator, to which an endoscope 111 can be connected. A light source apparatus for the endoscope, a video system center, an electric cautery unit, a heat probe unit, a suction pump, and a water pump are accommodated in the workstation 302. A control panel 104 serving as an operation unit for a host controller that controls various equipment is placed on the workstation 302. The control panel 104 includes an operating section 307, a display section 308, and a reset switch 309.

A foot switch 310 for controlling the motor-driven bed unit 17 is formed at the lower end of the side of the workstation 302 facing an operator. A floor base 311 is placed on the floor between the workstation 302, and the motor-driven bed unit 17 and monitor unit 13, wherein cables extending from the host controller are enclosed. Foot switches 312 and 313 for use in controlling the electric cautery unit and heat probe unit are formed on the side of the floor base 311 facing an operator.

In the endoscope system 301 of this embodiment, as shown in FIG. 72, the host controller 321 controls a light source unit 6, a video system center 5, an electric cautery unit 28, a heat probe unit 23, a suction pump unit 326, a water pump unit 327, and the motor-driven bed unit 17. The host controller 321 is a microcomputer. A control unit 332 in the host controller 321 is connected to control units 333 to 340 in the peripheral equipment, and thus transfers control signals thereto or therefrom. The control unit 332 outputs various control signals according to an operator's input to the operating section 307, and thus controls pickup and display of endoscopic images, operation of the electric cautery and heat probe units, and suction and water supply. The display section 308 displays operation screens or the like.

In this embodiment, the host controller 321 includes the reset switch 309 that resets the system when pressed by a user. When it is detected that the reset switch 309 is pressed or a watch dog timer is actuated to report that software is running abnormally, a reset unit 331 supplies a reset signal to the host controller 321 as well as the control units 332 to 340 of the peripheral equipment. The control unit 332 in the host controller 321 extends control according to the signals sent from the foot switch 310 for controlling the motor-driven bed unit 17 as well as the foot switches 312 and 313 for controlling the electric cautery unit 28 and heat probe unit 23 respectively.

The light source apparatus 6 comprises a light source 341 for an endoscope and the control unit 334 for controlling the light source 341. The control unit 334 transfers a control signal to or from the control unit 332 in the host controller 321. In response to a reset signal from the reset unit 331, the control unit 334 puts the light source 341 into an operational state forcibly, so that illumination light will be supplied to the endoscope 111.

A video processor 342 in the video system center 5 inputs an image signal from the endoscope 111, converts it into a standard video signal by performing specified video processing, and then outputs the video signal to the monitor unit 13. The control unit 335 transfers a control signal to or from the control unit 332 in the host controller 321, and thus controls the video processor 342. In response to a reset signal from the reset unit 331, the control unit 335 puts the video processor 342 into an operational state so that an endoscope video signal will be output to the monitor unit 13.

The electric cautery unit 28 comprises a diathermy 344 and the control unit 336. The control unit 336 transfers a control signal to or from the control unit 332 in the host controller 321, and thus controls the diathermy 344. The diathermy 344 drives an electric cautery, which is not shown, under the control of the control unit 336. As described previously, the electric cautery unit 28 is controllable using the foot switch 312. In this embodiment, the control unit 336 is initialized with a reset signal sent from the host controller 321.

The control unit 337 in the heat probe unit 23 transfers a control signal to or from the control unit 332 in the host controller 321. A heat probe section 345 drives a heat probe which is not shown. The control unit 337 controls the heat probe section 345 according to the control signal, and is initialized with a reset signal sent from the host controller 321. The heat probe unit 23 is controllable using the foot switch 313.

The suction pump unit 326 includes the control unit 338 and a suction pump 87. The control unit 338 transfers a control signal to or from the control unit 332 in the host controller 321, and thus controls the suction pump 87. The suction pump 87 sucks body fluid or the like from the distal part of the endoscope 111. In this embodiment, the control unit 338 is initialized with a reset signal.

The water pump unit 327 comprises a water pump 92 for splashing water from the distal part of the endoscope 111 and the control unit 339 for controlling the suction pump 92. The control unit 339 transfers a control signal to or from the host controller 321, and thus controls the water pump 92. The control unit 339 is initialized with a reset signal.

The motor-driven bed unit 17 comprises the control unit 333 and a drive unit 348. The control unit 333 transfers a control signal to or from the control unit 332 in the host controller 321, and thus controls the drive unit 348. The drive unit 348 drives and moves the bed 17a. The motor-driven bed unit 17 is controllable using the foot switch 310. In this embodiment, the control unit 333 is initialized with a reset signal from the host controller 321.

In this embodiment, AC supply voltage is applied to the drive unit 348, light source 341, video processor 342, diathermy 344, heat probe section 345, suction pump 87, and water pump 92, which are included in peripheral equipment, via relays 351 to 357 in a power supply control unit 328. The on or off states of the relays 351 to 357 are controlled by a control unit 340. In other words, the control unit 340 controls the relays 351 to 357 according to the control signals sent from the control unit 332 in the host controller 321. The control unit 340 neither turns on the relays 354 and 355 simultaneously nor enables the simultaneous use of the electric cautery unit 28 and heat probe unit 23. In this embodiment, when a reset signal sent from the reset unit 331 is supplied to the control unit 340, the control unit 340 turns on the relays 352 and 353 but turns off the other relays 351 and 354 to 357.

Next, the operations of this embodiment having the aforesaid components will be described.

For normal use, the peripheral equipment are controlled by the host controller 321. A user operates the operation unit 307 in the host controller 321 and the foot switches 310, 312, and 313, thus using the peripheral equipment. Assuming that the endoscope 111 is inserted into a patient's body and endoscopic images are displayed on the monitor unit 13, the control unit 332 in the host controller 321 transmits a control signal to each of the control units 334 and 335. The light source 351 and video processor 342 are then put into operational states. In this case, the control unit 340 turns on the relays 352 and 353 and thus applies AC supply voltage to the light source 341 and video processor 342.

When the heat probe is used for cauterization, the operation unit 307 in the host controller 321 is used to issue an instruction saying that the power supply of the heat probe should be turned on. The control unit 332 transmits a control signal to the control unit 340. The relay 355 is then turned on to apply AC supply voltage to the heat probe section 345. Thereafter, when an operator steps on the foot switch 313, the control unit 332 sends a control signal to the control unit 337. The heat probe section 345 then enters an operational state. The control unit 340 neither turns on the relays 354 and 355 simultaneously nor enables the simultaneous use of the diathermy 355 and heat probe section 345.

Supposing software runs abnormally in the host controller 321, when the watch dog timer, which is not shown, detects the fact, the reset unit 331 generates a reset signal. The reset signal is supplied to each of the control unit 332 in the host controller 321 and the control units 333 to 340 in the peripheral equipment. The control unit 332 in the host controller 321 is initialized with a reset signal. Meanwhile, the control unit 340 turns on the relays 352 and 353. The control units 334 and 335 put the light source 341 and video processor 342 into operational states forcibly. The light source 341 supplies illumination light to the endoscope. The video processor 342 processes image signals into video signals. The video signals are then displayed on the monitor unit 13. In short, if the system runs abnormally, the host controller 321 stops control but endoscopic images are displayed uninterruptedly.

With the reset signal, the control unit 340 turns off the relays 351, and 354 to 357, and initializes the control units 333, and 336 to 339. That is to say, immediately after the system runs abnormally, the motor-driven bed unit 17, electric cautery unit 28, heat probe unit 23, suction pump unit 236, and water pump unit 327 stops operating. Thus, even when the system runs abnormally, a patient will not be jeopardized.

If an operator finds that the system operates abnormally, the operator presses the reset switch 309. A reset signal is then generated from the reset unit 331. The same processing as that performed when the system runs abnormally will be carried out.

As described above, according to this embodiment, if the system runs abnormally, the reset unit 331 generates a reset signal and supplies it to the power supply control unit 328. The power supply control unit 328 applies supply voltage to video-related equipment including the light source apparatus 6 and video system center 5, but stops feeding supply voltage to equipment that may jeopardize a patient; such as, the electric cautery unit 28, heat probe unit 23, suction pump unit 326, water pump unit 327, and motor-driven bed unit 17. Even when a system failure occurs, patient's safety can be ensured.

In the system shown in FIG. 71, the foot switch 310 for operating the motor-driven bed unit 17 is separated from the foot switches 312 and 313 for operating the electric cautery unit 28 and heat probe unit 23. This prevents an operator from actuating the electric cautery unit 28 or heat probe unit 23 by mistake while intending to actuate the motor-driven bed unit 17.

According to this embodiment, even if the system runs abnormally, the system can be reset to a normal state without turning off the power supply. Endoscopic images can therefore be observed uninterruptedly. Patient's safety can thus be assured.

In the present invention, it will be apparent that a wide range of different embodiments can be formed on the basis of the invention without departing from the spirit and scope of the invention. This invention is limited to the appended claims but not restricted to any specific embodiments.

What is claimed is:

1. An endoscope system comprising:
   a plurality of endoscope system means including at least one illumination light supply means for supplying illumination light to an endoscope and at least one video signal processing means for processing video signals provided by said endoscope;
   main control means for controlling said plurality of endoscope system component means; and
   main operation instruction means connected to said main control means and used to operate said plurality of endoscope system component means;
   said main operational instruction means for customizing a main screen by displaying a plurality of representations of functions of said plurality of endoscope component means, selecting one or more of the displayed representations of said functions of said plurality of endoscope component means, and display means for first displaying said main screen including the selected representations of selected functions of said plurality of endoscoope system component means, and then, in response to a further selection from said main screen of one said selected representations of said selected functions of said plurality of endoscope system component means, for displaying an operational instruction input screen associated with the further selected representation.

2. An endoscope system, comprising:
   a plurality of endoscope system components including at least one endoscope light source apparatus for supplying illumination light to an endoscope and at least one video signal processing unit for processing video signals provided by said endoscope;
   main control unit for controlling said plurality of endoscope system components; and
   main operational instruction means connected to said main control unit and used to operate said plurality of endoscope system components;
   said main operational instruction means including
      a selective input section for selecting any one of said plurality of endoscope system components;
      means for customizing a main screen by displaying a plurality of representation of functions of said plurality of endoscope component means, selecting one or more of the displayed representations of said functions of said plurality of endoscope system components; and
      a display section for first displaying said main screen including the selected representations of said functions of said plurality of endoscope system componenets selected by said means for customizing a main screen and then for displaying an operational instruction input screen associated with one of said representations of said functions selected form said main screen according to an operation performed on said selective input section.

3. An endoscope system according to claim 1, wherein said main operational instruction means is set to a state for enabling a description to be input regarding a first specified function possessed by said plurality of endoscope system components and wherein said display section displays the input description after selection of said first specified function according to an operation performed on said selective input section.

4. An endoscope system according to claim 3, wherein said main operational instruction means displays a selected operational instruction screen, which is associated with said first specified function, in said display section, and enables said description to be displayed in the operational instruction input screen.

5. An endoscope system according to claim 3, wherein said main operational instruction means displays a selected operational instruction input screen, which is associated with any of said plurality of endoscope system component means, in said display, and enables said description displayed in the operational instruction input screen.

6. An endoscope system according to claim 1, wherein said display means in said main operational instruction means is an LCD, CRT, EL, or plasma display; and said main operational instruction means includes an instruction input section that is a touch panel mounted on said display.

a mouse, a joystick, a keyboard, a trackball, a digitizer, or a combination thereof.

7. An endoscope system, comprising:

a plurality of endoscope system component means including at least one illumination light supply means for supplying illumination light to an endoscope and at least one video signal processing means for processing video signals provided by said endoscope;

a main control means for controlling said plurality of endoscope system component means; and a main operational instruction means including a plurality of labeled switches connected to said main control means and used to operate said plurality of endoscope system component means;

said main operational instruction means including a display means for selectively displaying textual descriptions of the functions of said plurality of labeled switches used to operate said plurality of endoscope system component means;

wherein said plurality of endoscope system component means include a treatment apparatus for use in treating a subject and a motor-driven bed unit on which a patient lies down; and said main operational instruction means can selectively display at least an electronic endoscope operation screen usable for the functions operated when an electronic endoscope is connected, a fiberscope operation screen usable for the functions operated when a fiberscope is connected, and a treatment apparatus operation screen usable for a treatment apparatus, and can also display a bed operation screen usable for said motor-driven bed unit in part of at least said electronic endoscope operation screen or fiberscope operation screen.

8. An endoscope system according to claim 7, wherein said main operational instruction means can display an electronic endoscope setting screen that lies in a lower hierarchy than said electronic endoscope operation screen and can be modified in terms of setting parameters for use of an electronic endoscope, and can also display a fiberscope setting screen that lies in a lower hierarchy than said fiberscope operation screen and can be modified in terms of setting parameters for use of a fiberscope.

9. An endoscope system according to claim 7, wherein said main control means enables a treatment apparatus associated with a treatment apparatus operation screen to operate only when the treatment apparatus operation screen is displayed in said main operational instruction means.

10. An endoscope system according to claim 1, wherein said main operational instruction means has a hierarchy made up of a plurality of operational instruction input screens associated with the functions of said plurality of endoscope system component means; and screen select switches are formed so that screens in other hierarchies can be selected irrelevant of the hierarchy of a current operational instruction input screen.

11. An endoscope system according to claim 10, wherein said main operational instruction means has said screen select switches as parts of said plurality of operational instruction input screens.

12. An endoscope system according to claim 10, wherein card-type screen display is implemented in said plurality of operational instruction input screens of said main operational instruction means; and a caption area displaying text describing the functions of said screen select switches is formed in each operational instruction input screen.

13. An endoscope system according to claim 1, wherein a plurality of operational instruction input screens of said main operational instruction means are associated with the functions of said plurality of endoscope system component means, grouped by specified functions, and made into a hierarchy by groups.

14. An endoscope system according to claim 13, wherein each of said operational instruction input screens of said main operational instruction means can be shifted to any hierarchy among the groups of said operational instruction input screens irrelevant of the hierarchy of a current operation input screen.

15. An endoscope system according to claim 13, wherein each of said operational instruction input screens of said main operational instruction means can be shifted to a highest hierarchy of any of the groups of said operational instruction input screens irrelevant of the hierarchy of a current operation instruction input screen.

16. An endoscope system according to claim 1, further including:

a sub-operational instruction means for enabling instruction input to a specified one of the functions possessed by said plurality of endoscope system component means.

17. An endoscope system comprising:

a plurality of endoscope system components including at least one endoscope light source apparatus for supplying illumination light to an endoscope and at least one video signal processing unit for processing video signals provided by said endoscope;

main control unit for controlling said plurality of endoscope system components;

main operational instruction means connected to said main control unit and used to operate said plurality of endoscope system components; and sub-operational instruction means separate from said main operational instruction means and separately connected to said main control unit for enabling instruction input to a preselected function of a plurality of functions possessed by said plurality of endoscope system components; and means for changing said preselected function by selecting one representation of a plurality of displayed representations of functions of said plurality of endoscope components, thereby enabling instruction input to the changed preselected function by said sub-operational instruction means.

18. An endoscope system according to claim 17, wherein said sub-operational instruction means has priority over said operational instruction means functioning.

19. An endoscope system according to claim 17, wherein a specified one of said plurality of functions possessed by said plurality of endoscope system components can be selected and allocated to said sub-operational instruction means as a function to which instruction input is enabled.

20. An endoscope system according to claim 16, wherein said main operational instruction means can display a function setting screen used to select and allocate an instruction input function to said sub-operational instruction means.

21. An endoscope system according to claim 16, wherein said sub-operational instruction means is provided as a scope switch formed on an operational part of an endoscope that is connected to said endoscope system.

22. An endoscope system according to claim 16, wherein said sub-operational instruction means is provided as a foot switch connected to said endoscope system.

23. An endoscope system according to claim 16, wherein said sub-operational instruction means includes a reset signal generating means for generating a reset signal to be sent to said main control means.

24. An endoscope system according to claim 23, further including:
   a reset means that when reset is instructed with a reset signal sent from said reset signal generating means, operates said illumination light supply means and video signal processing means forcibly, and stops the other endoscope system component means from operating.

25. An endoscope system according to claim 1, wherein said plurality of endoscope system component means includes:
   a treatment apparatus for use in treating a subject; and
   a power supply control means that is connected to said main control means and turns on or off the power supplies of said plurality of endoscope system component means;
   said main operation instruction means can selectively display an electronic endoscope operation screen usable for the functions operated when an electronic endoscope is connected, and a treatment apparatus operation screen usable for a treatment apparatus, which are displayed as said operational instruction input screens; and
   said main control means includes a storage means for storing the on or off state of the power supply of a treatment apparatus associated with said treatment apparatus operation screen, controls, when said treatment apparatus operation screen is displayed, the on or off state of only the power supply of a treatment apparatus associated with a treatment apparatus operation screen according to the on or off state stored in said storage means, and turns off the power supply of said treatment apparatus when the operational instruction input screen is called.

26. An endoscope system according to claim 1, further including:
   a sub-display means for displaying information related to said plurality of endoscope system component means, which is provided as an independent unit.

27. An endoscope system according to claim 26, wherein said plurality of endoscope system component means include at least either a pulse oximeter for metering a patient's heart rate and blood oxygen saturation or a blood pressure gauge for metering a patient's blood pressure;
   said sub-display means includes a biomedical information display means for displaying patient's biomedical information provided by said endoscope system component means; and said biomedical information display means displays at least either the values metered by said pulse oximeter or the ones metered by said blood pressure gauge.

28. An endoscope system according to claim 1, wherein said main control means includes an equipment setting storage means for storing a plurality of sets of operator-specific set values for operating said plurality of endoscope system component means; and
   said main operational instruction means can display an operator setting screen for selecting operator-specific set values for operating said plurality of endoscope system component means.

29. An endoscope system according to claim 1, wherein any of said operational instruction input screens of said main operational instruction means has an arbitrary function operation switch area in which operation switches, each of which enables instruction input to a specified one of the functions possessed by said plurality of endoscope system components, can be arranged selectively.

30. An endoscope system according to claim 29, wherein said main operational instruction means enables each operator to set operation switches to be arranged in said arbitrary function operation switch area.

31. An endoscope system according to claim 1, wherein each of said operational instruction input screens of said main operational instruction means has a Help-mode switch for selecting a Help mode in which operational functions in a screen are explained; and when the Help-mode switch is pressed in a screen, a Help-mode screen having an explanation of said operational functions in the screen is displayed.

* * * * *